(12) United States Patent
Asano et al.

(10) Patent No.: US 6,726,936 B1
(45) Date of Patent: Apr. 27, 2004

(54) ANTIMICROBIAL AGENTS

(75) Inventors: Satoshi Asano, Niihama (JP); Yuuichi Yokosawa, Setagaya-ku (JP); Yasutaka Soeda, Niihama (JP)

(73) Assignees: Sumitomo Metal Mining Co., Ltd., Tokyo (JP); Yokosawa Metal Co., Ltd., Saitama (JP)

( * ) Notice: Subject to any disclaimer, the term of this patent is extended or adjusted under 35 U.S.C. 154(b) by 0 days.

(21) Appl. No.: 09/719,983

(22) PCT Filed: Jun. 18, 1999

(86) PCT No.: PCT/JP99/03245

§ 371 (c)(1),
(2), (4) Date: Dec. 19, 2000

(87) PCT Pub. No.: WO99/65317

PCT Pub. Date: Dec. 23, 1999

(30) Foreign Application Priority Data

| Jun. 19, 1998 | (JP) | 10-173549 |
| Oct. 29, 1998 | (JP) | 10-308622 |
| Dec. 15, 1998 | (JP) | 10-356752 |
| Apr. 23, 1999 | (JP) | 11-116014 |
| May 6, 1999 | (JP) | 11-125640 |

(51) Int. Cl.$^7$ .................. A01N 59/16; A01N 59/108; A01N 25/02; A61L 2/16

(52) U.S. Cl. .................. 424/618; 424/404; 424/417; 424/603; 424/76.8; 424/409; 510/319; 510/382; 422/37

(58) Field of Search .................. 424/618, 409, 424/417, 603, 404, 76.8; 510/319, 382; 422/37

(56) References Cited

U.S. PATENT DOCUMENTS

| 4,043,932 | A | * | 8/1977 | Fresenius et al. ........... 424/618 |
| 5,078,902 | A | | 1/1992 | Antelman |
| 5,837,275 | A | | 11/1998 | Burrell et al. |

FOREIGN PATENT DOCUMENTS

| EP | 0 251 783 A2 | 1/1998 |
| EP | 0 875 146 A1 | 11/1998 |
| EP | 1 031 281 A1 | 8/2000 |
| GB | 2 341 394 A | 3/2000 |
| JP | 62-24815 | 2/1987 |
| JP | 1-98624 | 6/1989 |
| JP | 7-304617 | 11/1995 |
| JP | 9-3492 | 1/1997 |
| JP | 9-505112 | 5/1997 |
| JP | 10-182326 | 7/1998 |
| WO | 95/13704 | * 5/1995 |

OTHER PUBLICATIONS

Roberts, Royston M. et al. Modern Experimental Organic Chemistry. 3$^{rd}$ ed., Holt, Rinehart and Winston, New York, pp. 44–56. 1979.*

* cited by examiner

*Primary Examiner*—John Pak
(74) *Attorney, Agent, or Firm*—Nixon & Vanderhye P.C.

(57) ABSTRACT

An antimicrobial agent includes silver-chloro complex salts and chloride, and further oxidizing agents such as sodium hypochlorite or sodium chlorite. As a result, it is possible to provide the antimicrobial agent having immediate and residual disinfecting and antimicrobial effects on bacteria and molds of a wide variety of species and capable of demonstrating instantaneous deodorizing effect. The antimicrobial agent includes the silver-chloro complex salts and chloride, and further a compound, for example, such as alcohols or surfactants, which has compatibility with a solvent such as water which dissolves the chloride. As a result, it is possible to provide the antimicrobial agent which can be used conveniently at the stored concentration, and which has immediate effect and cleansing ability without causing rust or deposition of salts in use. Further, the antimicrobial agent includes the silver-chloro complex salts, and chloride, for example, such as polyaluminium chloride or benzalkonium chloride, which has at least (I) a property capable of existing as a supersaturated aqueous solution in the presence of a crystal nucleus at least at room temperature for 24 hours or longer and (II) a property capable of being decomposed when dissolved in water.

9 Claims, 8 Drawing Sheets

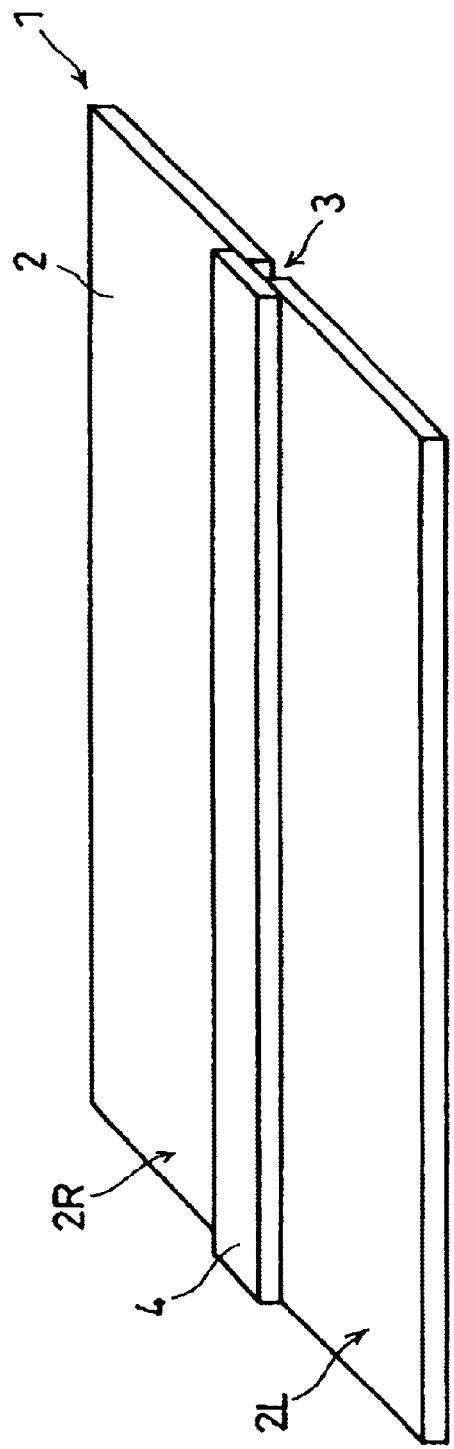
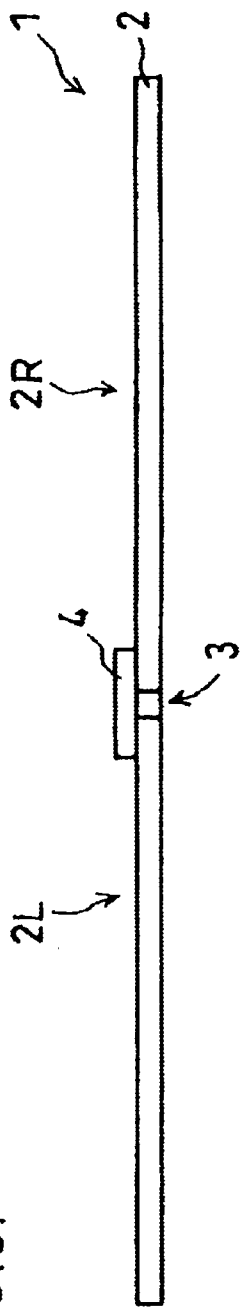
FIG. 2(a)
FIG. 2(b)

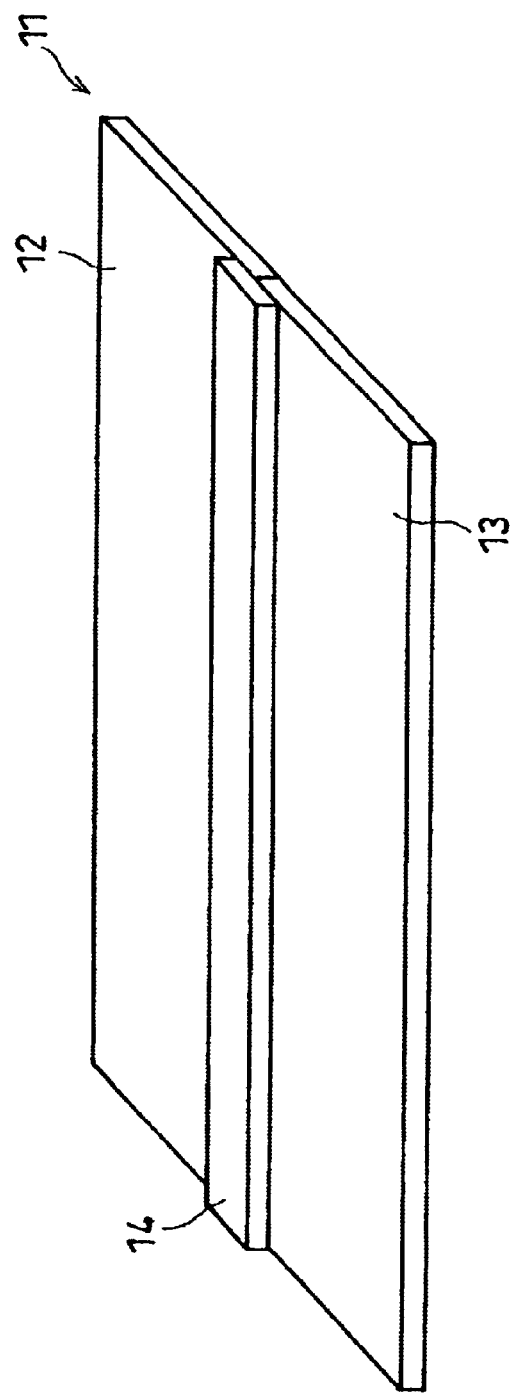
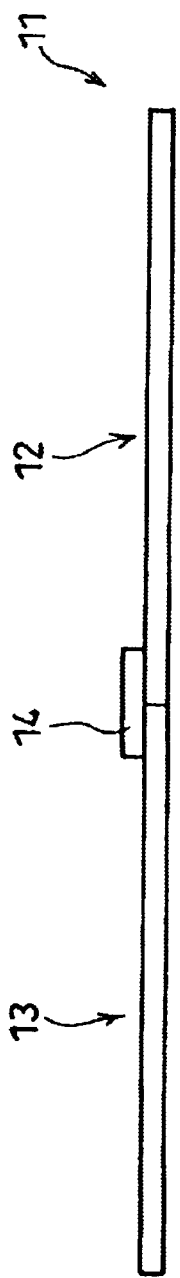
FIG.7(a)
FIG.7(b)

ANTIMICROBIAL AGENTS

This application is a 371 of PCT/JP99/03245, filed on Jun. 18, 1999.

FIELD OF THE INVENTION

The present invention relates to an antimicrobial agent, detergent, laundry supplement, disposable sheets, and disposable sheet set, and a producing method of the antimicrobial agent, and an antimicrobial treatment method. Particularly, the invention relates to an antimicrobial agent used to apply antimicrobial treatment such as disinfection (sterilization), deodorizing, mildew proofing, and sanitization on target objects such as houses, hospitals, public facilities, industrial products, industrial wastes, and home appliances, and a producing method of such an antimicrobial agent, and an antimicrobial treatment method for treating the target objects with the antimicrobial agent, and the invention also relates to a detergent and laundry supplements used to wash fiber products of, for example, clothes, bedding, and medical use among various other products, and an antimicrobial treatment method for treating target objects such as these fiber products, and also disposable sheets and a disposable sheet set suitable for use in beds of permanently-ill patients.

BACKGROUND OF THE INVENTION

In recent years, in-hospital infections by MRSA (Methicillin-resistant *Staphylococcus aureus*), or infections by the enteropathogenic bacteria *Escherichia coli* (O-157) and other bacteria have become such a serious social problem that there is strong need for counter-measures against these infections. Further, with increase in number of air-tight housing, such as apartments, there has been high demand for mildew proofing in places where humidity is high, such as bathrooms.

Conventionally, for disinfection to prevent infections in hospitals and houses, it has been common practice to adopt chlorine-containing disinfectants such as sodium hypochlorite, sodium chlorite, sodium dichloroisocyanurate, and sodium trichloroisocyanurate, or quaternary ammonium salts such as benzalkonium chloride.

In particular, chlorine-containing disinfectants have such superior properties as demonstrating the disinfecting effect on eumycetes and various species of bacteria except tubercle bacillus, having wide disinfecting spectrum and thus can deactivate viruses, having immediate effect, preventing resistant bacteria, capable of oxidative decomposition of odor components in addition to and at the same time as disinfection, and converting itself after decomposition to sodium chloride or urea which is safe, and thus the chlorine-containing disinfectants have been most commonly used among other disinfectants.

However, the chlorine-containing disinfectants have such drawbacks as not showing the residual effect, and failing to inhibit proliferation of air-borne microbes which were newly introduced after the treatment, which necessitated repeating the treatment quite often. Further, with regard to the quaternary ammonium salts, while their disinfecting properties are similar to that of the chlorine-containing disinfectants, they are incapable of decomposing odor components and react with common anionic surfactants and deactivate itself, and thus had the problem of limited use compared with the chlorine-containing disinfectants.

Meanwhile, conventionally used antimicrobial agents having a long-term and sustained effect on bacteria and molds have incorporated ions of heavy metals such as zinc, silver, and copper. The heavy metal ions have such properties as having a wide disinfecting spectrum, showing strong disinfecting effect in particular on bacteria, having long-term and sustained antimicrobial effect, and preventing resistant bacteria. As such heavy metal ions, silver ion has been widely used recently since it is superior especially in safety.

However, the silver ion is insufficient compared with oxidizing agents such as chlorine-containing disinfectants when it comes to disinfecting effect and deodorizing effect immediately after the treatment, and in order to effect the mildew proofing properties, the silver ion needs to have a higher concentration than the case for bacteria. There is a further problem in silver ion in that when sulfides exist in the target object (object to be treated), the silver ion converts itself to sulfide which is water insoluble, with the result that the antimicrobial effect suffers significantly in subsequent treatment.

In view of these drawbacks, the inventors of the present invention studied to develop antimicrobial agents having a wide disinfecting spectrum, capable of preventing resistant bacteria, having good safety, having both immediate and residual effects with respect to disinfection as well as deodorizing, and having good resistance for the sulfide, by combining the oxidizing agents having the immediate effect and the silver ion having the residual effect.

According to the study by the inventors of the present invention, the silver ion, when combined with the oxidizing agents, preferably exists in the aqueous solution state. The silver ion may be kept in the solution state by conventionally known methods such as turning silver ion into complex salts of thiosulfate or thiocyanate, or into silver salts of amino acids. However, the anionic ions of thiosulfate, thiocyanate anion, or amino acids, when mixed with the oxidizing agents, are decomposed by the oxidizing effect of the oxidizing agents with the result that the active ingredient, the silver ion, precipitates as hydroxides, which prevented the complex salt of silver thiosulfate, thiocyanate complex salt of silver, and silver salts of amino acids from being mixed with the oxidizing agents.

Further, in recent years, there have been proposed many fiber products such as clothes and other various bacteria-proof products which have been subjected to the antimicrobial treatment (including sanitization and sterilization). Generally, these bacteria-proof products come to have antimicrobial properties by the solid (powder) antimicrobial agents which are pre-fixed on the surface and elsewhere of the fiber products. As such solid antimicrobial agents, organic antimicrobial agents which are hardly soluble in water, or hardly water-soluble compounds of metals such as silver having antimicrobial properties have been used.

Meanwhile, liquid or water-soluble antimicrobial agents have been put to practical applications as well. As such liquid or water-soluble antimicrobial agents, alcohols, phenols such as cresol, and quaternary ammonium salts, as well as complex salts of antimicrobial metal such as silver salts of amino acid, thiosulfate, and thiocyanate have been used.

However, the bacteria-proof products (fiber products, etc.) which were treated with the conventional antimicrobial agent lose their antimicrobial properties when their surface is covered with dirt, etc. Further, when silver compounds are used as the antimicrobial agent, the antimicrobial properties are lost when the silver is sulfidized.

Also, the conventional solid antimicrobial agent needs to be fixed on the surface and elsewhere of the products by pre-kneading or other special treatment. Thus, once the antimicrobial properties of the product are lost, for example, by dirt or sulfidization of the silver, an industrial-scale treatment technique is required to recover the antimicrobial properties by treating the product again. Thus, with the antimicrobial treatment method by the conventional solid antimicrobial agent, it was difficult to sustain the antimicrobial properties of the bacteria-proof products or recover the antimicrobial properties by re-treatment of the products conveniently at home.

In contrast, the conventional liquid or water-soluble antimicrobial agents have the advantage that the antimicrobial properties can be effected by directly applying the agents on the surface of the products in use. However, these liquid or water-soluble antimicrobial agents applied on the surface of the fiber products completely dissolve into water by washing and the antimicrobial properties are easily lost.

Further, the antimicrobial agents of alcohols or phenols have the problem that a sustained antimicrobial effect cannot be obtained since they are volatile and easily oxidized. Also, the antimicrobial agent of alcohols in particular are highly inflammable, and the antimicrobial agent of phenols are very toxic and has strong irritating odor, and therefore they have the problem of safety. Further, the antimicrobial agent of quaternary ammonium salts has the drawback that the antimicrobial ability is easily lost by reacting with an anionic surfactant which exists in a common detergent.

Further, the thiosulfate complex salt and thiocyanate complex salt of silver include sulfide ion ($S^{2-}$) in the complex salt, and generate toxic gas when decomposed by acid or heat, and the complex salt as the active ingredient gradually converts itself to silver sulfide, thus losing the antimicrobial ability.

Incidentally, the thiosulfide complex salt of silver, thiocyanate complex salt of silver, and amino acid salt of silver are decomposed in the presence of alkaline oxidizing agents such as sodium hypochlorite by the oxidizing effect of the sodium hypochlorite, etc. Thus, the conventional silver-containing antimicrobial agents utilizing the complex salts of silver could not be used with so-called chlorine-containing bleaching agents containing the alkaline oxidizing agents such as sodium hypochlorite.

Further, the organic complex salts such as amino acid salts of silver have relatively low complex stability compared with inorganic complex salts including sulfide ion ($S^{2-}$). Thus, the silver chloride tends to form precipitates during storage by the reaction with surrounding chlorine ions with the result that the antimicrobial properties suffer significantly. Also, the precipitates of the silver chloride thus formed gradually increase in size during storage of the detergent, etc. Such precipitates of the silver chloride have poor solubility and are not dispersed homogeneously, and thus do not have the property of being absorbed onto the surface of the products. Thus, the precipitates of the silver chloride which are formed by the reaction of the organic complex salts such as amino acid salts of silver with the surrounding chlorine ions hardly contribute to effect the antimicrobial properties. Further, these organic complex salts may blacken in the same manner as inorganic silver slats and may result in change in color of the fiber products.

Incidentally, in order to eliminate the inconvenience of washing sheets, disposable sheets have been used for the sheets of beds of permanently-ill patients.

However, conventional disposable sheets are realized by the use of inexpensive raw materials such as paper or unwoven fabric, and while this may eliminate the inconvenience of washing the sheets, the inconvenience of replacing the sheets could not be eliminated. The conventional disposable sheets necessitated a permanently-ill patient to be moved from the bed to replace the sheets. Thus, replacement of the conventional disposable sheets generally required a plurality of care givers and it was very difficult to replace the sheets by a single care giver. Therefore, there were cases where the disposable sheets could not be replaced even when it was urgently needed due to dirt on the sheet because there was only one care giver.

Accordingly, there is demand for disposable sheets which can be replaced by a single care giver.

DISCLOSURE OF INVENTION

The present invention was made in the light of the foregoing problems and it is the first object of the present invention to provide an antimicrobial agent in which oxidizing agents and silver ion coexist, and which has a wide disinfecting spectrum, prevents resistant bacteria, has good safety, shows high resistance to sulfides, and has both immediate and residual properties for disinfection as well as deodorizing, and to provide a producing method thereof, and an antimicrobial treatment method using such an antimicrobial agent.

In order to achieve the first object, a first antimicrobial agent in accordance with the present invention includes silver-chloro complex salts and oxidizing agents.

With this constitution, it is possible to provide an antimicrobial agent having both immediate and residual properties for disinfection and deodorizing, having a wide disinfecting spectrum, capable of preventing resistant bacteria, having good safety, capable of maintaining sufficient stability even in a medium or environment in which sulfides coexist, and having a reasonable price, and having superior deodorizing action and antimicrobial and mildew proofing action.

It is preferable that the first antimicrobial agent in accordance with the present invention includes the silver-chloro complex salts and oxidizing agents in an aqueous solution of chlorides, and the concentration of the silver-chloro complex salts in the aqueous solution of chlorides is not less than 0.05 mg/l in silver ion equivalent concentration. This allows the antimicrobial agent to demonstrate the antimicrobial action sufficiently.

The concentration of the silver-chloro complex salts in the aqueous solution of the chlorides is preferably not less than 2.5 mg/l in silver ion equivalent concentration. As a result, it is possible to obtain superior antimicrobial action even in the presence of organic substances which contain sulfur in the form of sulfides.

The concentration of the chloride ion in the aqueous solution of the chlorides is preferably not less than 0.02 mol/l. As a result, the silver ion concentration of not less than 2.5 mg/l can be realized. Thus, superior antimicrobial action can be obtained even in the presence of organic substances which contain sulfur in the form of sulfides.

The oxidizing agents are preferably sodium hypochlorite and/or sodium chlorite. As a result, the immediate property of the antimicrobial agent can further be improved.

Further, in order to achieve the first object, a producing method of the first antimicrobial agent in accordance with the present invention is adapted to mix an aqueous solution of chlorides, silver and/or silver compound, and oxidizing agents.

With this method, it is possible to provide a producing method of the antimicrobial agent having both immediate and residual properties for disinfection and deodorizing, having a wide disinfecting spectrum, capable of preventing resistant bacteria, having good safety, capable of maintaining sufficient stability even in a medium or environment in which sulfides coexist, and having a reasonable price, and having superior deodorizing action and antimicrobial and mildew proofing action.

Further, in order to achieve the first object, a first antimicrobial treatment method in accordance with the present invention is adapted to treat a target object using an aqueous solution containing the silver-chloro complex salts in the presence of the oxidizing agents.

With this method, it is possible to provide an antimicrobial treatment method having both immediate and residual properties for disinfection and deodorizing, having a wide disinfecting spectrum, capable of preventing resistant bacteria, having good safety, capable of maintaining sufficient stability even in a medium or environment in which sulfides coexist, and having a reasonable price, and having superior deodorizing action and antimicrobial and mildew proofing action.

It is the second object of the present invention to provide an antimicrobial agent and an antimicrobial treatment method which can be used conveniently at the concentration of preservation, and which does not result in rusting or deposition of salts, and which has the immediate property as well as cleansing ability.

In order to achieve the second object, a second antimicrobial agent in accordance with the present invention includes the silver-chloro complex salts and chloride for supplying chloride ion, and further compounds having compatibility with the solvent which dissolves the chloride. The second antimicrobial agent preferably further includes the solvent which dissolves the chloride. Further, the solvent is preferably water.

With this constitution, the compounds having compatibility with the solvent which dissolves the chloride capture water or other solvents, and accordingly it is possible to reduce the free water or solvent which is not chemically and physically captured in the vicinity of the silver-chloro complex salts in the antimicrobial agent solution. As a result, it is possible to increase the apparent concentration of the chloride ion which contribute to stability of the silver-chloro complex salts. Thus, the concentration of the chloride ion actually contained in the antimicrobial agent solution can be reduced while maintaining the apparent concentration of the chloride ion which is directly required to stabilize the silver-chloro complex salts. As a result, the antimicrobial treatment can be effected easily without diluting the antimicrobial agent solution in use.

The compounds having compatibility with the solvent which dissolves the chloride are preferably alcohol. The alcohol captures water, etc., and satisfies the immediate property, and thus it is possible to reduce the concentration of the chloride ion, and, at the same time, effect the immediate property for the antimicrobial agent.

The compounds having compatibility with the solvent which dissolves the chloride may alternatively be surfactants. The surfactants capture water, etc., and satisfies the cleansing ability, and thus it is possible to reduce the concentration of the chloride ion, and, at the same time, obtain the cleansing ability for the antimicrobial agent.

In order to achieve the second object, a second antimicrobial treatment method in accordance with the present invention is adapted to treat the target object with the second antimicrobial agent.

With this method, it is not required to change the preservation concentration of the chloride ion in use, thus effecting the antimicrobial treatment conveniently.

It is the third object of the present invention to provide an antimicrobial agent which can effectively demonstrate the antimicrobial properties without spoiling the appearance or feel of the target object due to formation of crystals such as white crystals on the surface of the target object after the antimicrobial treatment and even when the target object is a liquid, or, for example, has a complicated surface structure such as fine voids.

In order to achieve the third object, a third antimicrobial agent in accordance with the present invention includes a chloride which has at least one of (I) the property capable of existing as a supersaturated aqueous solution for 24 hours or longer in the presence of a crystal nucleus at least at room temperature, and (II) the property capable of being decomposed when dissolved in water, and the silver-chloro complex salts.

With this constitution, by the chloride having at least one of the foregoing properties, there will be no crystallization of the deposited chloride even when the antimicrobial agent is dried and the chloride is concentrated, and the chloride stably exists, for example, as the residue of a transparent and irregular form in the super saturated state. Thus, the appearance or feel of the target object will not be spoiled by the white crystals, etc., of the chloride on the surface of the target object.

The chloride is preferably polyaluminium chloride. Polyaluminium chloride has the property of forming colloid hydroxides in an aqueous solution. The colloid hydroxides absorb silver chloride and disperse it in the aqueous solution, and thus fine particles of the silver chloride which demonstrates the antimicrobial properties can be localized in the aqueous solution. As a result, by using the polyaluminium chloride as the chloride, it is possible to provide, when the target object is, for example, a liquid such as foul water or waste fluid, an antimicrobial agent having improved antimicrobial properties than the conventional antimicrobial agents which contain ammonium chloride, or chlorides of alkali metal or alkali earth metal.

The chloride may alternatively be organic compounds. This allows the surface tension of the antimicrobial agent solution to be reduced compared with the conventional antimicrobial agents which contain ammonium chloride, or chlorides of alkali metal or alkali earth metal, thereby increasing the permeability of the antimicrobial agent solution with respect to the target object. As a result, it is possible to provide an antimicrobial agent which can effectively demonstrate the antimicrobial properties for target objects having a complicated surface structure such as fine voids.

The organic compounds are preferably cationic surfactants, and benzalkonium chloride is particularly preferable. This allows the surface tension of the antimicrobial agent solution to be further reduced, thus further increasing the permeability of the antimicrobial agent solution with respect to the target object. As a result, it is possible to provide an antimicrobial agent which can demonstrate the antimicrobial properties further effectively with respect to target objects having a complicated surface structure such as fine voids. Further, since benzalkonium chloride has the antimicrobial properties of superior immediate action, i.e., superior disinfecting ability, it is possible to provide an antimicrobial agent with the immediate property.

It is the fourth object of the present invention to provide an antimicrobial agent and a producing method thereof having wide use, for example, such as mixing with a powder such as a powder detergent, or kneading with resin or fiber in the form of fine particles.

The inventors of the present invention have found, in the course of its completion, a solid antimicrobial agent and a producing method thereof which can stably demonstrate antimicrobial properties.

In order to achieve the fourth object, a fourth antimicrobial agent in accordance with the present invention includes silver-chloro complex salts and chloride for supplying the chloride ion, and is a solid.

With this constitution, since the antimicrobial agent is a solid, it is possible to provide an antimicrobial agent having wide use, for example, such as mixing with a powder such as a powder detergent, or kneading with resin or fiber, etc., in the form of fine particles. Further, by the silver-chloro complex salts having the sustained antimicrobial property and by the chloride which stabilizes the silver-chloro complex salts, it is possible to provide an antimicrobial agent having stable antimicrobial properties.

In order to achieve the fourth object, a producing method of the fourth antimicrobial agent in accordance with the present invention includes the steps of preparing a mixture by mixing silver and/or silver compound, and the chloride for supplying chloride ion, and water, and removing water from the mixture.

With this constitution, since the mixture contain the chloride, the silver-chloro complex salts exist stably even when water is removed from the mixture. As a result, the solid antimicrobial agent having stable antimicrobial properties can be produced. Thus, it is possible to provide a producing method of the antimicrobial agent having wide use, for example, such as mixing with a powder such as a powder detergent, or kneading with resin or fiber, etc., in the form of fine particles. Further, by the sustained antimicrobial property of the silver-chloro complex salts formed in the mixture, and by the chloride which stabilizes the silver-chloro complex salts, it is possible to provide a producing method of the antimicrobial agent having stable antimicrobial properties.

It is the fifth object of the present invention to provide a detergent and laundry supplement which can conveniently effect the antimicrobial treatment with the sustained property without resulting in change in color of the target object, and to provide an antimicrobial treatment method which can conveniently effect the antimicrobial treatment with the sustained property without resulting in change in color of the target object.

After extensive research to achieve this object, the inventors of the present invention have found in the course of its completion that the foregoing object can be achieved by adding the silver-chloro complex salts in the a cleansing solution liquid (solution) when washing, for example, fiber products, etc.

That is, in order to achieve the fifth object, the detergent in accordance with the present invention includes the silver-chloro complex salts.

With this constitution, by the antimicrobial ability of the silver-chloro complex salts, the antimicrobial treatment can be effected on a washing target object (target object) without resulting in change in color of the washing target object. Further, since the silver-chloro complex salts which are diluted in the cleansing solution form fine particles of the silver chloride and are absorbed on the surface of the washing target object, the sustained antimicrobial property can easily be effected in laundry.

Further, with this constitution, since the silver-chloro complex salts are stable with respect to acid or heat, and do not react with ingredients of the detergent, for example, such as the anionic surfactant, and thus can stably sustain the antimicrobial ability, it is possible to perform washing and antimicrobial treatment at the same time. Further, by the antimicrobial ability of the silver-chloro complex salts, antiseptic effect can be obtained for the detergent.

Note that, the detergent preferably has the washing action by including a surfactant.

In order to achieve the fifth object, the laundry supplement in accordance with the present invention includes the silver-chloro complex salts.

With this constitution, when the silver-chloro complex salts include, for example, softening agents, it is possible to effect a softening property, and at the same time, the antimicrobial treatments on the washing target object (target object) by the antimicrobial ability of the silver-chloro complex salts without resulting in change in color of the washing target object. Further, since the silver-chloro complex salts which are diluted in the cleansing solution form fine particles of the silver chloride and are absorbed on the surface of the washing target object, it is possible to obtain the sustained antimicrobial property conveniently when effecting the softening property, etc. Further, with the foregoing constitution, since the silver-chloro complex salts are stable with respect to acid or heat, and do not react with ingredients of the laundry supplement, for example, such as the anionic surfactant, and thus can stably sustain the antimicrobial ability, it is possible to effect the softening property, etc., and the antimicrobial treatment at the same time. Further, by the antimicrobial ability of the silver-chloro complex salts, antiseptic effect can be obtained for the laundry supplement.

The laundry supplement preferably further includes a bleaching agent. By the oxidizing effect of the bleaching agent included in the laundry supplement, the silver-chloro complex salts do not lose its antimicrobial ability. Thus, with this constitution, it is possible to provide a laundry supplement which employs both bleaching agent and antimicrobial agent. Note that, the bleaching agent is preferably hypochlorite and/or chlorite.

In order to achieve the fifth object, a third antimicrobial treatment method in accordance with the present invention is adapted to treat the target object in a solution which contains the silver-chloro complex salts.

With this constitution, by the antimicrobial ability of the silver-chloro complex salts, it is possible to conveniently effect the antimicrobial treatment without resulting in change in color of the target object. Further, since the silver-chloro complex salts which are diluted in the treatment liquid form fine particles of the silver chloride and are absorbed on the surface of the target object, the antimicrobial effect on the target object can easily be sustained.

The solution is preferably a cleansing solution containing the surfactant. By using such a cleansing solution, the target object can be subjected to the antimicrobial treatment as well as washed.

Further, the third antimicrobial treatment method has the prominent effect of preventing change in color of fiber products when the target object is fiber products.

It is the sixth object of the present invention to provide disposable sheets which can be removed while a person is lying thereon, and a disposable sheet set which allows a single care giver to replace the disposable sheets when it is used for beds of permanently-ill patients.

In order to achieve the sixth object, the disposable sheets in accordance with the present invention include notches with respect to and in the longitudinal direction of rectangular sheets so that the sheets can be separated into two, and a tape for sealing the notches, which is stuck on the sheets by a pressure sensitive adhesive agent covering the notches.

With this arrangement, the sheets can be removed only by moving the sheets while a person lying thereon. That is, for example, a person lying on the disposable sheets is moved to the right side of the sheets, and then after peeling off the tape, by pulling the left side of the sheets with hands, the sheets are separated at the notches, removing the left side of the sheets. Then, the person lying on the sheets is moved to a portion from which the left side of the sheets was removed, and the right side of the sheets is pulled to remove the right side of the sheets.

Thus, with the foregoing arrangement, by placing another sheets in advance under the disposable sheets, the sheets can be replaced while the person is lying thereon, and therefore, when used for beds of permanently-ill patients (simply "patients" hereinafter), it is not required to move the patient from the bed and the sheets can be removed by a single care giver.

Further, with the foregoing arrangement, since the notches are sealed by the tape, it is possible to prevent urine or sweat, etc., of the person (e.g., patient) lying thereon from seeping out into the underlying sheets, for example, another disposable sheets, through the notches in use.

Note that, as the phrase is used herein, "notches which allow the sheets to be separated from each other" is meant to indicate those notches which allow the sheets to be separated into two along the notches by being pulled with hands. Also, "notches" not only indicate slits, i.e., a long narrow opening, but a sewing pattern, i.e., perforations in the form of a dotted line.

In order to achieve the sixth object, the disposable sheets in accordance with the present invention include two rectangular sheet elements which are disposed side by side with their longer sides adjoining each other, and a tape which is attached on the sheet elements by a pressure sensitive adhesive agent so as to cover a portion of the sheet elements in contact with each other.

With this arrangement, the sheet elements can be removed only by moving the sheet elements while a person lying thereon. That is, for example, a person lying over the two sheet elements is moved to the right side of the sheet elements and the tape is peeled off, thus allowing the left side of the sheet elements to be removed by pulling it with hands. Then, the person lying on the disposable sheets is moved to a portion from which the left side of the sheet elements was removed, thus allowing the right side of the sheet elements to be removed by pulling it with hands.

Thus, with the foregoing arrangement, by placing another sheets in advance under the disposable sheets, the sheets can be replaced while the person is lying thereon, and therefore, when used for beds of permanently-ill patients, it is not required to move the patient from the bed and the sheets can be removed by a single care giver.

Further, with the foregoing arrangement, since the portion where the sheet elements are in contact with each other is sealed by the tape, urine or sweat, etc., of the person (e.g., patient) lying thereon can be prevented from seeping out into the underlying sheets, for example, another disposable sheets, through the gap between the sheet elements.

The disposable sheets having the foregoing arrangement preferably further include the antimicrobial and deodorizing agent and a polymer water absorbent. As a result, the antimicrobial and deodorizing effect can be obtained by the antimicrobial and deodorizing agent. Further, by the polymer water absorbent, it is ensured that the urine or sweat, etc., can be absorbed, thus surely preventing urine or sweat, etc., from seeping out through the disposable sheets. As a result, clean environment can be maintained.

Note that, as the term is used herein, "antimicrobial and deodorizing agent" refers to those additives which have both antimicrobial action and deodorizing action.

The disposable sheets of the foregoing arrangements preferably include the solid silver-chloro complex salts. As a result, it is possible to obtain the antimicrobial and deodorizing action with a superior sustained (residual) property for the disposable sheets.

In order to achieve the sixth object, the disposable sheet set in accordance with the present invention has the disposable sheets of the foregoing arrangements, any of which are stacked one over another.

With this arrangement, once placed on the bed of a permanently-ill patient, the disposable sheets can be replaced only by moving the sheets while the patient lying thereon. Thus, it is not required to move the patient from the bed and the disposable sheets can be replaced only by a single care giver.

BRIEF DESCRIPTION OF THE DRAWINGS

FIGS. 2(*a*) and 2(*b*) are drawings which show one embodiment of disposable sheets of the present invention, in which FIG. 2(*a*) is a perspective view, and FIG. 2(*b*) is a side view.

FIGS. 7(*a*) and 7(*b*) are drawings which show another embodiment of disposable sheets of the present invention, in which FIG. 7(*a*) is a perspective view, and FIG. 7(*b*) is a side view.

PREFERRED EMBODIMENTS OF THE PRESENT INVENTION

Figure 1:
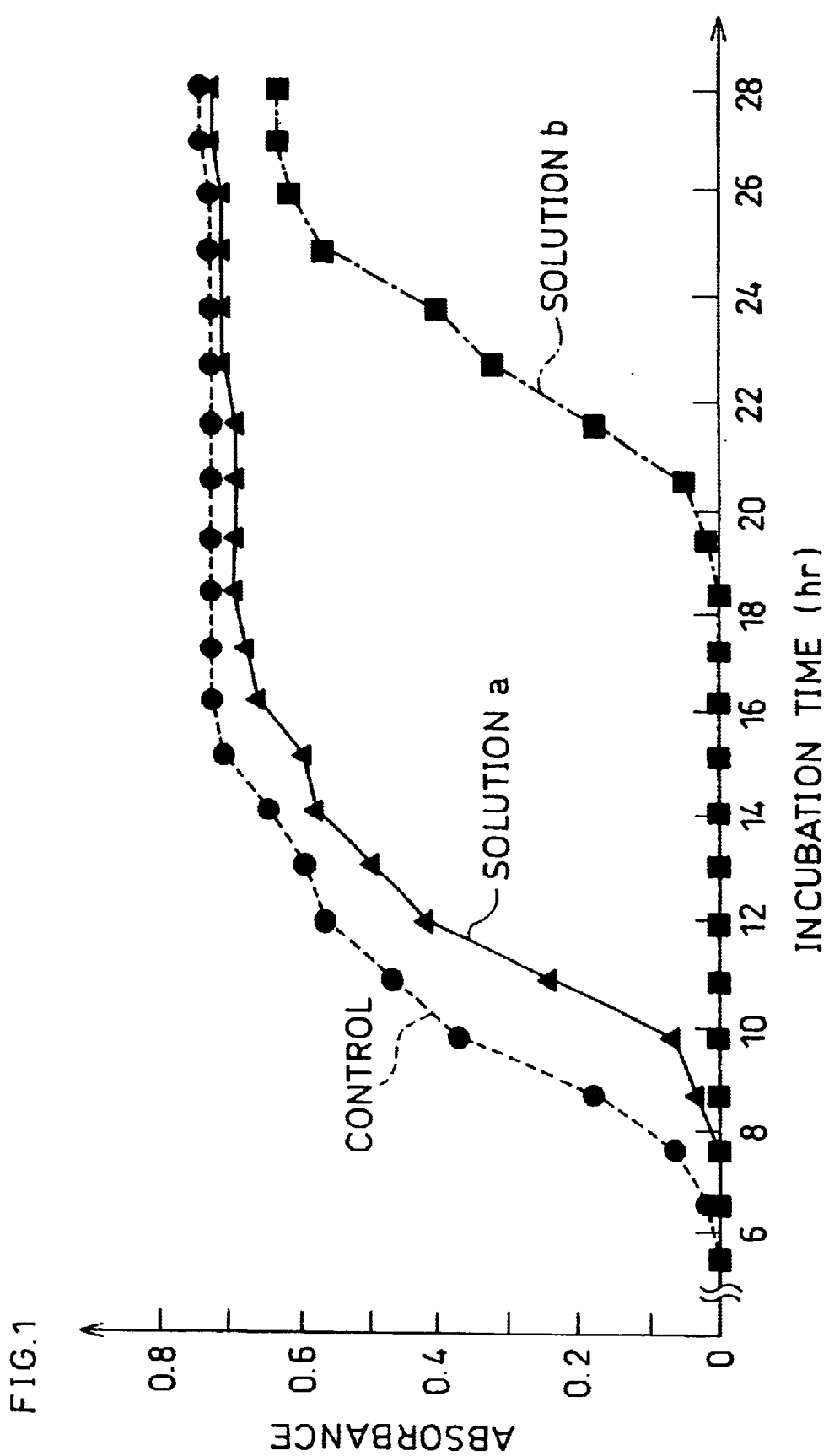
FIG. 1 is a graph which shows a relationship between incubation time and proliferation of bacteria (indicated by absorbance) in a growth test of *Escherichia coli* in a medium containing sulfides of Example 3.

The following will describe in detail a first antimicrobial agent, a producing method of the first antimicrobial agent, and a first antimicrobial treatment method.

The first antimicrobial agent in accordance with the present invention includes a silver-chloro complex salts and oxidizing agents.

Note that, in the present invention, "silver-chloro complex salts" indicates salts with a complex ion structure as represented by the following structural formula (1).

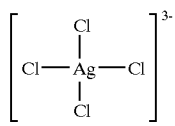

(1)

The antimicrobial agent may be an aqueous solution containing the silver-chloro complex salts an oxidizing agents (referred to as "antibacterial agent aqueous solution" hereinafter where distinction is necessary), or may be a mixture containing solid chlorocomplex salt and solid oxidizing agents. Note that, even though the following explanation is based mainly on the antimicrobial agent in the form of an aqueous solution, the same effect can be expected with the mixture of the solid chlorocomplex salt and the solid oxidizing agents.

In the antimicrobial agent, the silver ion is stabilized in the form of a chlorocomplex salt (silver-chloro complex salt) so that it can coexist with the oxidizing agents. That is, the antimicrobial agent is adapted to stabilize the silver ion in the form of the chlorocomplex salt so that the silver ion can coexist with the oxidizing agents in the aqueous solution without precipitation of the silver ion.

The silver-chloro complex salts are stabilized with chloride ion of high concentration. Thus, the antimicrobial agent preferably includes a chloride for supplying chloride ion, in addition to the silver-chloro complex salts and oxidizing agents. Accordingly, the antimicrobial agent aqueous solution preferably includes silver ion as the chlorocomplex salt and the oxidizing agents in a chloride aqueous solution.

The Chloride for supplying the chloride ion is not particularly limited and includes: chlorides (chlorides of alkali metals) having counter ions of alkali metal ions such as lithium ion, sodium ion, and potassium ion; chlorides having counter ions of alkali earth metal ions such as magnesium ion and calcium ion; aliphatic quaternary ammonium salts, such as aliphatic quaternary ammonium chloride having one or two alkyl groups of a long chain with 12 to 18 carbon atoms, tetramethylammonium chloride, and tetraethylammonium chloride; polyamine hydrochlorides, such as ethylenediamine hydrochloride, hexamethylenediamine hydrochloride, and hexamethylenetriamine hydrochloride; primary amine hydrochlorides, such as methylamine hydrochloride and ethylamine hydrochloride; secondary amine hydrochlorides, such as dimethylamine hydrochloride and diethylamine hydrochloride; tertiary amine hydrochlorides, such as trimethylamine hydrochloride and triethylamine hydrochloride; aromatic amine hydrochlorides, such as pyridine hydrochloride and aniline hydrochloride; aromatic quaternary ammonium salts, such as triethyl benzyl ammonium chloride, benzalkonium chloride, benzethonium chloride, pyridinium chloride, and imidazolinium chloride.

In the case where an alkaline oxidizing agents such as sodium hypochlorite are used to coexist as the oxidizing agents, it is particularly preferable that the chloride for supplying chloride ion is a chloride which does not precipitate by generating hydroxides even in the alkaline aqueous solution, i.e., more specifically, chlorides of alkali metals, such as sodium hydroxide and potassium hydroxide.

Unlike thiocyanate complex salt, thiosulfate complex salt, and silver salts of amino acids, the silver-chloro complex salts do not precipitate into silver hydroxide by being oxidized and decomposed by the alkaline oxidizing agents such as sodium hypochlorite. Further, in the case where the chloride for supplying chloride ion is contained, because the silver-chloro complex salts are stabilized by the chloride ion, the silver-chloro complex salts do not precipitate by producing silver chloride with the coexisting chloride ion even when the chlorine-containing oxidizing agents is used.

Further, it is well known that silver ion converts itself to silver sulfide and loses its antimicrobial activity in the presence of sulfur or sulfides. However, with the first antimicrobial agent in accordance with the present invention in which the oxidizing agents coexist with the silver ion, sulfur or sulfides can be oxidized even when it is present, thus preventing forming silver sulfide. Therefore, the first antimicrobial agent in accordance with the present invention can be used for antimicrobial treatment in places where sulfur or sulfides are present, which was not possible with the conventional silver antimicrobial agents.

The oxidizing agents used in the first antimicrobial agent in accordance with the present invention are not particularly limited but chlorite and/or hypochlorite are suitable since they are inexpensive, colorless, sufficiently stable as the aqueous solution for several months, and superior particularly in their immediate properties. Further superior immediate property can be expected with the hypochlorite. On the other hand, the chlorite has the pH in the neutral range and thus has a characteristic which allows a wide selection of metal ions which can be mixed, and a characteristic which is more stable with respect to decomposition than the hypochlorite. Further, the chlorite is preferably sodium chlorite in particular, and the hypochlorite is preferably sodium hypochlorite in particular.

Note that, even though many oxidizing agents have the property wherein the content is reduced by self-decomposition, since the silver-chloro complex salts do not promote decomposition of the oxidizing agents, the stability of the oxidizing agents can be maintained with the silver-chloro complex salts.

The antimicrobial action of the first antimicrobial agent in accordance with the present invention is sufficiently demonstrated by including the silver ion in not less than 0.05 mg/l in the chloride aqueous solution. Thus, the concentration of the silver-chloro complex salts in the aqueous solution is preferably not less than 0.05 mg/in silver ion equivalent concentration.

However, in the case where there exists an organic substance including sulfur in the form of sulfides, since a slight amount of silver is consumed as silver sulfide even in the presence of the oxidizing agents, it is further preferable to include the silver ion as the chlorocomplex salt in the amount of not less than 2.5 mg/l. That is, the antimicrobial action is relatively poor when the concentration of the silver ion is less than 2.5 mg/l, and it is preferable for use in antimicrobial treatment of a target object (object to be treated) which does not contain sulfur in the form of sulfides. Thus, it is further preferable that the concentration of the silver-chloro complex salts in the aqueous solution is not less than 2.5 mg/in silver ion equivalent concentration.

Further, the concentration of the chloride ion in the aqueous solution may be suitably decided depending on the required concentration of the silver ion. For example, while the silver can be dissolved as the chlorocomplex ions when the concentration of the chloride ion is not less than 0.003 mol/l, in order to obtain the effective concentration of the silver ion of 2.5 mg/l or greater even in the presence of sulfides, the concentration of the chloride ion is preferably not less than 0.02 mol/l. Further, even though the concentration of the oxidizing agents in the aqueous solution may be set at an arbitrary concentration, the oxidizing agents are preferably used at various concentrations, for example, at a higher concentration as required when the target object includes a large amount of sulfur or sulfides.

As described, a preferable form of the first antimicrobial agent in accordance with the present invention includes as main components the oxidizing agents, the chlorocomplex salt of silver ion, and the chloride for stabilizing the chlorocomplex salt, and it may further include other additives such as a surfactant, fragrance, and pigment.

According to the producing method of the first antimicrobial agent in accordance with the present invention, the chloride aqueous solution, silver and/or silver compound, and oxidizing agents are mixed. Here, the silver indicates a silver metal (silver simple substance).

According to a particularly suitable producing method of the first antimicrobial agent, a chloride aqueous solution having a predetermined concentration is mixed with the silver and/or silver compound, and the silver ion in a predetermined concentration (preferably not less than 0.05 mg/) is dissolved as the chlorocomplex salt in the chloride aqueous solution, and a predetermined concentration of the oxidizing agents are dissolved in the chloride aqueous solution including the silver ion as the chlorocomplex salt. As a result, it is possible to obtain the antimicrobial agent in accordance with the present invention, i.e., the antimicrobial agent which includes a predetermined concentration of the silver ion as the chlorocomplex salt in the chloride aqueous solution together with the oxidizing agents.

Further, according to the first antimicrobial treatment method in accordance with the present invention, an aqueous solution including the silver-chloro complex salts, or, more preferably, the chloride aqueous solution including the silver-chloro complex salts is used in the presence of the oxidizing agents so as to treat a target object. The oxidizing agents may be mixed beforehand with the aqueous solution including the silver-chloro complex salts, or used together with the aqueous solution including the silver-chloro complex salts when treating the target object. That is, the target object may be treated using the antimicrobial aqueous solution in accordance with the present invention, i.e., the aqueous solution including the silver-chloro complex salts and the oxidizing agents, or, alternatively, the target object may be treated using the aqueous solution including the silver-chloro complex salts, together with the oxidizing agents. Further, the target object may be treated using an aqueous solution which is prepared by dissolving in water a solid antimicrobial agent, which is a mixture containing a solid chlorocomplex salt and solid oxidizing agents (preferably further with a solid chloride).

The antimicrobial agent aqueous solution in accordance with the present invention may be used in undiluted form (antimicrobial agent aqueous solution as prepared) to treat a target object, or, alternatively, the antimicrobial agent may be adapted to treat the target object with the undiluted solution and then wash the target object with water, or the target object may be treated after diluting the undiluted solution with water.

When treating the target object with the undiluted solution, the oxidizing agents demonstrate the immediate antimicrobial action, and the silver-chloro complex salts demonstrate the sustained antimicrobial action. In the method in which the target object is treated with the undiluted solution and then washed with water, the concentration of the chloride ion decreases in washing and the silver-chloro complex salts are fixed on the surface of the target object by converting itself to silver chloride which is hardly soluble. The silver chloride formed this way is in the form of ultra fine particles, and is dispersed and has a wide surface area. Therefore, the silver chloride thus prepared shows long-term strong antimicrobial activity and does not result in blackening, which is commonly seen when the silver chloride is formed. Thus, this method demonstrates the immediate antimicrobial action by the oxidizing agents, and the residual antimicrobial effect by the fine silver chloride. Further, in the method where the target object is treated after diluting the undiluted solution with water, the chlorocomplex salt of the silver ion is converted to the silver chloride when diluted, thus having the immediate antimicrobial action by the oxidizing agents and the residual antimicrobial action by the fine silver chloride, as in the case where the target object is water washed after treatment with the undiluted solution. Note that, in the method in which the target object is treated after diluting the undiluted solution with water, it is preferable that the concentration of the silver ion after dilution with water satisfies the foregoing conditions.

Referring to Examples, the following will describe the first antimicrobial agent, producing method of the first antimicrobial agent, and first antimicrobial treatment method in accordance with the present invention.

EXAMPLE 1

The present example examined stability of the antimicrobial agent solution.

Firstly, an antimicrobial agent solution (solution C) was prepared as the first antimicrobial agent in accordance with the present invention by mixing, in the volume ratio of 1:1, an aqueous solution (solution A) containing 35 percent by weight of sodium chloride and the silver-chloro complex salts in the silver ion concentration of 500 ppm with an aqueous solution (solution B) of sodium hypochlorite containing 137 g/l of effective chlorine. The concentration of the silver-chloro complex salts in the antimicrobial agent solution was about $3 \times 10^2$ mg/l in silver ion equivalent concentration.

These solutions A, B, and C were stored for 50 days under the condition of 30° C. and change in the amount of effective chlorine and change in solution state were measured for each solution. Table 1 shows the results of observation of the amount of effective chlorine (g/l) and the solution state at the start of the test (immediately after mixing) and after 50 days at 30° C., and also a remaining fraction of the effective chlorine (with respect to the initial amount of chlorine at 100% at the start of the test) after 50 days at 30° C. The results show that decline in effective chlorine was not facilitated even in the presence of the silver-chloro complex salts and preservation did not suffer. Further, it was found that the silver-chloro complex salts did not become unstable and did not precipitate by being mixed with the sodium hypochlorite.

TABLE 1

| SAMPLE SOLUTION | START OF TEST (IMMEDIATELY AFTER MIXING) | | | AFTER 50 DAYS AT 30° C. | | |
|---|---|---|---|---|---|---|
| | AMOUNT OF CHLORINE (g/l) | REMAINING FRACTION (%) | SOLUTION STATE | AMOUNT OF CHLORINE (g/l) | REMAINING FRACTION (%) | SOLUTION STATE |
| SOLUTION A | 0 | — | COLORLESS TRANSPARENT | 0 | — | COLORLESS TRANSPARENT |
| SOLUTION B | 137 | 100 | YELLOW TRANSPARENT | 103 | 75 | YELLOW TRANSPARENT |
| SOLUTION C | 67 | 100 | YELLOW TRANSPARENT | 56 | 84 | YELLOW TRANSPARENT |

EXAMPLE 2

The present Example examined antimicrobial effect on *Staphylococcus aureus*.

First, using the antimicrobial agent solution (solution C) of Example 1, antimicrobial effect on *Staphylococcus aureus* was evaluated. Further, as a control, the same evaluation was made using the sodium hypochlorite solution (solution B). The testing method is as follows.

A floor plate made of linoleum was cut into pieces of 10 cm×10 cm, which were then boiled for an hour four times in water including a neutral detergent so as to remove a plasticizer, etc. On these floor plates were independently sprayed the solution B diluted 200 times and the solution C diluted 100 times using a sprayer in the amount of 1 ml per floor plate. Spraying was repeated at predetermined intervals of four four patterns: everyday, every other day, every three days, and every six days. Also, on each floor plate was sprayed an inoculum of *Staphylococcus aureus* in the concentration of $10^2$ CFU (Colony Formation Unit)/ml on the daily basis in the amount of about 1 ml per floor plate. For the floor plates treated with the solution C, inoculation was made after the surface of the floor plates was dried after the solution treatment. On the 7th day of the experiment, an YP medium was sprayed on the floor plates, and the floor plates were incubated for 2 days under the conditions of 30° C. and 100% R.H. (Relative Humidity).

Table 2 shows the results.

TABLE 2

| TREATING SOLUTION | ELAPSED TIME FROM START OF EXPERIMENT (TREATMENT) IN DAYS | | | | | | PROLIFERATION OF BACTERIA |
|---|---|---|---|---|---|---|---|
| | DAY 1 | DAY 2 | DAY 3 | DAY 4 | DAY 5 | DAY 6 | |
| NONE | — | — | — | — | — | — | ++ |
| SOLUTION B | ○ | ○ | ○ | ○ | ○ | ○ | + |
| SOLUTION B | ○ | — | ○ | — | ○ | — | + |
| SOLUTION B | ○ | — | — | ○ | — | — | + |
| SOLUTION B | ○ | — | — | — | — | — | ++ |
| SOLUTION C | ○ | ○ | ○ | ○ | ○ | ○ | - |
| SOLUTION C | ○ | — | ○ | — | ○ | — | - |
| SOLUTION C | ○ | — | — | ○ | — | — | - |
| SOLUTION C | ○ | — | — | — | — | — | + |

In Table 2, "NONE" under the column of treating solution indicates no treatment. The symbol "○" indicates spraying of the treating solutions, and "–" under the column of elapsed time from the start of the experiment (treatment) in Table 2 indicates no spraying of the treating solutions. Also, under the column of proliferation of bacteria in Table 2, the symbol "++" and "+" indicate the number of colonies per floor plate in the order of several hundreds ($10^2$ to $10^3$) and several tens (10 to $10^2$), respectively, and "–" indicates no colony.

As can be seen from Table 2, the solution B containing only sodium hypochlorite did not show the residual effect for *Staphylococcus aureas*, whereas the solution C which was diluted to contain the same amount of effective chlorine showed the residual effect for 2 days.

EXAMPLE 3

The present example compared a growth rate of bacteria using the antimicrobial agent in accordance with the present invention and a comparative antimicrobial agent which did not include the oxidizing agents.

Firstly, a silver-chloro complex salt solution (solution a) was prepared as the comparative antimicrobial agent by dissolving 35 g of calcium chloride and 0.05 g of silver chloride in 100 ml of water. Also, an antimicrobial agent solution (solution b) was prepared as the first antimicrobial agent in accordance with the present invention by adding 3 parts by volume of a 4.3 percent by weight solution of sodium hypochlorite with respect to 7 parts by volume of the solution a.

Then, the Trypto-Soya Broth "Nissui" (TSB) medium (provided by NISSUI PHARMACEUTICAL Co., Ltd.) was adjusted to have a pH of 7.2 and was sterilized for 15 minutes at 121° C. and divided into two equal parts. To each of the two parts was added the solution a or solution b in the amount of 0.1 percent by weight (0.5 mg/l of solution a and 0.35 mg/l of solution b in Ag ion equivalent concentration).

Each TSM medium of the solution a or solution b was inoculated with 20 µl of a 100 times diluted inoculum of pre-incubated *Escherichia coli* (species: *Escherichia coli* MC1061), and was incubated for 28 hours at 37° C. During incubation, absorbance with respect to the light of 660 nm was measured for every 60 minutes using a spectrophotometer (provided by Shimadzu Corporation:product name (Shimadzu SP-20A)), and the growth curve as shown in FIG. 1 was obtained. Note that, "CONTROL" indicates the result of measurement using a cultured medium which was incubated as above but without inoculating the strain.

The TSB medium includes proteins which contain sulfur in the form of sulfides, such as peptone and soybean peptone. As can be seen in FIG. 1, while the bacteria start to proliferate after 6 hours in the control, proliferation of bacteria is inhibited for 8 hours with the solution a and for 19 hours with the solution b.

EXAMPLE 4

The present example examined minimum growth inhibiting concentration with respect to various microbes using the solutions a and b of the Example 3.

Firstly, the minimum growth inhibiting concentration of the solutions a and b was examined with respect to the *Escherichia coli* MC1061 used in Example 3.

After adjusting the Nutrient Broth (NB) medium (provided by DIFCO Corporation) to have a pH of 7.2, the medium was sterilized for 15 minutes at 121° C. To the medium was added the solution a or solution b to have the solution concentration of each medium as shown in Table 1.

Then, each medium was inoculated with 20 μl of a 100 times diluted inoculum of pre-incubated *Escherichia coli* (species: *Escherichia coli* MC1061), and was incubated for 24 hours at 37° C. The absorbance of the cultured media was then measured as in Example 1 to evaluate growth inhibition of the *Escherichia coli* MC1061 ("*E. coli*" hereinafter). The absorbance of not less than 0.05 was evaluated as "growth", and absorbance of less than 0.05 was evaluated as "no growth". The result of evaluation is shown in Table 3. Note that, in Table 3, "growth" is indicated by "+", and "no growth" is indicated by "−".

TABLE 3

| SOLUTION CONCENTRATION (VOLUME %) | SOLUTION a | SOLUTION b |
|---|---|---|
| CONTROL | + | + |
| 0.08 | + | + |
| 0.1 | + | + |
| 0.2 | + | + |
| 0.3 | + | + |
| 0.4 | + | + |
| 0.5 | + | − |
| 0.6 | + | − |
| 0.7 | + | − |
| 0.8 | − | − |
| 0.9 | − | − |
| 1.0 | − | − |

As can be seen from Table 3, with respect to *E. coli* which is the representative of gram-negative bacteria, the solution a showed the antimicrobial effect at the concentration of not less than 0.8 percent by volume (Ag concentration of 4.0 mg/l), whereas the solution b which includes chlorite as the oxidizing agents showed the antimicrobial effect at the concentration of 0.5 percent by volume (Ag concentration of 2.5 mg/l). That is, the minimum growth inhibiting concentration of the solution a was 0.8 percent by volume and that of the solution b was 0.5 percent by volume. The results show that the solution b which includes the silver ion together with the oxidizing agents have the antimicrobial action at a lower concentration than the solution a even in the medium containing sulfur.

The operations of the foregoing test were performed using *Staphylococcus aureas* IFO3183 ("*S. aureus*" hereinafter) which is the representative of gram-positive bacteria, instead of *E. coli,* and the absorbance was measured as above to evaluate growth inhibition of *S. aureus* by the foregoing evaluation method of Example 3. The result is shown in Table 4.

TABLE 4

| SOLUTION CONCENTRATION (VOLUME %) | SOLUTION a | SOLUTION b |
|---|---|---|
| CONTROL | + | + |
| 0.08 | + | + |

TABLE 4-continued

| SOLUTION CONCENTRATION (VOLUME %) | SOLUTION a | SOLUTION b |
|---|---|---|
| 0.1 | + | + |
| 0.2 | + | + |
| 0.3 | + | + |
| 0.4 | + | + |
| 0.5 | + | − |
| 0.6 | + | − |
| 0.7 | + | − |
| 0.8 | + | − |
| 0.9 | + | − |
| 1.0 | − | − |

As can be seen from Table 4, with respect to *S. aureus* which is the representative of gram-positive bacteria, the solution a showed the antimicrobial effect at the concentration of not less than 1.0 percent by volume (Ag concentration of 5.0 mg/l), whereas the solution b showed the antimicrobial effect at the concentration of 0.5 percent by volume (Ag concentration of 2.5 mg/l). That is, the minimum growth inhibiting concentration of the solution a was 1.0 percent by volume and that of the solution b was 0.5 percent by volume. The results show that the solution b has the antimicrobial effect at a lower concentration.

The same test was also performed using other media, and other bacteria, yeast, and filamentous fungus (mold) so as to measure minimum growth inhibiting concentration of the solution b. Specifically, the minimum growth inhibiting concentration ("MIC" hereinafter) of the solution b was measured with respect to *E. coli* on the desoxycholate medium, *S. aureus* on the MSA medium, other bacteria on the NB medium, yeast on the SABOURAUD medium, and filamentous fungus on the PDA medium. Note that, the incubation temperature was 25° C. and incubation time was 1 day, 3 days, and 7 days for the bacteria, yeast, and filamentous fungus, respectively.

The result showed that the MIC was 0.5 percent per volume for the *E. coli* on the desoxycholate medium and *S. aureus* on the MSA medium, which was the same as the case the NB medium was used. With regard to other bacteria, *Pseudomonas fluorescens* IAM12022, *Bacillus subtilis* 3013, and *Streptococcus lactis* 12546 had the MIC of 0.5 percent by volume, 0.3 percent per volume, and 0.4 percent per volume, respectively. With regard to the yeast, *Pnichia membranaefaciens* IAM4911 and *Debaryomyces hasenii* IAM12209 both had the MIC of 0.3 percent by volume. With regard to the filamentous (mold), *Aspergillus oryzae* IFO4296 and *Penicillium citrinum* IFO both had the MIC of 0.5 percent by volume.

Thus, the solution b, which is the first antimicrobial agent in accordance with the present invention, showed the growth inhibiting effect also for the yeast and mold for which growth inhibition is more difficult than for bacteria, at the concentration substantially the same as that for bacteria (Ag concentration of around 1.5 mg/l to 2.5 mg/l).

EXAMPLE 5

Using the solution b of Example 3, an instant deodorizing test was performed. First, "okara" (bean curd refuse), which is the refuse of wringed soy beans, generated as a by-product in manufacture of "tofu" (bean curd) was spread over two Petri dishes, 100 g on each dish. On the rear surface of one of the Petri dishes was uniformly applied approximately 1 g of the solution b, while the other Petri dish was untreated (no solution was added), and the both Petri dishes were allowed to age in the opened state at 20° C.

The result showed that the untreated sample clearly displayed odor in 3 hours and gradually changed its color to brown, whereas the sample applied with the solution b displayed no odor and no coloration was observed.

The following will describe the second antimicrobial agent and the second antimicrobial treatment method using it.

The first and other inventors of the present invention have filed an application which relates to an antimicrobial agent including the silver-chloro complex salts (Japanese Unexamined Patent Publication No. 182326/1998 (Tokukaihei 10-182326) (published date: May 7, 1998), prior to the present invention.

Unlike thiocyanate complex salt or thiosulfate complex salt of silver, etc., the silver-chloro complex salts do not contain sulfide ion ($S^{2-}$). Thus, the silver-chloro complex salts do not generate a toxic gas by being decomposed by heat or acid and do not blacken by the silver sulfide produced, and therefore is stable.

Further, since the silver-chloro complex salts are highly stable at a high concentration of the chloride ion, it can stably exist in the water-soluble state or near water-soluble state without resulting in precipitation of the silver chloride.

On the other hand, the silver-chloro complex salts have the property of easily depositing the silver chloride or silver metal (silver simple substance) when the concentration of the surrounding chloride ion is reduced by being diluted with water, etc. This is because the amount of the chloride ion which directly contributes to stabilization of the silver-chloro complex salts is reduced in the low concentration state of the chloride ion.

The silver-chloro complex salts demonstrate the antimicrobial properties by the silver chloride or silver metal which was deposited in the low concentration state of the chloride ion and is absorbed on the surface of the target object. The antimicrobial agent of the prior application had the antimicrobial effect on the surface of the target object such as various industrial products or home appliances by utilizing the foregoing property of the silver-chloro complex salts.

However, in the antimicrobial agent of the prior application including the silver-chloro complex salts as the main component, due to the property of the silver-chloro complex salts, it is required to maintain the concentration of the chloride ion at high level during storage, and accordingly it is required to dilute the antimicrobial agent to a predetermined concentration for use. Yet, depending on use of the antimicrobial agent, there are cases where it should be used directly without diluting it with water, etc. Even in such cases, an additional step of diluting the antimicrobial agent to a predetermined concentration is required for use, which complicates the procedure of antimicrobial treatment.

For example, when the antimicrobial treatment is of the form where the antimicrobial agent is stored in a spray container and it is sprayed through a nozzle, etc., for use, the procedure of antimicrobial treatment by diluting the antimicrobial agent in the container every time it is used is extremely tedious and complex.

Also, to store the antimicrobial agent including the silver-chloro complex salts as the main component, as described, the preservation stability needs to be maintained by maintaining the concentration of the silver chloride at high level.

Thus, when the antimicrobial agent is to be used without dilution as above, it must be used in the high concentration state of the chloride ion. Thus, in this case, rust may grow on the surface of the target object, or salts may deposit thereon.

Further, even though the silver-chloro complex salts demonstrate superior antimicrobial activity at a predetermined low concentration, it does not have the immediate property. Thus, in applications where immediate property is required, the silver-chloro complex salts cannot be used by itself. Further, while the silver-chloro complex salts have the antimicrobial activity, it does not have the cleansing ability, thus preventing the target object to be washed at the time of the antimicrobial treatment.

In order to solve the foregoing problems, the second antimicrobial agent in accordance with the present invention includes the silver-chloro complex salts, chloride capable of supplying chloride ion by dissociation (electrolytic dissociation) to stabilize the silver-chloro complex salts, and compounds which have compatibility with a solvent which dissolves the chloride ("solvent" hereinafter) such as water, respectively in a predetermined amount.

In the second antimicrobial agent in accordance with the present invention, the compounds having compatibility with the solvent such as water capture the solvent such as water in the antimicrobial agent so as to reduce the solvent which is not chemically and physically captured, such as free water (water which is not chemically and physically captured) in the vicinity of the silver-chloro complex salts. This makes it possible to reduce the apparent concentration of the chloride ion which exists in the vicinity of the silver-chloro complex salts and which contributes to stabilization of the silver-chloro complex salts. Thus, as a whole, the actual concentration of the chloride ion in the antimicrobial agent can be reduced.

The silver-chloro complex salts contained in the second antimicrobial agent in accordance with the present invention are not particularly limited as long as it can supply the complex ion structure as represented by the structural formula (1) in the solution.

The chloride which included in the second antimicrobial agent in accordance with the present invention, and which supplies the chloride ion for stabilizing the silver-chloro complex salts may be, for example, various chlorides as exemplified as the chlorides of the first antimicrobial agent.

Of the chlorides as exemplified above, it is particularly preferable to adopt those which have high solubility for the compounds having compatibility with the solvent. Among such chlorides, organic compounds such as quaternary ammonium salts, polyamine hydrochloride, primary amine hydrochloride, secondary amine hydrochloride, tertiary amine hydrochloride, and aromatic amines are particularly preferable.

Further, of the chlorides as exemplified above, while chlorides having at least one of lithium ion, magnesium ion, and calcium ion dissolve in compounds having a large polarity such as methanol and ethanol, they are not soluble in compounds with a small polarity among the compounds which are compatible with the solvent. However, since these chlorides have relatively high solubility with respect to the solvent compared with the other chlorides, the concentration of the silver-chloro complex salts can be maintained at high level, which makes these compounds particularly preferable.

The compounds having compatibility with the solvent, included in the second antimicrobial agent in accordance with the present invention, indicate those compounds which interact with and has affinity toward the solvent molecules such as water molecules, for example, by forming a hydrogen bond or ionic bond with the solvent molecules such as the water molecules.

Further, the second antimicrobial agent in accordance with the present invention may include, as required, a solvent which dissolves the chloride. As such a solvent which dissolves the chloride, other than water or protonic solvent which behaves in the same way as water, for example, a non-protonic solvent such as N,N-dimethylformamide, dimethylsulfoxide; propylene carbonate; and polyvinylpyrrolidone are available. Of these solvents, water is particularly preferable. This is because the solubility of the chloride with respect to water is relatively high compared with other solvents, which allows the concentration of the silver-chloro complex salts to be increased in the antimicrobial agent.

The compounds which have compatibility with the solvent include, for example, among organic compounds, alcohols such as methanol, ethanol, 1-propanol, isopropanol, isobutanol, 1-butanol, 2-butanol, 1-pentanol, 2-pentanol, 3-pentanol, 1,1-dimethyl-1-propanol, 2,2-dimethyl-1-propanol, 2-methyl-1-butanol, 3-methyl-1-butanol, 3-methyl-2-butanol, ethylene glycol, diethylene glycol, triethylene glycol, glycerine (glycerol), polyethylene glycol, 3-methyl-1-butyn-2-ol, 3,6-dimethyl-4-octyne-3,6-diol, 2,5-dimethyl-3-hexene-2,5-diol, isoprene glycol, ethyl glycol (ethylene glycol monoethylether), ethyl diglycol (diethylene glycol monoethylether), ethyl triglycol (triethylene glycol monoethylether), butyl glycol (ethylene glycol monobutylether), butyl diglycol (diethylene glycol mononeobutylether), neopentyl glycol (ethylene glycol mononeopentylether), 1,3-butanediol, 1,4-butanediol, 1,5-pentanediol, 1,6-hexanediol, 1,2,6-hexanetriol, propylene glycol, pentaerythritol, hexylene glycol, polypropylene glycol, 3-methyl-1,5-pentanediol, 3-methyl-3-methoxy-1-butanol, 3-methoxy-1-butanol, catechol, and propylene chlorohydrin;

esters such as ethyl acetate, 3-methoxybutyl acetate, propylene glycol monomethylether acetate, ethylene carbonate, methyl lactate, and ethylene glycol diacetate;

ethers such as diethyl ether, ethylene glycol dimethylether, diethylene glycol dimethylether, triethylene glycol dimethylether, polyethylene glycol dimethylether, and dioxane;

nitriles, such as acetonitrile and succinonitrile;

ketones, such as acetone and methylethylketone;

amines and their salts, such as N,N-diethylethanolamine, N,N-dimethylethanolamine, N-(2-aminoethyl) ethanolamine, N-methyldiethanolamine, isopropylamine, isopropanolamine, ethanolamine, mono-n-butylamine, n-hexylamine, α-m-phenylenediamine, β-m-phenylenediamine, hexylamine hydrochloride, benzylamine hydrochloride, diethylamine, biphenylamine, dipropylamine, and triethylamine;

organic acids or their salts, such as formic acid, sodium formate, potassium formate, ammonium formate, rubidium formate, cesium formate, acetic acid, lithium acetate, sodium acetate, magnesium acetate, calcium acetate, cesium acetate, propionic acid, isobutyric acid, 3-aminobutyric acid, 4-aminobutyric acid, oxalic acid, potassium oxalate, tartaric acid, sodium tartrate, citric acid, (±)-malic acid, glyoxylic acid, malonic acid, sodium maleate, potassium gluconate, sodium gluconate, sodium salicylate, potassium salicylate, ammonium salicylate, sodium phthalate, methanesulfonic acid, 1-hydroxyethylidene-1, 1-diphosphonic acid, aminotrimethylene phosphonic acid, pentasodium aminotrimethylene phosphonate, sodium 2-methyl-2-propene-1-sulfonate, ammonium 1-naphthalene sulfonate, o-chlorobenzoic acid, m-chlorobenzoic acid, potassium benzoate, deoxycholic acid, sodium benzenesulfonate, trichloroacetic acid, and sodium nicotinate;

sugars or their derivatives, such as D-glucose, sucrose, L-sorbose, maltose, methyl-D-glucoside, and D-sorbitol;

aldehydes, such as glyoxal and acrylaldehyde;

phenols, such as o-cresol, m-cresol, p-cresol, o-chlorophenol, m-chlorophenol, p-chlorophenol, and phenol; and 1,1-dichloroethane, 1,2-dichloroethane, dimethylcarbonate, polyethyleneimine, dimethyl sulfoxide, dimethylhydrazine, hexanone, phenylhydrazine, N,N-dimethylformamide, 2,2-dimethoxypropane, polyvinyl pyrrolidone, tetrahydrofuran, ethylenecyanhydrin, acetanilide, urea, codeine phosphate, pyrogallol, betaine, betaine hydrobromide, betaine sulfate, 2,4-dimethyl pyridine, 2,6-dimethylpyridine, 2,4,6-trimethylpyridine, 3-methylpyridine, 1-methylpiperidine, 2-methylpiperidine, 3-methylpiperidine, and 4-methylpiperidine.

Further, the inorganic compounds having compatibility with the solvent include, for example, silver perchlorate, silver fluoride, aluminium nitrate, aluminium perchlorate, barium nitrate, calcium chlorate, calcium perchlorate, calcium nitrite, calcium nitrate, calcium amidonitrate, $Ca[SiF_6]$, cadmium selenate, $Ce(NH_4)_2(NO_3)_5$, $Ce(NH_4)_2(NO_3)_6$, cobalt chlorate, cobalt perchlorate, cobalt nitrate, cobalt sulfate, cobalt thiocyanate, $[Co(NH_3)_5(H_2O)](ClO_4)_3$, $[Co(NH_3)_5(H_2O)](NO_3)_3$, $[Co(NH_3)_4(H_2O)_2](NO_3)_3$, $[Co(NH_3)_4(H_2O)_2]_2(SO_4)_3$, $[Cr(NH_3)_5(H_2O)](ClO_4)_3$, $[Cr(N)_3(NH_3)](ClO_4)_2$, chrome perchlorate, chrome nitrate, chrome sulfate, cesium sulfate, cesium hydrogencarbonate, $Cs_2Fe(SO_4)_2$, cesium molybdate, cesium tungstate, copper chloride, copper perchlorate, copper sulfate, $Cu[SiF_6] \cdot 4H_2O$, $Cu(SO_3F_2) \cdot 4NH_3$, copper amidochlorate, iron (I) perchlorate, iron (II) perchlorate, iron (I) nitrate, iron (II) nitrate, $FeK_2(SO_4)_2 \cdot 4H_2O$, $FeK_2(SO_4)_2 \cdot 2H_2O$, $GaNH_4(SO_4)_2 \cdot 12H_2O$, cadmium bromate, $InNH_4(SO_4)_2 \cdot 12H_2O$, potassium carbonate, potassium fluoride, dipotassium hydrogenphosphate, potassium molybdate, tripotassium phosphate, $K_2S_2O_4$, $K_3H(P_2O_5) \cdot 3H_2O$, $KPH_2O_2$, $K_4P_2O_8 \cdot 8H_2O$, $KSnBr_3 \cdot H_2O$, $K_2[Sn(OH)_5] \cdot 2H_2O$, $K_2[Sn(OH)_5]$, $La_2Mg_3(NO_3)_{12}$, lanthanum nitrate, lanthanum bromate, $La(NH_4)_2(NO_3)_5$, lithium bromate, lithium chlorate, lithium perchlorate, lithium iodate, lithium dihydrogenphosphate, lithium nitrate, magnesium chloride, magnesium perchlorate, magnesium nitrate, $Mg_3Nd_2(NO_3)_{12}$, $Mg_3Pr_2(NO_3)_{12}$, magnesium amidosulfate, manganese nitrate, $Mn_3Nd_2(NO_3)_{12} \cdot 24H_2O$, $Mn_3Pr_2(NO_3)_{12} \cdot 24H_2O$, hydroxylamine hydrochloride, ammonium fluoride, ammonium dihydrogenphosphate, ammonium nitrate, ammonium sulfate, $(NH4)_2S_2O_6$, $(NH_4)_2S_2O_8$, $(NH_4)_2S_3O_5$, $(NH_4)_2S_4O_6$, ammonium amidosulfate, hydrazine 1/2sulfate, $(NH_4)_2[Fe(CN)_6]$, sodium hypochlorite, sodium chlorite, sodium perchlorate, sodium monohydrogenphosphate, sodium nitrate, $NaPHO_3$, sodium amidosulfate, sodium tungstate, $Na_2S_3O_5 \cdot 3H_2O$, sodium tellurite, $Na_2[TiF_6]$, neodymium nitrate, neodymium bromate, $Nd_2Zn_3(NO_3)_{12} \cdot 24H_2O$, nickel chlorate, nickel perchlorate, nickel nitrate, $H_4P_2O_6 \cdot 2H_2O$, pyrophosphonic acid, $Ni_3Pr_2(NO_3)_{12}$, praseodymium nitrate, praseodymium bromate, $Pr_2Zn_3(NO_3)_{12} \cdot 24H_2O$, rubidium nitrate, rubidium fluoride, rubidium hydrogencarbonate, $Rb[IBr_2]$, rubidium molybdate, rubidium tungstate, samarium bromate, samarium nitrate, $(NH_4)_2SnBr_4 \cdot H_2O$, strontium nitrate, $Te[GeF_6]$, $TiOSO_4 \cdot 2H_2O$, yttrium nitrate, ytterbium sulfate, zinc chlorate, zinc perchlorate, zinc nitrate, $(NH_4)_2[ZrF_6]$, $(NH_4)_3[ZrF_7]$, and zinc sulfate, etc.

The compound having compatibility with the solvent is preferably alcohols since they have the immediate antimicrobial action. Among alcohols, ethanol, methanol, and isopropanol in particular have superior antimicrobial effect. Thus, by including these compounds as the compound having compatibility with the solvent in the antimicrobial agent, the antimicrobial agent can demonstrate superior antimicrobial effect.

The compound having compatibility with the solvent may be a mixture of compounds of two or more kinds as long as it can be dissolved in the solvent. In this case, the compounds included as the mixture may be compounds which come to have compatibility with the solvent by being mixed.

Suitable combinations of compounds of two or more kinds include: acetic acid and ethyl acetate; acetic acid and hexane; methanol and ethyl acetate; methanol and phenyl; 1-propanol and hexanone; acetone and ethyl acetate; acetone and phenol; ethanol and ethyl acetate; ethanol and diethylether; ethanol and 1,1-dichloroethane; ethanol and 1,2-dichloroethane; and ethanol and hexane, etc.

Further, the compound having compatibility with the solvent included in the second antimicrobial agent in accordance with the present invention may be a surfactant as listed below. This allows the antimicrobial agent to also have the cleansing ability at the same time.

However, of those surfactants exemplified below, anionic surfactants are applicable only when their property is such that the anion derived from the anionic surfactant does not form a precipitate, as in the case where the cation existing in the antimicrobial agent is the alkali earth metal ion, etc.

For example, the surfactant includes:

ether-type non-ionic surfactants, such as polyoxyethylene alkyl ether, polyoxyethylene alkylaryl ether, polyoxyethylene sterolether, polyoxyethylene lanolin derivative, polyoxyethylene alkyl phenol ether formaldehyde condensate, polyoxyethylene.polyoxypropylene block polymer, and polyoxyethylene.polyoxypropylene alkyl ether, etc.;

ether ester-type non-ionic surfactants, such as polyoxyethylene glycerine fatty acid ester, polyoxyethylene castor oil, hydrogenated castor oil, polyoxyethylene sorbitan fatty acid ester, and polyoxyethylene sorbitol fatty acid ester, etc.;

ester-type non-ionic surfactants, such as polyethyleneglycol fatty acid ester, fatty acid monoglyceride, polyglycerine fatty acid ester, sorbitan fatty acid ester, propyleneglycol fatty acid ester, and cane sugar fatty acid ester;

nitrogen-containing non-ionic surfactants, such as fatty acid alkanol amide, polyoxyethylene fatty acid amide, polyoxyethylene alkylamine, and alkylamine oxide; and anionic surfactants, such as alkyl ether carboxylate, acyl peptide, alkylether sulfate, secondary higher alcohol ethoxysulfate, polyoxyethylene alkylphenyl ether sulfate, and alkyl ether phosphate, etc.

Further, among the ether-type non-ionic surfactants, polyoxyethylene alkyl ether includes: polyoxyethylene (3 moles) hexyl ether; polyoxyethylene (3 moles) octyl ether; polyoxyethylene (3 moles) decyl ether; polyoxyethylene (6 moles) octyl ether; polyoxyethylene (6 moles) decyl ether; polyoxyethylene (6 moles) dodecyl ether; polyoxyethylene (9 moles) octyl ether; polyoxyethylene (9 moles) decyl ether; polyoxyethylene (6 moles) hexadecyl ether; polyoxyethylene (12 moles) hexadecyl ether; polyoxyethylene (15 moles) nonyl ether; polyoxyethylene (20 moles) hexadecyl ether; and polyoxyethylene (23 moles) dodecyl ether, etc. Further, the polyoxyethylene alkylaryl ether includes: polyoxyethylene (9 moles) oxylphenyl ether; polyoxyethylene p-1,1,3,3-tetramethylbutylphenyl (9.5 moles) ether (Triton X-100); polyoxyethylene (20 moles) nonylphenyl ether; and polyoxyethylene dinonylphenyl ether, etc. Note that, the number of moles in the brackets after "polyoxyethylene" indicates the number of additional moles of the ethylene oxide, i.e., the repeated number of ethylene oxide chains.

The evaluation method of the surfactant includes, for example, an emulsion measurement method and peel strength measurement method. The emulsion measurement method is the method in which an oil of an arbitrary type is mixed with water containing a surfactant (surfactant concentration of 1 to 10% (w/v)), and evaluation is made by measuring the amount (volume or height) of the emulsion phase. Note that "%(w/v)" indicates the proportion of the solute weight in percent with respect to the total weight of the solution as determined from the total volume of the solution when the specific gravity of the entire solution was 1.

Further, the peel strength measurement method is the method in which a cloth is wetted and soaked in water including the surfactant, and evaluation is made by measuring the time it takes for the oil to be peeled off from the cloth. To carry out this method more easily, a line is drawn on a glass plate with a "magic ink" (trade name), and the glass plate is soaked in water including the surfactant, and evaluation is made by measuring the time it takes for the magic ink to be removed from the glass plate. In addition to the foregoing methods, the surfactant may be measured by other methods such as the method of actually washing dirt off the target object.

The concentration of the chloride in the second antimicrobial agent in accordance with the present invention is not particularly limited, but it is preferable that the chloride be added in a predetermined concentration in accordance with the concentration of the silver-chloro complex salts contained in the antimicrobial agent. For example, when the chloride is sodium chloride, as shown in Table 5 below, it is preferable to adopt a predetermined concentration which shows a positive correlation with respect to the concentration of the silver-chloro complex salts. Specifically, the required concentration of the chloride to stabilize the silver-chloro complex salts (at 25° C.) has the following correlation in water or in a 70%(w/v) ethanol aqueous solution.

TABLE 5

| CONCENTRATION OF SILVER-CHLORO COMPLEX SALTS (SILVER ION CONCENTRATION IN ppm) | NaCl CONCENTRATION REQUIRED TO STABILIZE SILVER-CHLORO COMPLEX SALTS (g/l) | | |
|---|---|---|---|
| | IN WATER (AQUEOUS SOLUTION) (a) | IN AQUEOUS SOLUTION OF 70% (w/v) ETHANOL (b) | (b)/(a) |
| 0.183 | 2.925 | 0.128 | 0.044 |
| 0.410 | 5.850 | 0.287 | 0.049 |
| 2.600 | 29.250 | 1.820 | 0.062 |
| 8.697 | 57.038 | 6.088 | 0.107 |
| 42.189 | 112.905 | 29.532 | 0.262 |

Further, the upper limit value of the chloride concentration is determined by (1) the amount of free water, etc., and (2) the solubility of the cation constituting the chloride with respect to the solvent. For example, since the amount of free water which contributes to the dissolution of the chloride is increased as the content of the compound having compatibility with the solvent deceases, the concentration of the chloride can be increased in the antimicrobial agent as a whole. Further, in the case where the type of cation constituting the chloride has high hydrophilicity, such as lithium, magnesium, calcium, and organic bases, etc., since the solubility with respect to the solvent is high, the upper limit value of the chloride is also increased in this case.

The concentration of the silver-chloro complex salts contained in the second antimicrobial accent in accordance with the present invention becomes different depending on the type of the cation contained in the antimicrobial agent and the type of the compound having compatibility with the solvent. More specifically, it is determined by (1) the amount of solvent which is not chemically and physically captured, such as free water, (2) the solubility of the silver-chloro complex salts with respect to the solvent which is not chemically and physically captured, such as free water, and (3) the concentration of chloride ion in the solvent which is not chemically and physically captured.

With regard to (1), the amount of solvent which is not chemically and physically captured, such as free water, which is required for dissolving the silver-chloro complex salts is increased when the content of the compound having compatibility with the solvent is small, thus increasing the upper limit value of the concentration of the silver-chloro complex salts accordingly. Further, with regard to (3), since whether the silver-chloro complex salts can stably exist without undergoing dissociation of the complex is determined by how much the chloride ion is dissolved in the solvent which is not chemically and physically captured, such as free water, the upper limit value of the silver-chloro complex salts depends on the concentration of the chloride ion.

For example, in the system of silver-chloro complex salts (sodium tetrachloroargentate (I))-sodium chloride-water-ethanol, the upper limit value of the silver-chloro complex salts is 46 ppm when water and ethanol was mixed in the volume ratio of 32:68 and 3%(w/v) of sodium chloride was contained therein.

The concentration of the compound having compatibility with the solvent, included in the second antimicrobial agent in accordance with the present invention, is determined by the amount of the solvent which is not chemically and physically captured, such as free water, which are available to dissolve the cation partially constituting the chloride, or silver-chloro complex salts. Thus, the upper limit value of the concentration of the compound having compatibility with the solvent is determined by the relationship between the concentration of the chloride and the concentration of the silver-chloro complex salts relative to each other. Note that, the stronger the affinity (hydration when the solvent is water) of the compound having compatibility with the solvent toward the solvent which should be captured by the compound, the lesser the amount of the solvent which is not chemically and physically captured, such as free water.

The proportions of the silver-chloro complex salts, the chloride, and the compound having compatibility with the solvent differ depending on the type of each constituent, as described above.

More specifically, in view of antimicrobial activity, the concentration of the silver-chloro complex salts is preferably not less than 0.01 ppm, and more preferably 0.05 ppm in the silver ion concentration.

The upper limit value of the preferable concentration of the compound having compatibility with the solvent is the solubility of the compound with respect to the solvent. However, to keep the concentration of the chloride concentration low, the concentration of the compound having compatibility with the solvent is increased to the concentration closer to the upper limit value. A specific concentration becomes different depending on the type of the compound. For example, when the compound having compatibility with the solvent is ethanol, 50 to 95 volume % is preferable and 60 to 90 volume % is further preferable to achieve effective disinfection.

By the antimicrobial treatment method using the second antimicrobial agent in accordance with the present invention (second antimicrobial treatment method), antimicrobial treatment of any kind of target object is possible. Since the second antimicrobial agent in accordance with the present invention in particular has a lower chloride ion concentration and generates less rust compared with the conventionally used antimicrobial agents, it can be suitable used for kitchen equipment or bath tub made of stainless steel (SUS304), which is susceptible to rust. Further, since the antimicrobial agent containing alcohol as the compound having compatibility with the solvent has lipophilic property, it has the advantage of uniformly treating equipment made of resin, etc. The second antimicrobial agent in accordance with the present invention may also be used for various objects such as concrete wall, floor, ceramic products, and fiber products, etc.

The second antimicrobial treatment method in accordance with the present invention includes, for example, a method of treatment in which the target object is soaked in the second antimicrobial agent, a method of treatment in which the second antimicrobial agent is sprayed on the target object, a method of treatment in which the second antimicrobial agent is directly applied on the target object, and a method of treatment in which the target object is wiped with a cloth, etc., which has absorbed the second antimicrobial agent.

The following will describe the mechanism by which the silver-chloro complex salts contained in the second antimicrobial agent in accordance with the present invention demonstrate the antimicrobial properties on the target object, and the mechanism by which the chloride and the compound having compatibility with the solvent contained in the second antimicrobial agent in accordance with the present invention act on the silver-chloro complex salts.

The silver-chloro complex salts effect the antimicrobial properties on the target object in the form of the silver-chloro complex salts, silver chloride, or silver metal in the solution by the presence of silver as the central ion. The silver ion as the central ion of the silver-chloro complex salts makes the silver chloride to precipitate with decrease in concentration of the surrounding chloride ion. The precipitate of the silver chloride is hardly soluble in water, and thus it is required to prevent precipitation of the silver chloride during storage. However, by further increasing the concentration of the chloride ion in the antimicrobial agent, an equilibrium state can be maintained without resulting in formation of the silver chloride by the chloride ion, thus allowing the silver-chloro complex salts to stably exist in the form of water soluble complex salts.

Therefore, in order to make the silver-chloro complex salts soluble and stabilize it without resulting in precipitation of the silver chloride, the chloride needs to be stored in not less than a certain concentration in the antimicrobial agent. However, when the stored antimicrobial agent is to be used without dilution with the solvent, since the chloride exists in a concentration of not less than a certain level, there are drawbacks that rust may grow on the target object after the treatment or salts deposit.

In the second antimicrobial agent in accordance with the present invention, by mixing the compound having compatibility with the solvent for dissolving the chloride, the concentration of the chloride in the stored antimicrobial agent can be reduced compared with the conventional example. Here, the explanation is based on the case where the solvent dissolving the chloride is water. When the antimicrobial agent contains the compound having compatibility with the solvent, the compound captures water in the equivalent amount of the compound. Thus, the relative amount of water which is not chemically and physically captured, i.e., free water, is reduced compared with the case where the compound having compatibility with water is not contained.

As a result, it is possible to increase the apparent concentration of the chloride ion which contributes to stabilization of the silver-chloro complex salts. Accordingly, the concentration of the chloride ion contained in the antimicrobial agent can be actually reduced while maintaining the concentration of the chloride ion directly required for stabilization of the silver-chloro complex salts. This allows easy antimicrobial treatment without diluting the antimicrobial agent solution in use.

The following will describe the second antimicrobial agent and the second antimicrobial treatment method using it based on Examples.

EXAMPLE 6

The following describes the relationship between the concentration of the chloride when the antimicrobial agent includes the compound having compatibility with the solvent and presence or absence of precipitation of the silver chloride.

An aqueous solution (solution D) including 35% (w/v) of sodium chloride and 500 ppm of the silver-chloro complex salts in the silver ion concentration was prepared. The solution D was mixed with a solution (30 volume % ethanol aqueous solution) to be mixed with the solution D having the composition as shown in Table 6 at the volume ratio of 1:99 so as to prepare an antimicrobial agent solution including the silver-chloro complex salts in the silver concentration as shown in Table 6 and sodium chloride in the final concentration as shown in Table 6. The antimicrobial agent was allowed to age for 4 hours at room temperature and presence or absence of precipitation such as silver chloride was observed. The result is shown in Table 6.

EXAMPLES 7 to 12

The same operations as in Example 6 were performed except for the solutions to be mixed with the solution D having the respective compositions as shown in Table 6. The result is shown in Table 6.

Comparative Examples 1 to 4

The same operations as in Example 6 was performed except for the solutions to be mixed with the solution D having the respective compositions as shown in Table 6. The result is shown in Table 6.

TABLE 6

| | SOLUTION MIXED WITH SOLUTION D | | | ANTIMICROBIAL AGENT SOLUTION | | |
|---|---|---|---|---|---|---|
| | WATER (VOLUME %) | COMPOUND HAVING COMPATIBILITY (VOLUME %) | NaCl (g/l) | SILVER CONCENTRATION (ppm) | NaCl (g/l) | FORMATION OF PRECIPITATES |
| EXAMPLE 6 | 70 | ETHANOL 30 | 0 | 5 | 0.35 | SLIGHT PRECIPITATION OF SILVER CHLORIDE |
| EXAMPLE 7 | 70 | ETHANOL 30 | 30 | 5 | 3.35 | NO PRECIPITATE |
| EXAMPLE 8 | 50 | ETHANOL 50 | 0 | 5 | 0.35 | NO PRECIPITATE |
| EXAMPLE 9 | 30 | ETHANOL 70 | 0 | 5 | 0.35 | NO PRECIPITATE |
| EXAMPLE 10 | 20 | GLYCERINE 80 | 0 | 5 | 0.35 | NO PRECIPITATE |
| EXAMPLE 11 | 20 | ACETONE 80 | 0 | 5 | 0.35 | NO PRECIPITATE |
| EXAMPLE 12 | 70 | SURFACTANT A 14 (*) | 0 | 5 | 0.35 | NO PRECIPITATE |
| COMPARATIVE EXAMPLE 1 | 100 | — | 0 | 5 | 0.35 | PRECIPITATION OF SILVER CHLORIDE |
| COMPARATIVE EXAMPLE 2 | 100 | — | 30 | 5 | 3.35 | PRECIPITATION OF SILVER CHLORIDE |

TABLE 6-continued

|  | SOLUTION MIXED WITH SOLUTION D | | | ANTIMICROBIAL AGENT SOLUTION | | |
| --- | --- | --- | --- | --- | --- | --- |
|  | WATER (VOLUME %) | COMPOUND HAVING COMPATIBILITY (VOLUME %) | NaCl (g/l) | SILVER CONCENTRATION (ppm) | NaCl (g/l) | FORMATION OF PRECIPITATES |
| COMPARATIVE EXAMPLE 3 | 100 | — | 60 | 5 | 6.35 | NO PRECIPITATE |
| COMPARATIVE EXAMPLE 4 | 0 | ETHANOL 100 | 0 | 5 | 0.35 | PRECIPITATION OF NaCl |

(*) % (w/v)
SURFACTANT A: POLYOXYETHYLENE (20 MOLES) SORBITAN MONOOLEATE

As shown in Table 6, the antimicrobial agents containing ethanol, glycerine, and acetone in predetermined concentrations did not show precipitation of the silver chloride as with the antimicrobial agent of Comparative Example 3 containing sodium chloride in the final concentration of 6.35 g/l. It can be seen from this result that the silver-chloro complex salts can be stabilized without including high concentration sodium chloride but the foregoing compounds in predetermined concentrations.

As shown by the result of Example 6, the antimicrobial agent solution containing ethanol in a concentration of about 30 volume percent generated a slight precipitate of the silver chloride. However, as shown by Example 7, the silver chloride does not precipitate at all when this antimicrobial agent solution contains sodium chloride in a concentration (final concentration 3.35 g/l) lower than conventionally.

EXAMPLE 13

$E.\ coli$ and $S.\ aureus$ were each incubated on a triptosoya.bouillon medium (provided by NISSUI PHARMACEUTICAL Co., Ltd.) for 24 hours at 37° C. to prepare an inoculum having a concentration of about $10_8$ CFU/ml. 0.1 ml of the each inoculum thus prepared was independently added to 10 ml of the antimicrobial agent solution having the same composition ratio as in Example 9, i.e., the antimicrobial agent solution of 70 percent by volume of the ethanol aqueous solution containing the silver-chloro complex salts in the silver concentration of 5 ppm and sodium chloride in the concentration of 0.35 g/l, which was then processed for 10 minutes. Then, 0.1 ml of each solution was collected and 10 ml of the triptosoya.bouillon solution was added thereto for incubation at 37° C. for 72 hours. The turbidity of the incubated solutions was observed by visual inspection and presence or absence of proliferation of the respective bacteria was judged. The results are shown in Table 7. Note that, in Table 7, "+" indicates proliferation of the bacteria, and "−" indicates no proliferation of the bacteria.

Comparative Examples 5 to 9

The same operations as in Example 13 were performed except that the comparative antimicrobial agent solutions as shown in Table 7 were used as the antimicrobial agent solutions. The results are shown in Table 7.

TABLE 7

|  | ANTIMICROBIAL AGENT SOLUTION | PRESENCE OR ABSENCE OF PROLIFERATION | |
| --- | --- | --- | --- |
|  |  | Escherichia coli | Staphylococcus aureus |
| EXAMPLE 13 | SAME AS EXAMPLE 9 | − | − |
| COMPARATIVE EXAMPLE 5 | SAME AS COMPARATIVE EXAMPLE 1 | + | + |
| COMPARATIVE EXAMPLE 6 | SAME AS COMPARATIVE EXAMPLE 2 | + | + |
| COMPARATIVE EXAMPLE 7 | SAME AS COMPARATIVE EXAMPLE 3 | + | + |
| COMPARATIVE EXAMPLE 8 | WATER | + | + |
| COMPARATIVE EXAMPLE 9 | 70 VOLUME % ETHANOL AQUEOUS SOLUTION | − | − |

EXAMPLE 14

The antimicrobial agent having the same composition as in Example 9 (antimicrobial agent containing ethanol in a predetermined concentration) was prepared. The antimicrobial agent immediately after the preparation was sprayed on a petri dish of the size $\phi 9$ cm to have 1 $\mu l/cm^2$ of the antimicrobial agent solution, which was then wind dried and allowed to age at room temperature for 7 days. Then, 0.5 ml of a suspension liquid of $E.\ coli$ in the concentration of $10^6$ CFU/ml was dropped on the perti dish. The petri dish was then covered with a sterilized film of the size 4.5×4.5 cm and was processed for 24 hours at 25° C. while maintaining a relative humidity of not less than 90%. After the process, 0.1 ml of the suspension liquid was collected and spread over a standard agar medium (provided by NISSUI PHARMACEUTICAL Co., Ltd.), which was then incubated for 24 hours at 35° C., and the number of bacteria was counted. The result is shown in Table 8.

EXAMPLES 15 and 16

The same operations as in Example 14 were performed except that an antimicrobial agent solution having the same composition as in Example 10 (antimicrobial agent solution containing glycerine in a predetermined concentration) and an antimicrobial agent having the same composition as Example 11 (antimicrobial agent solution containing acetone in a predetermined concentration) were used instead of the antimicrobial agent solution used in Example 14. The result is shown in Table 8.

Comparative Examples 10 to 14

The same operations as in Example 14 were performed except that comparative antimicrobial agent solutions as shown in Table 8 were used instead of the antimicrobial agent solution used in Example 14. The result is shown in Table 8.

TABLE 8

| | ANTIMICROBIAL AGENT SOLUTION | NUMBER OF BACTERIA |
|---|---|---|
| EXAMPLE 14 | SAME AS EXAMPLE 9 | 0.0 |
| EXAMPLE 15 | SAME AS EXAMPLE 10 | 0.0 |
| EXAMPLE 16 | SAME AS EXAMPLE 11 | 0.0 |
| COMPARATIVE EXAMPLE 10 | WATER | $2.6 \times 10^5$ |
| COMPARATIVE EXAMPLE 11 | 70 VOLUME % ETHANOL AQUEOUS SOLUTION | $2.1 \times 10^5$ |
| COMPARATIVE EXAMPLE 12 | SAME AS COMPARATIVE EXAMPLE 1 | 0.0 |
| COMPARATIVE EXAMPLE 13 | SAME AS COMPARATIVE EXAMPLE 2 | 0.0 |
| COMPARATIVE EXAMPLE 14 | SAME AS COMPARATIVE EXAMPLE 3 | 0.0 |

EXAMPLE 17

An antimicrobial agent solution having the same composition as in Example 12 (antimicrobial agent solution containing sorbitan monooleate in a predetermined concentration) was prepared. The antimicrobial agent solution immediately after preparation was sprayed on a petri dish of the size $\phi 9$ cm so as to have 1 $\mu l/cm^2$ of the antimicrobial agent solution, which was then washed twice with 10 ml of water each time, wind dried, and allowed to age at room temperature for 7 days. On the petri dish was dropped 0.5 ml of the suspension liquid of E. coli in a concentration of $10^6$ CFU/ml, and the petri dish was covered with a sterilized film, which was then processed for 24 hours at 25° C. while maintaining the relative humidity of not less than 90%. After the process, 0.1 ml of the suspension liquid was collected and incubated at 35° C. for 24 hours using the standard agar medium and the number of bacteria was counted. The result is shown in Table 9.

Comparative Examples 15 to 18

The same operations as in Example 17 were performed except that the comparative antimicrobial agent solutions as shown in Table 9 were used instead of the antimicrobial agent solution used in Example 17. The result is shown in Table 9.

TABLE 9

| | ANTIMICROBIAL AGENT SOLUTION | NUMBER OF BACTERIA |
|---|---|---|
| EXAMPLE 17 | SAME AS EXAMPLE 12 | 0.0 |
| COMPARATIVE EXAMPLE 15 | WATER | $2.6 \times 10^5$ |
| COMPARATIVE EXAMPLE 16 | SAME AS COMPARATIVE EXAMPLE 1 | 0.0 |
| COMPARATIVE EXAMPLE 17 | SAME AS COMPARATIVE EXAMPLE 2 | 0.0 |
| COMPARATIVE EXAMPLE 18 | SAME AS COMPARATIVE EXAMPLE 3 | 0.0 |

EXAMPLE 18

10 ml of a commercially available edible oil (product name "Nissin Salad Oil" manufactured by The Nissin Oil Mills, Ltd) and 40 ml of distilled water were charged in a 100 ml graduated cylinder. To this liquid mixture was added 5 ml of an antimicrobial agent solution having the same composition as in Example 12 (antimicrobial agent containing polyoxyethylene (20 moles) sorbitan monooleate in a predetermined concentration). Then, the graduated cylinder was sealed on the opening with a parafilm (trade mark) and was agitated by shaking it well up and down. The mixture was allowed to age at 25° C. for 18 hours and the volume of the emulsion phase was measured. The result is shown in Table 10.

Comparative Examples 19 and 20

The same operations as that in Example 18 were performed except that water and the comparative antimicrobial agent solution having the same composition as in Example 1 were used instead of the antimicrobial agent used in Example 18. The result is shown in Table 10.

Comparative Example 21

The same operations as in Example 18 were performed except that 14% (w/v) of a polyoxyethylene (20 moles) sorbitan monooleate aqueous solution was used instead of the antimicrobial agent solution used in Example 18. The result is shown in Table 10.

TABLE 10

| | ANTIMICROBIAL AGENT SOLUTION | VOLUME OF EMULSION PHASE |
|---|---|---|
| EXAMPLE 18 | SAME AS EXAMPLE 12 | 9 ml |
| COMPARATIVE EXAMPLE 19 | WATER | 1 ml |
| COMPARATIVE EXAMPLE 20 | SAME AS COMPARATIVE EXAMPLE 1 | 1 ml |
| COMPARATIVE EXAMPLE 21 | (*) | 9 ml |

(*) 14% (w/v) polyoxyethylene (20 moles) sorbitan monooleate aqueous solution

EXAMPLE 19

1 ml of a commercially available edible oil (product name "Nissin Salad Oil" manufactured by Nissin Oil Mills, Ltd) was dropped on a petri dish made of polystyrene having the size $\phi 9$ cm, and spread over the surface of the petri dish with a steering stick made of glass. Then, after washing the surface of the petri dish with a sponge containing the antimicrobial agent solution having the same composition as in Example 12, the perti dish was rinsed with distilled water. Then, any residue of the oil was observed by visual inspection on the surface of the petri dish. The result is shown in Table 11.

Comparative Examples 22 and 23

The same operations as in Example 19 were performed except that water or the antimicrobial agent solution having the same composition as in Comparative Example 1 immediately after its preparation were used instead of the antimicrobial agent solution used in Example 19. The result is shown in Table 11.

Comparative Example 24

The same operations as in Example 19 were performed except that 14% (w/v) of a polyoxyethylene (20 moles) sorbitan monooleate aqueous solution was used instead of the antimicrobial agent solution used in Example 19. The result is shown in Table 11.

TABLE 11

| | ANTIMICROBIAL AGENT SOLUTION | OIL RESIDUE |
|---|---|---|
| EXAMPLE 19 | SAME AS EXAMPLE 12 | ABSENT |
| COMPARATIVE EXAMPLE 22 | WATER | PRESENT |
| COMPARATIVE EXAMPLE 23 | SAME AS COMPARATIVE EXAMPLE 1 | PRESENT |
| COMPARATIVE EXAMPLE 24 | (*) | ABSENT |

(*) 14% (w/v) polyoxyethylene (20 moles) sorbitan monooleate aqueous solution

As shown in Table 11, oil residue was not observed when the antimicrobial agent solution containing polyoxyethylene (20 moles) sorbitan monooleate was used, showing the cleansing ability for the oil. It can also be seen from the results of Example 19 and Example 17 shown in Table 9 that the antimicrobial agent solutions containing the surfactant has the sustained antimicrobial properties and the cleansing ability.

Further, as indicated by the foregoing results altogether, the antimicrobial agent solution containing a predetermined concentration of ethanol can stabilize the silver-chloro complex salts and has the immediate antimicrobial property, i.e., disinfecting ability, without containing sodium chloride in high concentration. Further, the antimicrobial agent solutions containing ethanol, glycerine, and acetone respectively in predetermined concentrations can stabilize the silver-chloro complex salts and has the sustained antimicrobial property without containing sodium chloride in high concentration. Further, the antimicrobial agent solution containing polyoxyethylene (20 moles) sorbitan monooleate can stabilize the silver-chloro complex salts and has the surfactant property and sustained antimicrobial property without containing sodium chloride in high concentration.

The following will describe a third antimicrobial agent in accordance with the present invention in detail.

As described, the silver-chloro complex salts demonstrate the antimicrobial properties by depositing silver chloride or silver metal in a low concentration state of the chloride ion and by absorption of the silver chloride or silver metal on the surface of the target object.

More specifically, the antimicrobial properties by the silver chloride absorbed on the surface of the target object are obtained by the silver-chloro complex salts which become unstable and deposit in the form of particles of the silver chloride in a low concentration state of the chloride ion. For example, the surface of target objects such as fiber products has high surface energy and accordingly a large number of deposited silver chloride particles are absorbed on the surface thereof. Note that, crystals may grow from the crystal of the absorbed silver chloride acting as a nucleus, and the crystal in this case will have the size of about 1 μm.

Thus, in the antimicrobial treatment of target objects, by setting a chloride ion concentration which would generate silver chloride particles, the particles of the silver chloride are fixed or anchored on the surface of the target objects, thereby effecting the antimicrobial treatment on the target objects.

The antimicrobial agent of the prior application (Tokukaihei 10-182326) effects the antimicrobial properties on the surface of the target object such as various industrial products and home appliances by utilizing the foregoing properties of the silver-chloro complex salts.

However, in the antimicrobial agent of this prior application, the chloride contained to supply the chloride ion is limited to ammonium chloride, and chlorides of alkali metal or alkali earth metal. These chlorides all have the property of depositing crystals of, for example, while crystals when they cannot be further dissolved in the solution as the solvent evaporates. Thus, in the case of the antimicrobial treatment where the antimicrobial agent is sprayed or applied on the target object in a concentration which demonstrates the antimicrobial properties, the appearance or feel of the target object may be lost by the white crystals, etc.

Further, in the antimicrobial agent of the foregoing prior application, when the target object is, for example, a liquid such as foul water or waste fluid, it becomes relatively difficult for the fine particles of the silver chloride to demonstrate the superior antimicrobial properties. This is because when the target object is a liquid such as foul water or waste fluid, unlike the case of fiber products, etc., the fine particles of the silver chloride are homogeneously dispersed in the liquid and delocalized, thus making it relatively difficult to effect the antimicrobial treatment.

Further, the antimicrobial agent of the foregoing prior application has large boundary tension (surface tension) and does not permeate sufficiently with respect to the target object. Thus, for example, when the surface of the target object has fine voids, etc., the antimicrobial agent cannot reach into the voids, and bacteria or mold existing in such fine voids may not be subjected to the antimicrobial treatment sufficiently. Thus, with the foregoing antimicrobial agent, the antimicrobial treatment may not be effected effectively on target objects having a complex surface structure, for example, such as the voids.

In order to solve the foregoing problems, the third antimicrobial agent in accordance with the present invention includes the silver-chloro complex salts and the chloride for supplying chloride ion to stabilize the silver-chloro complex salts, wherein the chloride has at least one of (I) a property capable of existing as a supersaturated aqueous solution for 24 hours or longer in the presence of a crystal nucleus at least at room temperature, and (II) a property capable of being decomposed when dissolved in water, and the silver-chloro complex salts.

The silver-chloro complex salts included in the third antimicrobial agent in accordance with the present invention are not particularly limited as long as it is a salt having the complex ion structure as represented by the structural formula (1).

The chloride included in the third antimicrobial agent in accordance with the present invention has at least one of (I) the property capable of existing as a supersaturated aqueous solution for 24 hours or longer in the presence of a crystal nucleus at least at room temperature (first property), and (II) the property capable of being decomposed when dissolved in water (second property), and it has the function of stabilizing the silver-chloro complex salts.

The following will describe in further detail the relationship between the first and second properties and how the third antimicrobial agent in accordance with the present invention prevents appearance or feel of the target object from being affected by deposition of crystals such as white crystals on the surface of the target object.

In general, compounds take the semi-stable state in the supersaturated state, i.e., in a state of a solution (supersaturated solution) containing a solute in the amount equal to or larger than the amount equivalent to the solubility which is distinct to the compounds, and thus they lose stability by external stimuli, for example, such as the presence of the crystal nucleus, and start transition from the liquid phase to the solid phase, i.e., crystal deposition proceeds.

However, by the first property, the chloride proceeds with the transition at a significantly slow rate on chemical kinetics. Further, the transition proceeds even slower when the crystal nucleus is not present than the case it is present. Thus, under normal antimicrobial treatment conditions, the supersaturated aqueous solution can stably exist practically permanently.

As described, since the chloride having the first property does not have a clear boundary defining the supersaturation, it does not deposit as a crystal even when the chloride is concentrated by being dried after the antimicrobial treatment. Therefore, with the antimicrobial agent including the chloride having the first property, there will be no crystal deposition which can be observed by visual inspection even when the antimicrobial agent is dried after the antimicrobial treatment.

Further, the chloride having the second property is decomposed by being dissolved in water. Here, when referring to "a compound is decomposed by being dissolved in water", it is meant that the compound becomes another compound by being dissolved in water. More specifically, "decompose" refers to the phenomenon in which the compound before being dissolved in water is different from the compound which was once dissolved in water and later recovered by removing water.

Thus, in the antimicrobial agent including the chloride having the second property, even in the case where the ingredients of the antimicrobial agent are concentrated by being dried after the antimicrobial treatment, there will be no crystal deposition because the compounds generated from these ingredients by the decomposition of the chloride are hydrolyzed products, and mostly basic salts and their polymers.

Thus, by using the chloride having at least one of the first and second properties, it is possible to prevent deposition of crystals such as white crystals, which cause the surface of the target object to have a rough feel or spoil the appearance thereof.

Here, the first and second properties of the chloride in accordance with the present invention can be seen as a unique property whereby there is no match in solubility at a predetermined temperature and accordingly the solubility cannot be clearly determined.

More specifically, the first and second properties refer to the case which satisfies at least one of the following conditions (1) to (3): (1) the solubility which was measured by dissolving the chloride in the solvent does not match the solubility which was measured as the amount of the solvent in the dissolution by concentrating the solution; (2) the solubility which was measured by dissolving the chloride at a fast rate does not match the solubility which was measured by dissolving the chloride at a slower rate; and (3) the solubility which was measured by dissolving the chloride at a predetermined temperature does not match the solubility which was measured by dissolving the chloride at a higher temperature and then cooling it to the predetermined temperature. Here, whether there is a match is decided by whether the difference exceeds 10%.

The degree of supersaturation of the supersaturated solution in the first property, i.e., the range of measure which indicates the degree of saturation is suitably decided by the type and amount of the chloride used and is not particularly limited.

The chloride included in the third antimicrobial agent in accordance with the present invention has at least one of the first and second properties at least at room temperature, i.e., at a temperature of the everyday environment in which the antimicrobial treatment is usually effected, for example, at a temperature in a range of about 18° C. to 25° C.

The chloride included in the third antimicrobial agent in accordance with the present invention includes, for example, organic compounds such as polyaluminium chloride, tetramethylammonium chloride, trioctylmethylammonium chloride, choline chloride, benzalkonium chloride, benzethonium chloride, trimethylbenzylammonium chloride, tributylethylammonium chloride, tributylbenzylammonium chloride, imidazolinium chloride, and N-laurylpyridinium chloride.

Of the chlorides as exemplified above, polyaluminium chloride is particularly preferable when the target object is a liquid, for example, such as foul water or waste fluid since the polyaluminium chloride forms colloid hydroxides (aluminium hydroxide) in the aqueous solution, which absorbs and disperses the fine particles of the silver chloride which demonstrates the antimicrobial properties, thereby localizing the fine particles of the silver chloride in the aqueous solution.

Further, of the chlorides as exemplified above, the organic compounds, i.e., compounds having carbons can reduce the surface tension of the solution, and increase the permeability of the antimicrobial agent solution with respect to the target object when the antimicrobial agent is used in the form of a solution. As a result, even when the target object has, for example, a complicated surface structure such as small voids, the antimicrobial agent can reach into the voids and sufficiently effect the antimicrobial treatment for the bacteria or mold existing in such small voids, thus making these organic compounds particularly preferable.

Further, among the organic compounds as exemplified as above, the chlorides which function as the cationic surfactant, such as benzalkonium chloride, benzethonium chloride, imidazolinum chloride, and N-laurylpyridinium chloride, and, in particular, benzalkonium chloride can further reduce the surface tension of the antimicrobial agent solution, making these compounds even more preferable since they can demonstrate the antimicrobial properties further effectively when used for the antimicrobial treatment on target objects having a complicated surface structure. Further, benzalkonium chloride has the disinfecting ability and thus particularly preferable when antimicrobial properties with superior immediate action are needed.

In the case of the antimicrobial treatment using the third antimicrobial agent in accordance with the present invention, the concentration of the silver-chloro complex salts in the antimicrobial treatment is not particularly limited as long as the antimicrobial properties are sufficiently effected when the antimicrobial agent is used either directly, for example, in undiluted form or the dilution of several tens to several thousand times. Specifically, the range by which the antimicrobial properties are demonstrated is preferably in a range of 0.01 to 5000 mg/l in the silver concentration in the solution, or more preferably in a range of 0.1 to 2000 mg/l, and most preferably in a range of 1 to 500 mg/l in the antimicrobial treatment.

Further, in the case where the antimicrobial agent in accordance with the present invention is in the form of a solution, the concentration of the chloride in the antimicrobial agent is not particularly limited and it is suitably set in accordance with the type or solubility, etc., of the chloride, but a range of 1 to 500 g/l is preferable, and a range of 10 to 400 g/l is more preferable, and a range of 100 to 300 g/l is most preferable.

The ratio of the silver-chloro complex salts to the chloride in accordance with the present invention is not particularly limited as long as it is in a predetermined range which allows the antimicrobial agent to effect the antimicrobial properties, and a weight ratio of $1:5\times10^8$ to 1:2 is preferable, and 1:1000 to $1:10^7$ is more preferable.

The third antimicrobial agent in accordance with the present invention may be in the form of a solution, for example, such as an aqueous solution, or, for example, a solid such as a powder. Further, the third antimicrobial agent in accordance with the present invention may contain other ingredients, as required, in addition to the silver-chloro complex salts and the chloride.

The third antimicrobial agent in accordance with the present invention can be adapted to effect the antimicrobial treatment on various kinds of target objects. The target objects which can be treated by the antimicrobial treatment of the third antimicrobial agent in accordance with the present invention includes various industrial products and home appliances employing such raw materials as resin, fiber, paper, wood, cement, mortar, plaster, unwoven fabric, felt, and leather, and also concrete walls, floor, and ceramic products. The antimicrobial agent is to be effected on the target objects themselves, and as such, the target objects include those objects, for example, such as cosmetics or builder in the form of a powder on which the antimicrobial properties are effected by suitably mixing the third antimicrobial agent in accordance with the present invention therewith.

Further, in the case where the third antimicrobial agent in accordance with the present invention is, for example, chlorides of organic compounds, such as benzalkonium chloride, it is possible to effect the antimicrobial properties which are particularly effective on target objects having a complicated surface structure such as small voids. Examples of the target objects having small voids include, for example, walls, floors, ceilings, joints of tiles, which are made from cement, mortar, or plaster, etc.; walls, floors, ceilings, and furniture, which are made from wood, etc.; and filters made from unwoven fabric or felt, etc.

When the third antimicrobial agent in accordance with the present invention is a solid, it can be used, for example, by containing it in a powder such as a powder detergent. Further, when the third antimicrobial agent in accordance with the present invention is a solid, it can be used to obtain resin or fiber having antimicrobial properties, for example, by kneading it with resin or fiber, etc.

The third antimicrobial agent in accordance with the present invention may be used to treat target objects, for example, by washing the target object with a powder detergent or powder laundry supplement containing the third antimicrobial agent in the form of fine particles, by soaking the target object in the solution of the third antimicrobial agent, by spraying the solution of the third antimicrobial agent on the target object, directly applying the third antimicrobial agent on the target object, by applying the third antimicrobial agent on the target object in the form of a solution or a mixture with a creamy substance, and by wiping the target object with a cloth, etc., which has absorbed the third antimicrobial agent.

The method of producing the third antimicrobial agent in accordance with the present invention is not particularly limited, and the third antimicrobial agent can be produced by the process of preparing a solution by mixing the silver and/or silver compound, chloride, and solvent such as water, or in the case where the antimicrobial agent is a solid, by the additional process of removing the solvent from the solution by evaporation, etc.

The silver used herein is the silver metal. Also, the silver compound is not particularly limited as long as it can supply the silver ion by dissociation, and may be, for example, silver salts such as silver chloride, silver sulfate, and silver nitrate.

The temperature in the process of preparing the solution by mixing the silver and/or silver compound, chloride, and solvent such as water may be suitably set and is not particularly limited, but a range of 5 to 95° C. is preferable. Further, the temperature in the process of removing the solvent by evaporation, etc., may be suitably set and is not particularly limited, but a range of −20 to 900° C. is preferable.

The order of mixing the silver and/or silver compound, chloride, and solvent such as water in the process of preparing the solution of these compounds is not particularly limited, and, for example, it may be conducted, for example, by the method of dissolving the chloride in water to prepare an aqueous solution, and by adding and mixing silver and/or silver compound therein.

As described, the third antimicrobial agent in accordance with the present invention includes the silver-chloro complex salts and the chloride for stabilizing the silver-chloro complex salts, wherein the chloride has at least one of (I) the property capable of existing as a supersaturated aqueous solution for 24 hours or longer even in the presence of a crystal nucleus at least at room temperature, and (II) the property capable of being decomposed when dissolved in water.

By the chloride having at least one of the foregoing properties, there will be no deposition of crystals such as white crystals, which cause the surface of the target object after antimicrobial treatment to have a rough feel or spoil the appearance, even when the antimicrobial agent is dried and the ingredients therein are concentrated after the antimicrobial treatment. Further, even though there are cases where a transparent residue of an irregular shape remains on the surface of the target object, it is either the chloride which exists in the supersaturated state, or a compound which was decomposed by being dissolved and is different from the chloride. Such a residue does not cause the target object to have a rough feel or does not spoil the appearance, thus maintaining the feel or appearance of the target object.

Further, the antimicrobial agent including, for example, polyaluminium chloride among the foregoing chlorides has the property of generating colloid hydroxides in the aqueous solution, and the colloid hydroxides absorb and disperse the fine particles of the silver chloride in the aqueous solution, thus localizing the fine particles of the silver chloride which demonstrates the antimicrobial properties. As a result, it is possible to effect superior antimicrobial properties compared with the conventional antimicrobial properties when the target object is, for example, a liquid such as foul water or waster fluid.

Further, the antimicrobial agent including, for example, chlorides of organic compounds such as benzalkonium chloride among the foregoing chlorides can reduce the surface tension of the antimicrobial agent solution and thus can increase the permeability with respect to the target object. As a result, it is possible to effect the antimicrobial properties which are effective with respect to target objects having a complicated surface structure such as small voids.

The following will describe the third antimicrobial agent in accordance with the present invention in more detail based on Examples and Comparative Examples, which by no way limit the present invention. Note that, various testing methods in the following Examples and Comparative Examples are as follows.

<Method of Confirming Presence or Absence of White Crystals>

The following method was employed to confirm presence or absence of white crystal deposition on the surface of the target object after antimicrobial treatment by the antimicrobial agent. The undiluted solution and a 100 times diluted solution were each sprayed on a glass petri dish having a diameter of 9 cm in the concentration of 10 $\mu l/cm^2$, which was then dried at 30° C. for one day. After dried, presence or absence of white crystal deposition on the surface of the glass petri dish was confirmed by visual inspection.

<potato juice deodorant effect test>

Potato was squashed in a juicer and 100 ml of the juice was poured respectively into Erlenmeyer flasks each having a volume of 200 ml. The antimicrobial agent was then added to the respective juice in the silver concentrations of 0.2 mg/l, 1.0 mg/l, and 5.0 mg/l, and after sufficient stirring, the mixture was allowed to age at 20° C. The odor of each potato juice after a predetermined time period was evaluated by the sensory test by ten testers to determine the average value of the evaluation values of the sensory test, which indicate the degree of odor. The evaluation values of the sensory test were given in five levels: 5 "no odor", 4 "slight odor", 3 "weak odor", 2 "odor", and 1 "strong odor".

<Antimicrobial Property Test>

To a 50 ml centrifuge tube was added 10 ml of a suspension liquid which contained 7.0×10$^5$ CFU/ml of MRSA in a 1/1000 diluted triptosoya.bouillon medium (provided by NISSUI PHARMACEUTICAL Co., Ltd.), and the antimicrobial agent was added therein in the silver concentration of 0.1 mg/l. Then, while rotating it at 150 rpm, the suspension liquid was incubated at about 25° C. for a predetermined time period and the number of bacteria in 1 ml of the suspension liquid was counted by the following bacteria counting method. Also, for comparison, the same operations were performed without adding the antimicrobial agent.

<Antimicrobial Treatment Effect Test by Spraying>

A diluting solution which had been diluted to have the concentration of the antimicrobial agent in the silver concentration of 1.0 mg/l was sprayed on a perti dish of the size φ9 cm in the concentration of 1 $\mu l/cm^2$ and dried thereon, which was then stored for 3 days at 20° C. On the petri dish was dropped 0.5 ml of a suspension liquid which contained 5.0×10$^6$ CFU/ml of MRSA in a 1/1000 diluted triptosoya.bouillon medium. Then, the petri dish was covered with a sterilized film of 4.5 cm×4.5 cm, which was allowed to age for 24 hours at 25° C. while maintaining a relative humidity of 100%. Thereafter, 5 ml of a 1/1000 diluted triptosoya.bouillon medium was added and the suspension liquid treated by the antimicrobial treatment was recovered. The number of bacteria in 1 ml of the suspension liquid which was treated by the antimicrobial treatment and thus recovered was then counted by the following bacteria counting method. Also, for comparison, the same operations were performed without adding the antimicrobial agent.

<Permeability Confirmatory Test of Antimicrobial Agent>

100 $\mu l$ of an aqueous solution which had been prepared by diluting the antimicrobial agent 100 times with pure water was delicately dropped on a petri dish made of polystyrene, and the diameter (mm) of the droplet was measured after 1 minute. The diameter was used as a measure of indicating permeability. Further, the surface tension (dyn/cm) of the aqueous solution at 20° C. was measured using an automatic surface tension balance (product name: "automatic surface tension balance K10ST" provided by Crus Company). The permeability of the antimicrobial agent was judged high with a larger diameter of the droplet, or with a lower surface tension. Also, for comparison, the diameter and surface tension of water, instead of the antimicrobial agent, were measured.

<Bacteria Number Counting Method>

A suspension liquid, or a diluting solution which had been prepared by diluting the suspension liquid with 1/1000 diluted triptosoya.bouillon (provided by NISSUI PHARMACEUTICAL Co., Ltd.) was prepared. 1 ml of the suspension liquid or diluting solution was placed on a petri dish of the size φ9 cm. Then, to the petri dish was added 20 ml of a standard agar medium (provided by NISSUI PHARMACEUTICAL Co., Ltd.) which had been sterilized by an autoclave and cooled to 40° C. The medium was stirred sufficiently and allowed to age to a solid. After incubating the petri dish for 24 hours at 36° C., the number of colonies was counted to calculate the number of bacteria (CFU/ml) in 1 ml of the suspension liquid.

EXAMPLE 20

An aqueous solution was prepared as the third antimicrobial agent in accordance with the present invention to have the silver-chloro complex salts in the silver concentration of 0.13 g/l and the polyaluminium chloride as the chloride in accordance with the present invention in the AlCl$_3$ equivalent concentration of 100 g/l.

Then, presence or absence of white crystals on the surface of the target object after antimicrobial treatment by the antimicrobial agent was examined by the foregoing confirmatory method. The results are shown in Table 12.

Then, the deodorant effect of the antimicrobial agent with respect to the potato juice was confirmed by the foregoing confirmatory method. The results are shown in Table 13.

Further, the antimicrobial effect of the antimicrobial agent with respect to MRSA was examined by the foregoing antimicrobial property test. The results are shown in Table 14.

EXAMPLE 21

The same operations as in Example 20 were performed to obtain the third antimicrobial agent in accordance with the present invention except that the silver-chloro complex salts in the silver concentration of 0.08 g/l, and benzalkonium chloride instead of the polyaluminium chloride were used.

Then, presence or absence of white crystals on the surface of the target object after antimicrobial treatment by the antimicrobial agent was examined by the foregoing confirmatory method. The results are shown in Table 12.

Further, the antimicrobial effect of the antimicrobial agent with respect to MRSA was examined by the foregoing antimicrobial property test. The results are shown in Table 14.

Also, the antimicrobial effect of the antimicrobial agent with respect to MRSA was examined by the foregoing antimicrobial treatment effect test by spraying. The results are shown in Table 15.

Further, the permeability of the antimicrobial agent with respect to the target object was confirmed by the foregoing permeability confirmatory test for the antimicrobial agent. The results are shown in Table 16.

EXAMPLE 22

An aqueous solution was prepared as the third antimicrobial agent in accordance with the present invention to have the silver-chloro complex salts in the silver concentration of 0.08 g/l, and polyaluminium chloride as the chloride in accordance with the present invention in the $AlCl_3$ equivalent concentration of 133 g/l.

Then, presence or absence of white crystals on the surface of the target object after antimicrobial treatment by the antimicrobial agent was examined by the foregoing confirmatory method. The results are shown in Table 12.

Comparative Example 25

The same operations as in Example 20 were performed to obtain a comparative antimicrobial agent except that the aqueous solution was prepared to have the silver-chloro complex salts in the silver concentration of 0.50 g/l and the sodium chloride of 330 g/l.

Then, presence or absence of white crystals on the surface of the target object after antimicrobial treatment by the antimicrobial agent was examined by the foregoing confirmatory method. The results are shown in Table 12.

Then, the deodorant effect of the antimicrobial agent with respect to the potato juice was confirmed by the foregoing confirmatory method. The results are shown in Table 13.

Further, the antimicrobial effect of the antimicrobial agent with respect to MRSA was examined by the foregoing antimicrobial property test. The results are shown in Table 14.

Also, the antimicrobial effect of the antimicrobial agent with respect to MRSA was examined by the foregoing antimicrobial treatment effect test by spraying. The results are shown in Table 15.

Comparative Example 26

The same operations as in Example 20 were performed to obtain a comparative antimicrobial agent except that the aqueous solution was prepared to have the silver-chloro complex salts in the silver concentration of 0.50 g/l and the ammonium chloride of 250 g/l.

Then, presence or absence of white crystals on the surface of the target object after antimicrobial treatment by the antimicrobial agent was examined by the foregoing confirmatory method. The results are shown in Table 12.

Further, the antimicrobial effect of the antimicrobial agent with respect to MRSA was examined by the foregoing antimicrobial property test. The results are shown in Table 14.

Also, the antimicrobial effect of the antimicrobial agent with respect to MRSA was examined by the foregoing antimicrobial treatment effect test by spraying. The results are shown in Table 15.

Comparative Example 27

The same operations as in Example 20 were performed to obtain a comparative antimicrobial agent except that the aqueous solution was prepared to have the silver-chloro complex salts in the silver concentration of 0.08 g/l and the sodium chloride of 330 g/l.

Then, presence or absence of white crystals on the surface of the target object after antimicrobial treatment by the antimicrobial agent was examined by the foregoing confirmatory method. The results are shown in Table 12.

Comparative Example 28

The same operations as in Example 20 were performed to obtain a comparative antimicrobial agent except that the aqueous solution was prepared to have the silver-chloro complex salts in the silver concentration of 0.08 g/l and the ammonium chloride of 250 g/l.

Then, presence or absence of white crystals on the surface of the target object after antimicrobial treatment by the antimicrobial agent was examined by the foregoing confirmatory method. The results are shown in Table 12.

TABLE 12

| | CONCENTRATION OF SILVER-CHLORO COMPLEX SALTS (g SILVER/l) | TYPE OF CHLORIDE | CONCENTRATION OF CHLORIDE (g/l) | PRESENCE OR ABSENCE OF WHITE CRYSTALS | |
|---|---|---|---|---|---|
| | | | | UNDILUTED SOLUTION | 100 TIMES DILUTED SOLUTION |
| EXAMPLE 20 | 0.13 | POLYALUMINIUM CHLORIDE | 100[1] | ABSENT | ABSENT |
| EXAMPLE 21 | 0.08 | BENZALKONIUM CHLORIDE | 100 | ABSENT | ABSENT |
| EXAMPLE 22 | 0.08 | POLYALUMINIUM CHLORIDE | 133 | ABSENT | ABSENT |
| COMPARATIVE EXAMPLE 25 | 0.50 | SODIUM CHLORIDE | 330 | PRESENT | PRESENT |
| COMPARATIVE EXAMPLE 26 | 0.50 | AMMONIUM CHLORIDE | 250 | PRESENT | PRESENT |
| COMPARATIVE EXAMPLE 27 | 0.08 | SODIUM CHLORIDE | 330 | PRESENT | PRESENT |
| COMPARATIVE EXAMPLE 28 | 0.08 | AMMONIUM CHLORIDE | 250 | PRESENT | PRESENT |

[1]EQUIVALENT VALUE TO THE AMOUNT OF MONOMER $AlCl_3$

Further, the permeability of the antimicrobial agent with respect to the target object was confirmed by the foregoing permeability confirmatory test for the antimicrobial agent. The results are shown in Table 16.

As is clear from the results of Table 12, in the antimicrobial treatment using the third antimicrobial agent in accordance with the present invention including polyaluminium chloride or benzalkonium chloride as the chloride, no white crystal but a transparent residue of an irregular shape was observed. Such a residue did not cause the surface of the target object to have a rough feel or deposition of crystals such as white crystals, and it was considered to be the chloride which was existing in the supersaturated state. Thus, it can be seen that the antimicrobial treatment by the antimicrobial agent of the present invention does not spoil the appearance or feel of the target object. In contrast, in the case where the antimicrobial agents of Comparative Examples 25 to 28 including sodium chloride or ammonium chloride were used, white crystals deposited on the surface of the target object, thus spoiling the appearance or feel.

TABLE 13

| | AMOUNT OF ANTIMICROBIAL | EVALUATION VALUES OF SENSORY TEST (AVERAGE VALUE) | | | |
|---|---|---|---|---|---|
| | AGENT ADDED (mg SILVER/l) | 3 DAYS | 7 DAYS | 14 DAYS | 21 DAYS |
| EXAMPLE 20 | 0.2 | 5.0 | 5.0 | 4.8 | 4.2 |
| | 1.0 | 5.0 | 5.0 | 5.0 | 5.0 |
| | 5.0 | 5.0 | 5.0 | 5.0 | 5.0 |
| COMPARATIVE EXAMPLE 25 | 0.2 | 5.0 | 3.8 | 3.2 | 2.4 |
| | 1.0 | 5.0 | 4.2 | 3.4 | 3.0 |
| | 5.0 | 5.0 | 4.7 | 3.9 | 3.5 |
| NO ADDITION | 0.0 | 3.5 | 2.4 | 1.3 | 1.0 |

It can be seen from the results of Table 13 that the potato juice after antimicrobial treatment by the third antimicrobial agent in accordance with the present invention including the polyaluminium chloride did not display any odor even after 21 days by the addition in the silver ion concentration of not less than 1.0 mg/l. Thus, it can be seen that the third antimicrobial agent in accordance with the present invention including polyaluminium chloride can demonstrate superior antimicrobial properties compared with the conventional antimicrobial agents.

TABLE 14

| | AMOUNT OF ANTIMICROBIAL | NUMBER OF BACTERIA (CFU/ml) | | | |
|---|---|---|---|---|---|
| | AGENT ADDED (mg SILVER/l) | AFTER 1 MINUTE | AFTER 10 MINUTES | AFTER 1 HOUR | AFTER 24 HOURS |
| EXAMPLE 20 | 0.1 | $3.2 \times 10^5$ | $5.1 \times 10^3$ | $1.3 \times 10^2$ | 0.0 |
| EXAMPLE 21 | 0.1 | 0.0 | 0.0 | 0.0 | 0.0 |
| COMPARATIVE EXAMPLE 25 | 0.1 | $7.3 \times 10^5$ | $7.1 \times 10^5$ | $2.4 \times 10^5$ | 0.0 |
| COMPARATIVE EXAMPLE 26 | 0.1 | $6.6 \times 10^5$ | $6.9 \times 10^5$ | $8.7 \times 10^4$ | 0.0 |
| NO ADDITION | 0.0 | $6.8 \times 10^5$ | $7.2 \times 10^5$ | 6.6 × | |

TABLE 15

| | AMOUNT OF ANTIMICROBIAL AGENT ADDED (mg SILVER/l) | NUMBER OF BACTERIA (CFU/ml) |
|---|---|---|
| EXAMPLE 21 | 1.0 | 0.0 |
| EXAMPLE 25 | 1.0 | 0.0 |
| COMPARATIVE EXAMPLE 26 | 1.0 | 0.0 |
| NO ADDITION | 0.0 | $4.6 \times 10^5$ |

Further, as it can be seen from the results of Table 14 and Table 15, the third antimicrobial agent in accordance with the present invention has the antimicrobial properties after 24 hours from the start of the antimicrobial treatment with respect to MRSA, and in the antimicrobial treatment by spraying, the number of bacteria was reduced to 0.0 CFU/ml, thus showing superior antimicrobial properties. Also, as is clear from the results of Table 14, the third antimicrobial agent in accordance with the present invention can reduce the number of bacteria immediately after the start of antimicrobial treatment with respect to MRSA. This shows that the third antimicrobial agent in accordance with the present invention has the antimicrobial properties of superior immediate action, i.e., superior disinfecting ability compared with the antimicrobial agents of Comparative Examples 25 and 26. In particular, the third antimicrobial agent in accordance with the present invention including benzalkonium chloride as the chloride is especially superior in immediate action.

TABLE 16

| | DILUTION FACTOR (TIMES) | DIAMETER OF DROPLET (mm) | SURFACE TENSION (dyn/cm) |
|---|---|---|---|
| EXAMPLE 21 | 100 | 12.8 | 30.4 |
| COMPARATIVE EXAMPLE 25 | 100 | 7.2 | 71.6 |
| WATER | — | 7.1 | 72.7 |

It can be seen from the results of Table 16 that in the third antimicrobial agent in accordance with the present invention including benzalkonium chloride as the chloride, the diameter of the droplet dropped on the petri dish is larger than that of the antimicrobial agent of Comparative Example 25 or water, and the surface tension is lower. This shows that the third antimicrobial agent in accordance with the present invention including benzalkonium chloride has higher permeability with respect to the target object compared with the conventional antimicrobial agents.

The following will describe a fourth antimicrobial agent in accordance with the present invention in detail.

The antimicrobial agent of the prior application (Tokukaihei 10-182326) includes the silver-chloro complex salts.

However, the antimicrobial agent of the prior application is produced first by preparing an aqueous solution which contains chlorides of ammonium chloride, alkali metal, or alkali earth metal as the chloride ion, and then by adding the silver chloride or silver metal in the aqueous solution and dissolving it therein as the silver-chloro complex salts. Thus, the foregoing antimicrobial agent is produced, stored, and used in the form of a solution, i.e., a liquid. Therefore, the foregoing antimicrobial agent cannot be stored or used in a solid state by mixing it with a powder such as a powder detergent.

Further, since the antimicrobial agent of the prior application is not solid, it cannot be used in the form of fine particles by pulverizing it. Namely, in manufacture of various industrial products or home appliances made from resin or fiber, etc., it is difficult to contain the antimicrobial agent in the resin or fiber by first pulverizing and then kneading the antimicrobial agent.

In general, antimicrobial agents which include the silver-chloro complex salts have sustained antimicrobial properties and the superior property of retaining the antimicrobial properties even when, for example, the surface of the target object is covered with dirt, etc., or washed repeatedly. However, since the antimicrobial agent of the prior application is in the liquid form, it is difficult to contain the antimicrobial agent in the target object, for example, by kneading, thus limiting the use.

In order to solve the foregoing problems, a fourth antimicrobial agent in accordance with the present invention includes the silver-chloro complex salts and the chloride for supplying chloride ion to stabilize the silver-chloro complex salts, and is in the solid form.

The silver-chloro complex salts included in the fourth antimicrobial agent in accordance with the present invention are not particularly limited as long as it is a salt having the complex ion structure as represented by the foregoing structural formula (1). Also, the counter ion (cation) is selected according to use and is not particularly limited.

The chloride included in the fourth antimicrobial agent in accordance with the present invention, which supplies chloride ion to stabilize the silver-chloro complex salts may be, for example, various chlorides as exemplified as the chlorides of the first antimicrobial agent.

The ratio of the silver-chloro complex salts to the chloride for supplying chloride ion in accordance with the present invention is not particularly limited as long as it is in a predetermined range which allows the antimicrobial agent to effect the antimicrobial properties without generating the silver chloride by the silver-chloro complex salts which became unstable, but a range which would make the proportion of the silver-chloro complex salts higher than the weight ratio of $1:10^8$ is preferable. The proportion of the silver-chloro complex salts below this range is not preferable since the amount of antimicrobial agent added needs to be increased in this case and due to the fact that the concentrations of the chloride and other ingredients need to be diluted to have a practical range, which necessitates diluting the antimicrobial agent to have a significantly low silver-chloro complex salt concentration. More specifically, the weight ratio in a range of $1:10^5$ to 1:10 is preferable, and a range of 1:1000 to 1:50 is more preferable, and a range of 1:200 to 3:200 is further preferable. Note that, when the proportion of the silver-chloro complex salts exceeds the foregoing ranges, the silver-chloro complex salts may become unstable.

In the case of using the fourth antimicrobial agent in accordance with the present invention, for example, by containing it in a powder detergent, etc., the mixed ratio of the antimicrobial agent is not particularly limited and it is suitably set according to potency such as the cleansing ability, etc., of the detergent, and type or amount of the target object. For example, when the antimicrobial agent is used by containing it in a powder detergent and diluting it 100 times in washing, the proportion is to fall in a range which would maintain the antimicrobial properties in use, and a range of 0.001 to 10 percent by weight is preferable, and a range of 0.01 to 2 percent by weight is further preferable in pure silver content. Note that, in this case, in order to effect superior sanitizing and antimicrobial properties in washing, the concentration of the antimicrobial agent in the cleansing solution is preferably not less than 0.01 ppm in the silver concentration.

The fourth antimicrobial agent in accordance with the present invention may include other solid components as required in addition to the silver-chloro complex salts and the chloride.

The powder which can be used by adding and mixing the fourth antimicrobial agent in accordance with the present invention is not particularly limited as long as the powder requires antimicrobial properties in use, and it includes, in addition to the powder detergent, for example, a laundry supplement, surfactant, enzyme, fluorescent brightener, anti-resoiling agent, bleaching agent, foam stabilizer, foam inhibitor, softening agent, solubilizer, thickener, emulsifier, perfume, and pigment, etc., of all powdery forms.

Also, the powder which is used by adding and mixing the antimicrobial agent therein may further include an antiseptic agent or disinfectant having antimicrobial properties. Further, the fourth antimicrobial agent in accordance with the present invention may also be added and mixed with other solid substances such as a solid soap, in addition to the powder.

The fourth antimicrobial agent in accordance with the present invention may be added to and mixed with the foregoing powders, etc., for example, by directly adding and homogeneously mixing the antimicrobial agent, after preparing its pulverulent, with the powder by stirring with a mixer. etc., or by adding the antimicrobial agent in advance to a solution dissolving a powder such as a detergent, and then drying by evaporation, etc.

The fourth antimicrobial agent in accordance with the present invention, being a solid, can be used to obtain, for example, antimicrobial resin or antimicrobial fiber by kneading it with resin or fiber. The method of kneading the fourth antimicrobial agent in accordance with the present invention, for example, with resin or fiber is not particularly limited, and it may be performed, for example, by pulverizing the fourth antimicrobial agent in accordance with the present invention into fine particles, which are then mixed with a raw material in manufacture of resin or fiber.

With the fourth antimicrobial agent in accordance with the present invention, antimicrobial treatment of various target objects is possible. The target object which can be subjected to the antimicrobial treatment of the fourth antimicrobial agent in accordance with the present invention includes various industrial products and home appliances which use the raw materials of resin, fiber, paper, and leather, etc., building materials such as a concrete wall or floor, and ceramic products. The antimicrobial agent is to be effected on the target objects themselves, and as such, the target objects include those objects, for example, such as cosmetics or builder of in the form of a powder on which the antimicrobial properties are effected by adding and mixing the fourth antimicrobial agent in accordance with the present invention.

The target object may be treated by the fourth antimicrobial agent in accordance with the present invention, for example, by washing the target object with a powder detergent or powder laundry supplement, etc., which includes the fourth antimicrobial agent in accordance with the present invention in the particle form, or by containing the fourth antimicrobial agent in accordance with the present invention which has been pulverized in resin or fiber by kneading in manufacture of the target object made of resin or fiber.

A producing method of the fourth antimicrobial agent in accordance with the present invention includes a step (first step) of preparing a mixture by mixing the silver and/or silver compound, chloride, and water, and a step (second step) of removing water from the mixture.

Specifically, the producing method of the fourth antimicrobial agent in accordance with the present invention includes, for example, (1) a method in which an aqueous liquid mixture is prepared by mixing the silver and/or silver compound, chloride, and water, and then water is removed from the aqueous solution by evaporation, and (2) a method in which water is added to the silver and/or silver compound and the chloride in the amount which can make a paste of the silver and/or silver chloride and the chloride by wetting, and then after preparing a homogenous mixture by mixing, water is removed from the mixture by evaporation.

With the method (2) of the two methods as exemplified above, the silver-chloro complex salts can be prepared by the reaction in a paste state, i.e., in the solid phase state, without taking the aqueous liquid form. According to the method (2), the amount of chloride which contributes to stabilizing the silver-chloro complex salts can be increased compared with the method (1) which takes the aqueous liquid form, thus having the advantage of increasing the concentration of the silver-chloro complex salts compared with the method (1). Further, in the method (2), since it does not require an anticorrosive concentrator which is required for removing water from the aqueous solution in the method (1), there is an advantage of reducing the manufacturing cost. Thus, in the foregoing two methods, the method (2) is more preferable.

The silver mixed in the first step is a silver metal.

Further, as the silver compound mixed in the first step, for example, other than silver chloride, any silver compounds may be used, except silver salts such as silver sulfide, silver selenide, silver telluride, silver iodide, and silver bromide, which have lower solubility than silver chloride. In industrial applications, as the silver and silver compound, it is further preferable to mix the silver salts. Further, among the silver salts, silver chloride is more preferable.

In the first step, the concentration of the silver and/or silver chloride in the aqueous solution, for example, when the mixture takes the aqueous form as in the method (1) is not particularly limited.

Further, even though the concentration of the chloride in the aqueous solution when the mixture takes the aqueous form as in the method (1) is not particularly limited, a range of 1 to 40 percent by weight is preferable, and a range of 5 to 30 percent by weight is more preferable, and a range of 10 to 20 percent by weight is further preferable.

On the other hand, when the mixture takes the paste form, for example, as in the method (2), the proportions of silver and/or silver compound, chloride, and water are not particularly limited as long as they are within a range by which the advantages of the method (2) can be obtained; however, the proportion of chloride is preferably in a range of not less than 1.3 in weight ratio when the weight ratio of the silver and/or silver compound is 1. Also, the proportion of water is preferably in a range of 10 to 100 in weight ratio when the weight ratio of the silver and/or silver compound is 1.

The working temperature of the first step is not particularly limited but a range of 60 to 110° C. is further preferable. Further, the working temperature in the second step is not particularly limited but a range of 20 to 200° C. is further preferable.

The order of mixing the silver and/or silver chloride, chloride, and water in the first step is not particularly limited, and, for example, it may be performed by dissolving the chloride in an aqueous solution and adding and mixing the silver and/or silver compound therewith, or by adding and mixing the silver and/or silver compound with a mixture of the chloride and water which has been prepared beforehand, which is then further added and mixed with another mixture of the chloride and water.

When the mixture is obtained in the aqueous liquid form, water may be removed from the mixture in the second step by concentrating the mixture under reduced pressure at room temperature or under applied heat using, for example, a rotary vacuum evaporator, and then evaporating the mixture to desiccate it by drying at room temperature or under applied heat. Further, when the mixture is obtained in the paste form, the mixture may be evaporated to desiccate it by drying at room temperature or under applied heat.

According to the fourth antimicrobial agent in accordance with the present invention, the water-soluble silver-chloro complex salts having a sustained antimicrobial property can be produced by the reaction of the silver and/or silver compound with the chloride at a predetermined ratio in the first step. Further, the chloride has the function of stabilizing the product silver-chloro complex salts. Further, in the second step, the fourth antimicrobial agent in accordance with the present invention can be obtained in a solid form by removing water from the mixture.

The following will explain the mechanism by which the silver-chloro complex salts included in the fourth antimicrobial agent in accordance with the present invention demonstrate the antimicrobial properties with respect to the target object, and the mechanism by which the chloride acts on the silver-chloro complex salts included in the fourth antimicrobial agent in accordance with the present invention.

Generally, complex salts of silver ion demonstrate the antimicrobial properties on bacteria of various species and molds by the presence of silver as the central atom. Among such complex salts, the silver-chloro complex salts, unlike thiocyanic acid complex salt of silver or thiosulfuric acid, etc., do not include sulfide ion ($S^{2-}$). Thus, the silver-chloro complex salts do not generate a toxic gas by being decomposed by heat or acid, and do not blacken by forming silver sulfide, and therefore have the sustained antimicrobial property. That is, the silver-chloro complex salts demonstrate the antimicrobial property on the target object in the form of the silver-chloro complex salts, or silver chloride, or silver metal.

In the case of using the fourth antimicrobial agent in accordance with the present invention, for example, for laundry by including it in a powder detergent, since the antimicrobial agent is diluted with water, the concentration of the chloride surrounding the silver-chloro complex salts is reduced. With decrease in concentration of the chloride, the silver-chloro complex salts become unstable and deposit in the form of fine particles of the silver chloride. Because the surface energy of the surface of fiber products, etc., is high, the fine particles of the silver chloride thus deposited are absorbed on the surface in large number, thereby demonstrating the antimicrobial properties. Note that, there may be cases where crystals grow from the crystal of the absorbed silver chloride acting as the nucleus, but a size of the crystal in this case is around 1 μm.

Further, in the case where the fourth antimicrobial agent in accordance with the present invention is, for example, kneaded with resin or fiber, the fine particles of the silver chloride which dissolved out of the fiber are absorbed again on the fiber surface and the antimicrobial properties are effected on the fiber surface. This phenomenon can be observed by electron microscope photography, etc. Further, the antimicrobial properties of the fine particles of the silver chloride which were absorbed again on the fiber surface are not lost even when washed with water and are stable.

Further, with the producing method of the fourth antimicrobial agent in accordance with the present invention, the silver-chloro complex salts can be formed by mixing the silver and/or silver compound with the chloride in the paste form using a small amount of water, for example, without taking the aqueous form. This allows the amount of chloride which contributes to stabilizing the silver-chloro complex salts to be suitably set within a range which can inhibit conversion of the silver-chloro complex salts into silver chloride, thus further stabilizing the product silver-chloro complex salts. Further, compared with the antimicrobial agent of the solution form, the amount of the product silver-chloro complex salts can be increased.

As described, the fourth antimicrobial agent in accordance with the present invention includes the silver-chloro complex salts and the chloride for stabilizing the silver-chloro complex salts, and is in a solid form. The antimicrobial agent, being a solid, can be used, for example, by mixing it with a powder such as a powder detergent, or by kneading it in the form of fine particles with resin or fiber, thus having wide use. Further, by including the chloride for stabilizing the silver-chloro complex salts, stable antimicrobial properties can be obtained.

Further, by setting a ratio of the silver-chloro complex salts to chloride in a range of 1:1000 to 1:50 in weight ratio, a further stable solid antimicrobial agent can be obtained and the content of the silver-chloro complex salts can be increased, thus improving the antimicrobial properties compared with the antimicrobial agent of a solution form.

According to the producing method of the fourth antimicrobial agent in accordance with the present invention, the solid antimicrobial agent can be obtained by removing water from the mixture which has produced the silver-chloro complex salts from the silver and/or silver compound, chloride, and water. Thus, it is possible to obtain the antimicrobial agent having wide use, for example, which can be used by mixing it with a powder such as a powder detergent, or by kneading it in the form of fine particles with resin or fiber, etc. Further, since the silver-chloro complex salts produced in the mixture have the sustained antimicrobial property and the chloride stabilizes the silver-chloro complex salts. It is possible to obtain the antimicrobial agent having stable antimicrobial properties.

The following will describe the fourth antimicrobial agent in accordance with the present invention and the producing method thereof in more detail based on Examples, which however are not to limit the present invention in any ways. Note that, the counting method of bacteria and the composition of a powder detergent in Example 24 are as follows.

<Bacteria Number Counting Method>

The number of MRSA in a solution was counted by the following method.

A solution, or a diluted solution which has been diluted with 1/1000 diluted triptosoya.bouillon (provided by NISSUI PHARMACEUTICAL Co., Ltd.) was prepared. 1 ml of the solution or diluted solution was placed on a petri dish having a diameter of 9 cm. Then, 20 ml of a standard agar medium (provided by NISSUI PHARMACEUTICAL Co., Ltd.) which had been sterilized using an autoclave and then cooled to 40° C. was put in each petri dish. After sufficient stirring, the medium was allowed to age and solidify. After incubating the petri dish for 24 hours at 37° C., the number of colonies was counted to calculate the number of bacteria in the solution.

<Composition of Powder Detergent>

To prepare a detergent composition containing the antimicrobial agent, a powder detergent having the following composition was used.

| dodecylbenzenesulfonic acid | 15 percent by weight |
|---|---|
| sodium tripolyphosphate | 17 percent by weight |
| sodium silicate | 10 percent by weight |
| sodium carbonate | 3 percent by weight |
| carboxymethyl cellulose | 1 percent by weight |
| sodium sulfate | 54 percent by weight |

EXAMPLE 23

The fourth antimicrobial agent in accordance with the present invention was prepared using the producing method of the fourth antimicrobial agent in accordance with the present invention in which the mixture takes the aqueous solution form in the first step.

933 g of potassium chloride was dissolved in water to prepare 3 l of an aqueous solution in total weight. Then, 2.43 g of wet silver chloride (containing equivalent to 1.5 g of pure silver) was stirred, dispersed, and dissolved in the aqueous solution to prepare a mixture as an aqueous solution of the silver-chloro complex salts. The aqueous solution was then concentrated under reduced pressure at 80° C. using a rotary vacuum evaporator to obtain a concentrated slurry. The concentrated slurry was dried in air for 8 hours at 105° C. The weight of the dried product after drying was 936 g. The dried product showed no change in color even when exposed to direct sun light for 10 minutes or longer, thus confirming that no silver chloride resided in the dried product. The dried product was obtained as the fourth antimicrobial agent in accordance with the present invention in a solid form.

EXAMPLE 24

The fourth antimicrobial agent in accordance with the present invention was produced by the producing method of the fourth antimicrobial agent in accordance with the present invention in which the mixture does not take the aqueous solution form in the first step.

20 g of potassium chloride was made into a powder and 3.4 ml of water was added and mixed therewith to have a paste form. Then, 2.6 g of wet silver chloride (containing equivalent to 1.6 g of pure silver) was added and mixed to obtain a homogenous mixture (A). Then, 980 g of potassium chloride and 60 ml of water were added and homogeneously mixed in another container, to which was then added the mixture (A), which was mixed therein to obtain a homogenous mixture (B). A portion of the mixture (B) was collected and exposed to the sun light and the mixture (B) immediately turned to a blue-purple color, thus confirming the presence of silver chloride which had not been changed to the silver-chloro complex salts at the time the collection was made. Thus, the mixture (B) was further dried in air for 8 hours at 105° C. The weight of the dried product recovered after drying was 1003 g. The dried product did not show any change in color even when exposed under direct sun light for 10 minutes or longer, thus confirming that no silver chloride resided. This confirmed formation of the silver-chloro complex salts in a solid phase without taking the aqueous solution form. The dried product was obtained as the fourth antimicrobial agent in accordance with the present invention in a solid form. The antimicrobial agent contained the silver-chloro complex salts in the silver concentration of 1595 mg/kg ($1.595 \times 10^{-3}$ percent by weight), and potassium chloride as the remainder of the silver-chloro complex salts.

Antimicrobial treatment was applied on a cloth by the detergent composition which was prepared by adding and mixing the antimicrobial agent powder with a powder detergent having the foregoing composition.

To a 1 l beaker were placed 30 sheets of cloth made of polyacetate, each having a size of 1.8 cm×1.8 cm. After adding 500 ml of water to the beaker, a detergent composition which was prepared by mixing 50 mg of the antimicrobial agent and 500 mg of the powder detergent was further added, which was then washed for 5 minutes while rotating it. Then, the pieces of cloth were transferred to another beaker containing 500 ml of the antimicrobial agent, which was then rinsed for 5 minutes.

The pieces of cloth were taken out and placed on a sterilized petri dish, and after wind dried, each piece was independently transferred to a 50 ml centrifuge tube. The pieces of cloth were then inoculated with 0.2 ml of an MRSA suspension liquid containing MRSA in the concentration of $5 \times 10^4$/ml in a 1000 times diluted triptosoya.bouillon medium (provided by NISSUI PHARMACEUTICAL Co., Ltd.). The pieces of cloth thus inoculated were processed for 18 hours at room temperature (20 to 25° C.). To the centrifuge tube were then added 0.85 percent by weight of a common salt and 20 ml of a solution containing 0.2 percent by weight of Tween 80 (polyoxyethylene sorbitan monooleate), which was then shaken 30 times to wash out bacteria, and the number of bacteria in each solution was counted by the foregoing counting method to determine the average value for the 30 pieces of cloth.

Also, the same operations as above were performed to count the number of bacteria except that the powder detergent was 0 g.

Further, the same operations as above were performed to count the number of bacteria without using the antimicrobial agent.

Further, the same operations as above were performed to count the number of bacteria without using the antimicrobial agent and the powder detergent. The results are shown in Table 17.

TABLE 17

| ANTIMICROBIAL AGENT (mg) | POWDER DETERGENT (mg) | NUMBER OF BACTERIA |
|---|---|---|
| 50 | 500 | 0.0 |
| 50 | 0 | 0.0 |
| 0 | 500 | $4.6 \times 10^5$ |
| 0 | 0 | $4.8 \times 10^5$ |

It can be seen from the results of Table 17 that the antimicrobial treatment can be effected on cloth by washing it using the fourth antimicrobial agent in accordance with the present invention or using the detergent composition containing the fourth antimicrobial agent in accordance with the present invention. In contrast, it can be seen that in the case of washing with the powder detergent alone without the fourth antimicrobial agent in accordance with the present invention, or in the case of washing with water alone, growth of the inoculated bacteria is observed and no antimicrobial treatment is effected.

The following will describe in detail a detergent, laundry supplement, and a third antimicrobial treatment method in accordance with the present invention.

The detergent and laundry supplement in accordance with the present invention can be obtained by containing the silver-chloro complex salts in a predetermined ratio in a detergent or laundry supplement having the following compositions.

The silver-chloro complex salts are not particularly limited as long as it is a salt which can supply the complex ion structure as represented by the structural formula (1) in the aqueous solution.

Generally, complex salts of silver ion demonstrate antimicrobial properties on bacteria of various species and molds by the presence of silver as the central atom. Among such complex salts, the silver-chloro complex salts, unlike thiocyanic acid complex salt of silver or thiosulfuric acid, etc., do not include sulfide ion ($S^{2-}$) Thus, the silver-chloro complex salts do not generate a toxic gas by being decomposed by heat or acid, or do not blacken by forming silver sulfide, and therefore is stable.

Further, the silver-chloro complex salts, whether it is preserved alone or in the detergent or laundry supplement, do not become unstable by the UV light or heat, etc. Also, the silver-chloro complex salts do not generate precipitate of silver chloride even with the presence of chlorine ions which are contained in a thickening agent (described later) as the ingredient of the detergent or laundry supplement, and therefore Is very stable.

The silver-chloro complex salts used in the present invention may be included in a liquid detergent in the form of an aqueous solution, or in a liquid laundry supplement. Further, the silver-chloro complex salts may be included in a powder detergent or powder laundry supplement in the form of a solid (powder) which is obtained by evaporating the aqueous solution of the silver-chloro complex salts to dryness. Further, the silver-chloro complex salts may be included in the powder detergent or powder laundry supplement while being supported on a porus material such as zeolite.

The detergent of the present invention refers to those detergents which are composed of a surfactant, as the main component, and additives, and whose primary cleansing action is by the surfactant property. The additives contained in the detergent include, a builder, enzyme, fluorescent brightener, anti-resoiling agent, bleaching agent, foam stabilizer, foam inhibitor, softening agent, solubilizer, thickener, emulsifier, perfume, and pigment, etc. The detergent may further include an antiseptic agent or disinfectant having antimicrobial properties.

The surfactant includes, for example, anionic surfactants, such as alkylbenzenesulfonate, α-olefin-sulfonate, alkyl sulfate, polyoxyethylene alkyl sulfate, and a salt of long-chain fatty acid; and non-ionic surfactants. As the non-ionic surfactants, various non-ionic surfactants as exemplified as the surfactant used in the second antimicrobial agent in accordance with the present invention may be used.

The builder includes inorganic builders and organic builders. The organic builders may be water soluble or water insoluble. The water soluble builders may be, for example, phosphates, such as sodium tripolyphosphate, trisodium phosphate, sodium metaphosphate, and sodium pyrophosphate; silicates such as sodium silicate; carbonates, such as sodium carbonate, sodium bicarbonate, and sodium carbonate peroxyhydrate; sulfates such as sodium sulfate; and carboxylates such as sodium citrate. The water insoluble builders may be crystalline alumino sodium silicate (zeolite), etc.

The organic builders include an organic chelate builder, polymer electrolytic builder, and organic activating builder. The organic chelate builder may be, for example, aminocarboxylic acids, such as nitrilotriacetic acid (NTA), ethylenediaminetetraacetic acid (EDTA), and diethylenetriaminepentaacetic acid (DTPA), and their salts; organic acids, such as oxalic acid, tartaric acid, citric acid, gluconic acid, and their salts; cyclocarboxylic acid such as pyromellitic acid and benzopolycarboxylic acid, and their salts; and ether carboxylic acids, such as carboxymethyltartronic acid (CMT), carboxymethyloxysuccinic acid (CMOS), and 2,5-dioxa-1,1,3,4,6,6-hexanehexacarboxylic acid (TMD). The polymer electrolytic builder may be, for example, oxidized derivatives of synthetic polymer, such as acrylic acid polymer, maleic anhydride polymer, co-polymer of acrylic acid and maleic anhydride, α-hydroxyacrylic acid polymer, itaconic acid polymer, and epoxysuccinic acid polymer; oxidized derivatives of natural polymer, such as starch, cellulose, and alginic acid. The organic activating builder may be, for example, aminosulfonate.

The enzyme may be, for example, protease, lipase, amylase, and cellulase, etc. as long as its activity is not lost by the silver ion.

The fluorescent brightener may be, for example, derivatives of bis(triazinylamino)stilbene sulfonic acid, derivatives of bisstyryl biphenyl, derivatives of coumarin, derivatives of pyrazoline, and derivatives of naphthalimide.

The anti-resoiling agent may be, for example, carboxymethyl cellulose, methyl cellulose, hydroxyethyl cellulose, carboxymethyl hydroxyethyl cellulose, hydroxypropyl cellulose, hydroxybutylmethyl cellulose, polyethyleneglycol, polyvinyl alcohol, polyvinyl pyrrolidone, polyvinyl acetate (vinyl acetate polymer), co-polymer of ethylene glycol and ethylene phthalate, co-polymer of vinyl pyrrolidone and vinyl acetate, co-polymer of vinyl sulfonic acid and sodium acrylate, co-polymer of vinyl acetate and maleic anhydride, co-polymer of vinyl pyrrolidone and maleic anhydride, co-polymer of vinylsulfonic acid and maleic anhydride, and the like.

The bleaching agent may be, for example, sodium perborate, peroxyborax, sodium carbonate peroxyhydrate, sodium peroxypyrophosphate, perbenzoate, urea-hydrogen peroxide compound, melamine-hydrogen peroxide compound, citric acid perhydrate, and sodium perborate zinc phthalocyanine sulfonate, sodium perborate aluminium phthalocyanine sulfonate, and the like. Further, the activating agent of the bleaching agent may be, for example, phthalic anhydride, benzoic anhydride, N,N', N", N"'-tetraacetylglycoluril, and tetraacetylethylenediamine. Alternatively, the stabilizing agent of the bleaching agent may be magnesium silicate, calcium silicate, tin silicate, and the like.

The foam stabilizer may be, for example, diethanolamide, long-chain alcohol, amine oxide, carboxy betaine, sulfobetaine, hydroxyalkylamide, alkylsulfoxide, and the like.

The foam inhibitor may be, for example, microcrystal wax, silicone, ketones with 18 to 40 carbon atoms, and the like.

The softening agent may be cationic surfactants such as dimethylstearylammonium chloride; monoalkyldimethylamine oxide, high molecular weight polyamine, montmorillonite as the natural mineral, and the like.

When the detergent in accordance with the present invention is a liquid detergent, a solubilizer may be used for the purpose of solubilizing the silver-chloro complex salts. The solubilizer may be, for example, benzenesulfonate, toluenesulfonate, xylenesulfonate, urea, ethanolamine, diethanolamine, teiethanolamine, ethyl alcohol, ethylene glycol, propyleneglycol, polyethylene glycol, ethylbenzenesulfonic acid, isopropylbenzenesulfonate, cellosolve (ethyleneglycol monoethylether), and the like.

When the detergent in accordance with the present invention is a liquid detergent, the detergent may include a thickener. The thickener may be, for example, polymer compounds, such as maleic acid polymer, itaconic acid polymer, co-polymer of vinyl methyl ether and maleic anhydride, polypropyleneglycol, polyvinyl alcohol, hydroxyethyl cellulose, methylhydroxypropyl cellulose, and hydroxypropyl cellulose; inorganic electrolytes, such as sodium sulfide, sodium chloride, potassium chloride, and the like.

When the detergent in accordance with the present invention in a liquid detergent, the detergent may include an emulsifier. The emulsifier may be, for example, co-polymer of styrene and acrylamido, co-polymer of styrene and vinylpyrrolidone, vinyl acetate polymer, magnesium stearate, monoglycerido, ethyleneglycol monofatty acid ester, ethyleneglycol difatty acid ester, argentine, micaceous titanium, and the like.

Further, when the detergent in accordance with the present invention is a liquid detergent, the liquid detergent will also have the anticorrosive and sanitizing effects by the antimicrobial action of the silver-chloro complex salts contained therein. However, the silver-chloro complex salts may also be used together with a known anticorrosive agent and disinfectant. The anticorrosive agent or disinfectant may be dehydroacetic acid and its salt, sorbic acid and its salt, isobutyl p-hydroxybenzoate, isopropyl p-hydroxybenzoate, ethyl p-hydroxybenzoate, butyl p-hydroxybenzoate, n-propyl p-hydroxybenzoate, butylhydroxyanisole, butylhydroxytoluene, and the like.

The types of perfume and pigment are not particularly limited.

As the term is used herein, the "laundry supplement" in accordance with the present invention refers to those supplements which are used before, during, or after washing for the purpose of enhancing the cleansing ability of the detergent, or, for the purpose of applying other treatment on, for example, fiber products, other than washing. The other treatment includes, for example, bleaching, brightening, softening, sizing, and removal of alkali component. The laundry supplement of the present invention includes, for example, a presoak, water softening agent, pre-treatment agent, bleaching agent, brightener, souring agent, softening agent, sizing agent, and the like. The laundry supplement may further include a builder, enzyme, fluorescent brightener, anti-resoiling agent, bleaching agent, foam stabilizer, foam inhibitor, softening agent, solubilizer, thickener, emulsifier, perfume, and pigment, etc, which are contained as the detergent component in accordance with the present invention. The laundry supplement of the present invention may further include the sanitizing agent and the antimicrobial agent.

Further, as the bleaching agent contained in the laundry supplement in accordance with the present invention, other than the bleaching agents as exemplified above, hypochlorite such as sodium hypochlorite, and/or chlorite such as sodium chlorite can be used. That is, the silver-chloro complex salts included in the laundry supplement in accordance with the present invention are stable even in the presence of chloride ion. Thus, the laundry supplement in accordance with the present invention can be used combining the bleaching agent containing hypochlorite and/or chlorite, i.e., a so-called chlorine-containing bleaching agent, and the silver-chloro complex salts. As a result, it is possible to have the bleaching effect as well as the antimicrobial effect on the target object by the antimicrobial properties of the silver-chloro complex salts.

According to the third antimicrobial treatment in accordance with the present invention, the washing target object (target object) such as fiber products are treated in a solution containing the silver-chloro complex salts. The solution is preferably a cleansing solution containing the silver-chloro complex salts and the surfactant. This allows the target object to be subjected to the antimicrobial treatment as well as washed. That is, the solution preferably includes the silver-chloro complex salts in a cleansing solution containing at least the surfactant and, as required, the laundry supplement, etc.

The method of adding the silver-chloro complex salts in the cleansing solution is not particularly limited as long as the sanitizing and antimicrobial effect is effected on the washing target object. For example, it is possible to adopt a method of directly putting into the cleansing solution, a method of spraying onto the washing target object in advance, a method of soaking the washing target object in advance in a liquid containing the silver-chloro complex salts, a method of mixing the silver-chloro complex salts beforehand in the detergent or laundry supplement as a component thereof, and the like.

Further, the silver-chloro complex salts may be added to the cleansing solution at any time between start and end of washing. Note that, a dewatering process may be performed in washing.

The mixed ratio of the silver-chloro complex salts contained in the detergent to laundry supplement in accordance with the present invention is not particularly limited, and the silver-chloro complex salts are added in a range which would sustain the antimicrobial properties when used by being diluted several tens to several thousand times during washing, etc. In order to effect superior disinfecting and antimicrobial properties, a silver concentration of not less than 0.1 ppm is preferable.

The concentration of the detergent and laundry supplement in accordance with the present invention in the cleansing solution is not particularly limited as long as it is within a range by which the disinfecting and antimicrobial properties are effected at the time of washing. However, in order to effect the antimicrobial properties sufficiently, the silver ion concentration of not less than 0.01 ppm in the cleansing solution is preferable. Further, when washing the same washing target object repeatedly, the antimicrobial effect can be obtained at lower concentrations.

The following explains the mechanism by which the silver-chloro complex salts in accordance with the present invention demonstrate the antimicrobial properties on products.

The silver-chloro complex salts are diluted with water when used in washing, etc., and thus the concentration of the chloride ion decreases. With decrease in chloride ion concentration, the silver-chloro complex salts become unstable and deposit in the form of fine particles of the silver chloride. Because the surface energy of the surface of fiber products, etc., is high, the fine particles of the silver chloride thus deposited are absorbed on the surface in large number. Note that, there may be cases where crystals grow from the crystal of the absorbed silver chloride acting as the nucleus, but the size of the crystal in this case is around 1 μm.

Thus, when washing the washing target object, the silver-chloro complex salts are added to the cleansing solution, and then the washing target object is rinsed as required to fix or anchor the fine particles of the silver chloride on its surface, thereby having the antimicrobial effect on the washing target object.

In this case, the crystals of the silver chloride which was absorbed on the surface and elsewhere of the washing target object are markedly fine particles and thus the surface area is large. As a result, the silver ion easily dissolves out and superior antimicrobial properties are effected. Further, since the silver chloride absorbed on the fiber surface is markedly fine particles, it does not blacken by irradiation of the UV light to the level which can be observed by an naked eye.

As described, by utilizing the properties of the silver-chloro complex salts contained in the detergent and laundry supplement in accordance with the present invention, the sanitizing and antimicrobial effects can be easily obtained on the washing target object at the same time as washing while sustaining the antimicrobial properties on the washing target object.

The detergent and laundry supplement in accordance with the present invention can be applied to fibers such as wool, silk, polyamide, polyurethane, and the like. Further, the applicable fibers may be colored.

The following describes the detergent, laundry supplement, and third antimicrobial treatment method in accordance with the present invention in more detail based on Examples and Comparative Examples without limiting the present invention in any ways. Note that, the detergent aqueous solution and the bacteria number counting method in the Examples and Comparative Examples are as follows.

<Detergent Aqueous Solution>

| | |
|---|---|
| dodecylbenzenesulfonic acid | 20% by weight |
| dodecylpolyoxyethylene ether | 7% by weight |
| sodium m-xylenesulfonate | 6% by weight |
| triethanolammonium citrate | 10% by weight |
| water | 57% by weight |

A aqueous solution containing 0.1 percent by weight of the aqueous solution of the foregoing composition and the silver-chloro complex salts and/or sodium hypochlorite in a predetermined concentration was used as the detergent aqueous solution in the following laundry processes.

<Bacteria Number Counting Method>

The number of bacteria in the solution (cleansing solution, rinsing solution) was counted by the method of Example 24.

EXAMPLE 25

Disinfection of cloth by the silver-chloro complex salts was performed in the following manner.

In a centrifuge tube with a volume of 50 ml was placed a piece of cloth having a size of 1.8 cm×1.8 cm, and the tube was sterilized by an autoclave. The cloth was then inoculated by collecting and placing thereon 0.2 ml of a suspension liquid containing $5 \times 10^4$/ml of MRSA in a 1000 times diluted triptosoya.bouillon medium.

To the centrifuge tube was then added 20 ml of a detergent aqueous solution containing 1.0 ppm of the silver-chloro complex salts. The cloth was washed for 10 minutes while rotating the centrifuge tube at 150 rpm, and the supernatant was used as the cleansing solution. Then, the cloth was transferred to another centrifuge tube containing 20 ml of sterilized water and was rinsed for 10 minutes at 150 rpm, and the supernatant was used as the cleansing solution. The cloth was then taken out and placed on a standard agar medium for incubation at 37° C. for 24 hours to confirm presence or absence of MRSA proliferation. The same operation was repeated 3 times to prepare Petri Dish 1, Petri Dish 2, and Petri Dish 3.

In the same manner, the same operation was repeated for detergent aqueous solutions containing the silver-chloro complex salts in the concentrations of 10.0 ppm and 100.0 ppm, respectively, and for a detergent aqueous solution containing 1.0 ppm of silver-chloro complex salts and 125.0 ppm of sodium hypochlorite (reagent) in the concentration of active chlorine. The results are shown in Table 18.

After washing, the number of bacteria contained in each rinsing solution was counted by the foregoing counting method. The petri dish which contained one or more bacteria was represented by "+", and the petri dish which contained no bacteria was represented by "−".

Comparative Example 29

The same operation as in Example 25 was performed without using the silver-chloro complex salts. The results are shown in Tables 18 to 20.

TABLE 18

| | SILVER-CHLORO COMPLEX SALTS (ppm IN SILVER CONCENTRATION) | SODIUM CHLORITE (ppm IN ACTIVE CHLORINE) | PRESENCE OR ABSENCE OF BACTERIA | | |
|---|---|---|---|---|---|
| EXAMPLE 25 | 1.0 | 0.0 | − | − | − |
| | 1.0 | 125.0 | − | − | − |
| | 10.0 | 0.0 | − | − | − |
| | 100.0 | 0.0 | − | − | − |
| COMPARATIVE EXAMPLE 29 | 0.0 | 0.0 | + | + | + |
| | 0.0 | 125.0 | − | − | − |

TABLE 19

| | SILVER-CHLORO COMPLEX SALTS (ppm IN SILVER CONCENTRATION) | SODIUM CHLORITE (ppm IN ACTIVE CHLORINE) | NUMBER OF BACTERIA IN CLEANSING SOLUTION |
|---|---|---|---|
| EXAMPLE 25 | 1.0 | 0.0 | $9.5 \times 10^2$ |
| | 1.0 | 125.0 | 0 |
| | 10.0 | 0.0 | $3.5 \times 10^2$ |
| | 100.0 | 0.0 | 0 |
| COMPARATIVE EXAMPLE 29 | 0.0 | 0.0 | $3.3 \times 10^4$ |
| | 0.0 | 125.0 | 0 |

TABLE 20

| | SILVER-CHLORO COMPLEX SALTS (ppm IN SILVER CONCENTRATION) | SODIUM CHLORITE (ppm IN ACTIVE CHLORINE) | NUMBER OF BACTERIA IN RINSING SOLUTION |
|---|---|---|---|
| EXAMPLE 25 | 1.0 | 0.0 | 0 |
| | 1.0 | 125.0 | 0 |
| | 10.0 | 0.0 | 0 |
| | 100.0 | 0.0 | 0 |
| COMPARATIVE EXAMPLE 29 | 0.0 | 0.0 | $1.5 \times 10^2$ |
| | 0.0 | 125.0 | 0 |

EXAMPLE 26

Antimicrobial treatment by the silver-chloro complex salts was effected on cloth in the following manner.

To a 100 ml beaker was added a piece of cloth having a size of 1.8 cm×1.8 cm. To the beaker was added 50 ml of a detergent aqueous solution containing the silver-chloro complex salts and/or sodium hypochlorite in a predetermined concentration, and the cloth was washed for 5 minutes while rotating it. The cloth was then transferred to another beaker containing 50 ml of sterilized water and rinsed for 5 minutes.

The cloth was then taken out and placed on a sterilized petri dish, and after wind dried, transferred to a 50 ml centrifuge tube. The cloth was inoculated with 0.2 ml of an MRSA suspension liquid containing $5 \times 10^4$/ml of MRSA in a 1000 times diluted triptosoya.bouillon medium, and was treated for 18 hours at room temperature (20 to 25° C.). To the centrifuge tube was added 20 ml of a solution containing 0.85% of a common salt and 0.2% of Tween 80 (polyoxyethylenesorbitan monooleate), and the bacteria was washed out by shaking the tube 30 times and the number of bacteria contained in the solution was counted by the foregoing counting method. Also, the same operation was performed except that water was used instead of the aqueous solution. The results are shown in Table 21.

Comparative Example 30

The same operation as in Example 26 was performed without using the silver-chloro complex salts. The results are shown in Table 21.

TABLE 21

| | SURFACTANT | SILVER-CHLORO COMPLEX SALTS (ppm IN SILVER CONCENTRATION) | SODIUM HYPOCHLORITE (ppm IN ACTIVE CHLORINE) | NUMBER OF BACTERIA |
|---|---|---|---|---|
| EXAMPLE 26 | ABSENT | 5 | 0.0 | 0.0 |
| | | 5 | 125.0 | 0.0 |
| | PRESENT | 5 | 0.0 | 0.0 |
| | | 5 | 125.0 | 0.0 |

TABLE 21-continued

| | SURFACTANT | SILVER-CHLORO COMPLEX SALTS (ppm IN SILVER CONCENTRATION) | SODIUM HYPOCHLORITE (ppm IN ACTIVE CHLORINE) | NUMBER OF BACTERIA |
|---|---|---|---|---|
| | ABSENT | 500 | 0.0 | 0.0 |
| | | 500 | 0.0 | 0.0 |
| COMPARATIVE EXAMPLE 30 | ABSENT | 0 | 0.0 | $1.8 \times 10^6$ |
| | | 0 | 125.0 | $2.1 \times 10^6$ |
| | PRESENT | 0 | 0.0 | $2.5 \times 10^6$ |
| | | 0 | 125.0 | $1.4 \times 10^6$ |

It can be seen from the results of Table 18 to 20 that when the silver-chloro complex salts are contained in the silver concentration of 1.0 ppm or more, no bacteria existed on the cloth after washing and rinsing, and the cloth was completely sanitized.

It can be seen from the results of Tables 18 to 20 the sodium hypochlorite also has the sanitizing effect. However, it can be seen from the result of Table 21 that when the detergent aqueous solution does not contain the silver-chloro complex salts, no antimicrobial properties were effected on the cloth after washing and growth of bacteria was observed.

Further, it can be seen from the results of Table 21 that the silver-chloro complex salts can demonstrate the antimicrobial ability regardless of presence or absence of the surfactant.

The following will describe one embodiment of disposable sheets in accordance with the present invention with reference to FIGS. 2(a) and 2(b), and FIGS. 3 through 6.

As shown in FIGS. 2(a) and 2(b), in disposable sheets 2 of the present embodiment, there are provided notches 3 with respect to and in the longitudinal direction of a rectangular sheet 2 so that the sheet 2 can be separated into a right-side part 2R and a left-side part 2L, and a tape 4 for sealing the notches 3 is stuck on the sheet 2 by a pressure sensitive adhesive agent (not shown) covering the notches 3.

The disposable sheets 1 can be used for beds of permanently-ill patients and removed only by moving it while the patient laying thereon.

Figure 3:
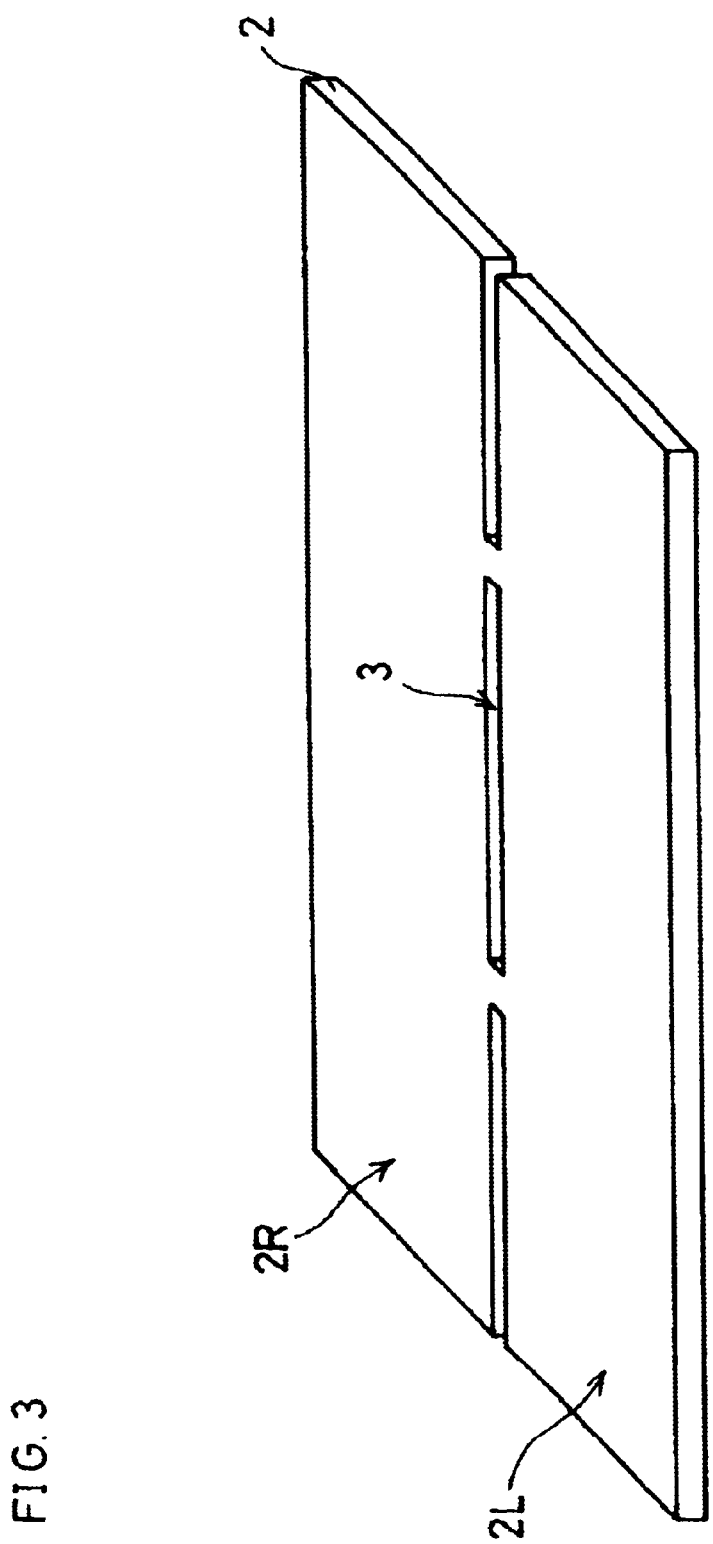
FIG. 3 is a perspective view of the disposable sheets of FIGS. 2(*a*) and 2(*b*), showing a state in which a tape is peeled off.

Specifically, in order to remove the disposable sheets 1, the body of a patient is turned to the side on the right-side part 2R (or left-side part 2L) of the sheet 2 to peel off the tape 4 sealing the notches 3. As a result, as shown in FIG. 3, the notches 3 appear. Then, by pulling hard the left-side part 2L (or right-side part 2R) of the sheet 2 with hands, the left-side part 2L (or right-side part 2R) of the sheet 2 is separated from the right-side part 2R (or left-side part 2L) at the notches 3, thus removing the left-side part 2L (or right-side part 2R) of the sheet 2. Then, the body of the patient is turned to the side from which the left-side part 2L (or right-side part 2R) of the sheet 2 was removed (e.g., on the left-side part 2L of underlying disposable sheets 1) and the right-side part 2R (or left-side part 2L) of the sheet 2 is pulled with hands to remove it.

Since the disposable sheets 1 can be removed while the patient is lying thereon, by placing another sheets under the disposable sheets 1 in advance, the sheets can be replaced while the patient is lying thereon. Accordingly, it is not required to move the patient from the bed, thus making it possible to replace sheets by a single care giver.

Further, since the notches 3 of the disposable sheets 1 are sealed with the tape 4, urine or sweat of the patient is prevented from seeping out into underlying sheets in use, for example, such as another disposable sheets 1, through the notches 3.

The size of the disposable sheets 1 is suitably adjusted according to the size of the bed to which the disposable sheets 1 are applied, and it is set to have a size of about 150 cm×220 cm (width×length), for example.

In order to prevent the sheets from becoming sultry by sweat, etc., the sheet 2 is preferably made from sheets having gas permeability such as paper or unwoven fabric, or gas permeable sheets including additives. As such gas permeable sheets, paper and unwoven fabric are particularly preferable since they are inexpensive and have some absorbency to partially absorb urine or sweat, etc.

The sheet 2 preferably further includes the antimicrobial and deodorizing agent, such as the silver-chloro complex salts, as additives. As a result, the sheet 2 can have the antimicrobial and deodorizing effects, thus maintaining further cleaner environment.

The sheet 2 preferably further includes a polymer water absorbent as additives. This ensures to absorb urine or sweat, etc., and prevents urine or sweat, etc., to seep out into the underlying sheets through the sheet 2. As such a polymer water absorbent, polymer absorbent resin in the form of fine particles, as represented by "Aquakeep 10SH-NF" (product name, provided by Sumitomo Seika Chemicals Co., Ltd.) can suitably be used.

The method of adding the additives in the gas permeable sheet is not particularly limited, and it can be performed by kneading the additives with the raw material of the gas permeable sheet in manufacture thereof ("kneading method" hereinafter), or by sandwiching the additives between the gas permeable sheet and another sheet, which are then pasted together ("sandwiching method" hereinafter), or by dissolving the additives with a binding agent to have a solution and then soaking the gas permeable sheet in the solution ("soaking method" hereinafter).

The following will describe the method of adding additives in more detail based on the example of adding the antimicrobial and deodorizing agent and polymer water absorbent.

When adding both the antimicrobial and deodorizing agent and the polymer water absorbent by the kneading method, the antimicrobial and deodorizing agent and the polymer water absorbent are added by kneading with the raw material of the gas permeable sheet in manufacture of the gas permeable sheet from its raw material such as paper or unwoven fabric.

Figure 4:
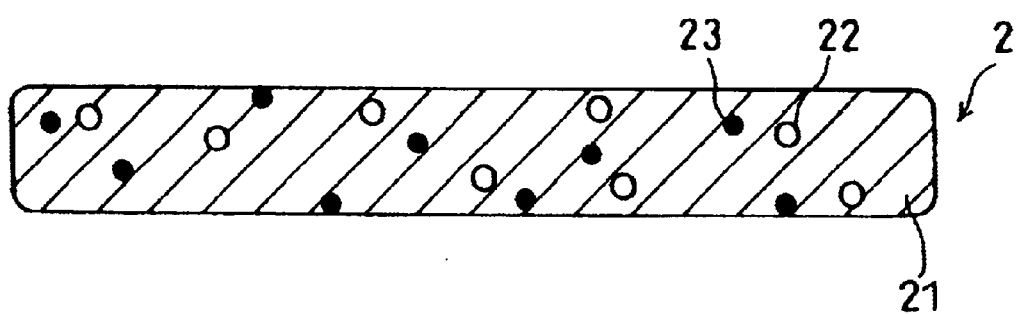
FIG. 4 is a cross sectional view showing one example of sheets used as the disposable sheets of FIGS. 2(*a*) and 2(*b*).

As a result, as shown in FIG. 4, the sheet 2 of a single layer structure in which the antimicrobial and deodorizing agent 23 and the polymer water absorbent 22 are dispersed in the gas permeable sheet 21 is obtained. In this case, as the antimicrobial and deodorizing agent 23, the antimicrobial and deodorizing agent of a powdery form, for example, such as a silver-chloro complex salt powder can be used. Also, as the polymer water absorbent 22, a polymer water absorbent of a powdery form, for example, such as polymer water absorbent resin of fine particles as represented by "Aquakeep 10SH-NF" (product name, provided by Sumitomo Seika Chemicals Co., Ltd.) can be used.

Note that, to increase the strength of the sheet 2, the sheet of the single structure in which the antimicrobial and deodorizing agent 23 and the polymer water absorbent 22 are kneaded in the gas permeable sheet 21 is integrated by bonding using an adhesive with a resin sheet made of polyethylene, polyester, polypropylene, or polyamide, or a gas permeable sheet (paper or unwoven fabric) which does not contain the antimicrobial and deodorizing agent and the polymer water absorbent. In this case, the sheet 2 come to have a double layer structure.

Further, in the case where the antimicrobial and deodorizing agent and the polymer water absorbent are added by the soaking method and the sandwiching method, respectively, the following is carried out.

That is, after manufacturing the gas permeable sheet made of paper or unwoven fabric, etc., the gas permeable sheet is soaked in a mixture of the antimicrobial and deodorizing agent and the binding agent so as to attach the antimicrobial and deodorizing agent and the binding agent (binder) on the surface of the gas permeable sheet. As a result, the antimicrobial and deodorizing agent is fixed on the surface of the gas permeable sheet by the binding agent, thereby adding the antimicrobial and deodorizing agent on the gas permeable sheet. In this case, as the antimicrobial and deodorizing agent, the antimicrobial and deodorizing agent of a liquid form, for example, such as liquid silver-chloro complex salts can be used.

Then, the gas permeable sheet adhering the antimicrobial and deodorizing agent thereon is integrated by bonding using an adhesive with a resin sheet such as polyethylene, polyester, polypropylene, and polyamide, etc., or a gas permeable sheet (paper or unwoven fabric) which does not contain the antimicrobial and deodorizing agent while sandwiching the polymer water absorbent therebetween. In this case, as the polymer water absorbent, a polymer water absorbent of a powdery form, for example, such as a polymer water absorbent powder as represented by "Aquakeep 10SH-NF" (product name, provided by Sumitomo Seika Chemicals Co., Ltd.) can be used.

Figure 5:
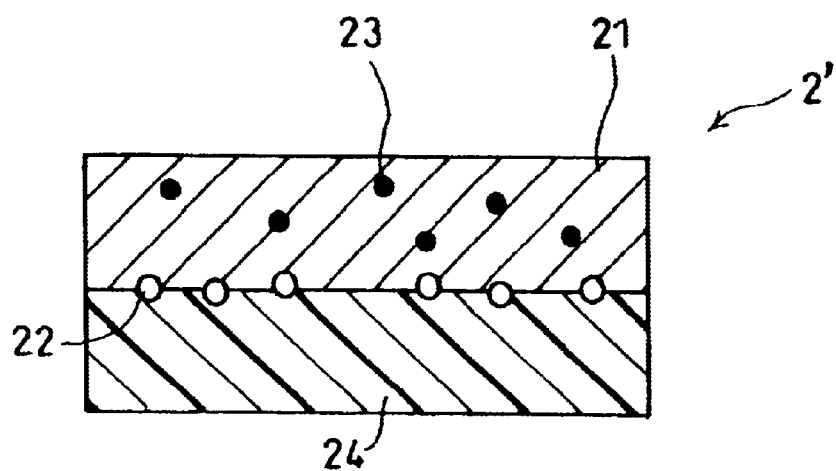
FIG. 5 is a cross sectional view showing another example of sheets used as the disposable sheets of FIGS. 2(*a*) and 2(*b*).

As a result, as shown in FIG. 5, it is possible to obtain a sheet 2' of a double layer structure wherein the polymer water absorbent 22 is sandwiched between the gas permeable sheet 21 dispersing the antimicrobial and deodorizing agent 23 therein and the sheet 24 made from a resin sheet or gas permeable sheet.

Note that, the positions of the antimicrobial and deodorizing agent and the polymer water absorbent may be changed. That is, the sheet of the double layer structure including the antimicrobial and deodorizing agent and the polymer water absorbent can also be obtained by first making a gas permeable sheet containing the polymer water absorbent and then bonding it with a resin sheet or gas permeable sheet which does not contain the polymer water absorbent using an adhesive while sandwiching the antimicrobial and deodorizing agent therebetween. In this case, as the antimicrobial and deodorizing agent, the antimicrobial and deodorizing agent of a powdery form, for example, such as the powder silver-chloro complex salts can be used.

The notches 3 are to allow the sheet 2 to be separated by pulling the sheets 2 with hands, and they can be, for example, slits or sewing pattern.

The notches 3 are preferably provided along the center line in the longitudinal direction of the sheet 2, i.e., for example, in such a manner that the distance from the longer sides of the sheet 2 to the center line is 75 cm when the width of the sheet 2 is 150 cm.

As a result, the two portions on the both sides of the notches 3 of the sheet 2, i.e., the right-side part 2R and the left-side part 2L become equal in size. As described, in order to replace the disposable sheets 1 while the patient is lying thereon, it is required to turn the patient to the right-side part 2R of the sheet 2 and then to the side of the sheets 2 from which the left-side part 2L of the sheet was removed (e.g., on the left-side part 2L of the sheet 2 of underlying disposable sheets 1). By making the right-side part 2R and the left-side part 2L equal in size, it becomes relatively easier to turn the patient to the right-side part 2R of the sheet 2, and to the portion of the sheets 2 from which the left-side part 2L of the sheet 2 was removed.

The tape 4 covering the notches 3 may be a sheet having the same composition and structure as that of the sheet 2, or, for example, paper or unwoven fabric which has been cut to have a width narrower than that of the sheets 2. The width of the tape 4 is to have a width which can cover the notches 3 and which permits bonding by the pressure sensitive adhesive agent, and it is, for example, about 2 cm.

The pressure sensitive adhesive agent is provided between the sheet 2 and the tape 4 and preferably applied only on the tape 4. This prevents the pressure sensitive adhesive agent from sticking to the patient when the patient is turned from the right-side part 2R of the sheet 2 to the portion of the sheet 2 from which the left-side part 2L was removed when replacing the disposable sheets 1. Note that, the type of the pressure sensitive adhesive agent is not particularly limited.

Figure 6:
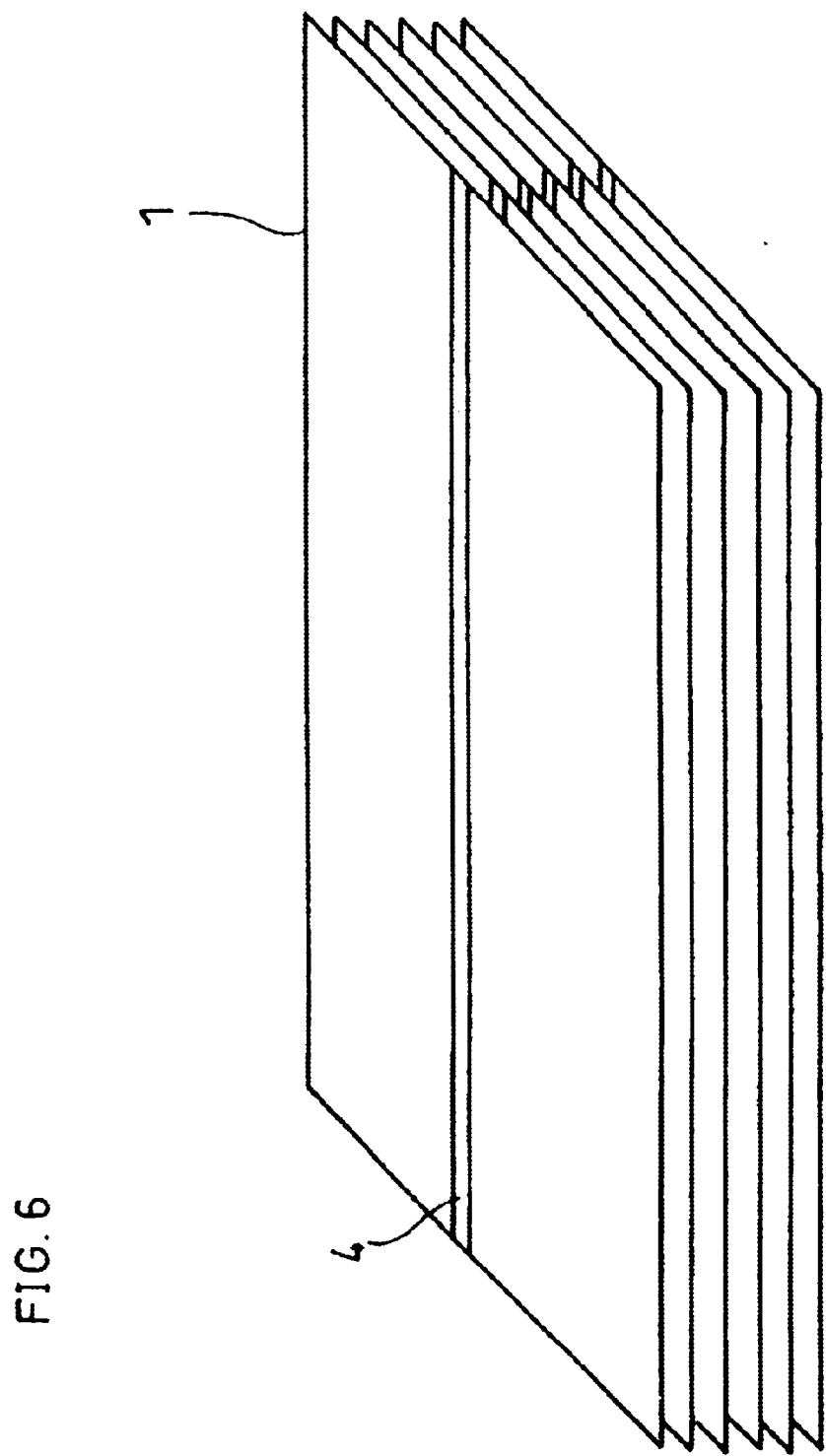
FIG. 6 is a perspective view showing one embodiment of a disposable sheet set of the present invention.

As shown in FIG. 6, the disposable sheets 1 are preferably used as a set of disposable sheets by stacking a plurality of disposable sheets 1 on one another. With this arrangement, once the patient is laid on the bed, the disposable sheets 1 can be replaced only by moving the sheets while the patient is lying thereon. This allows the disposable sheets 1 to be replaced only by a single care giver.

The number of disposable sheets 1 stacked is determined by the number of disposable sheets 1 which can be replaced while the patient is lying thereon. Also, the number of disposable sheets 1 is selected according to the period of replacing the disposable sheet set since the disposable sheet set needs to be replaced by moving the patient once all the disposable sheets of the disposable sheet set are used up. For example, when the number of disposable sheets is seven, the disposable sheet set is replaced every week, which may be convenient.

Note that, as shown in FIG. 6, the disposable sheets 1 are preferably stacked with the tape 4 facing upward. This allows the tape 4 to be easily peeled off when replacing the disposable sheets 1.

Figure 8:
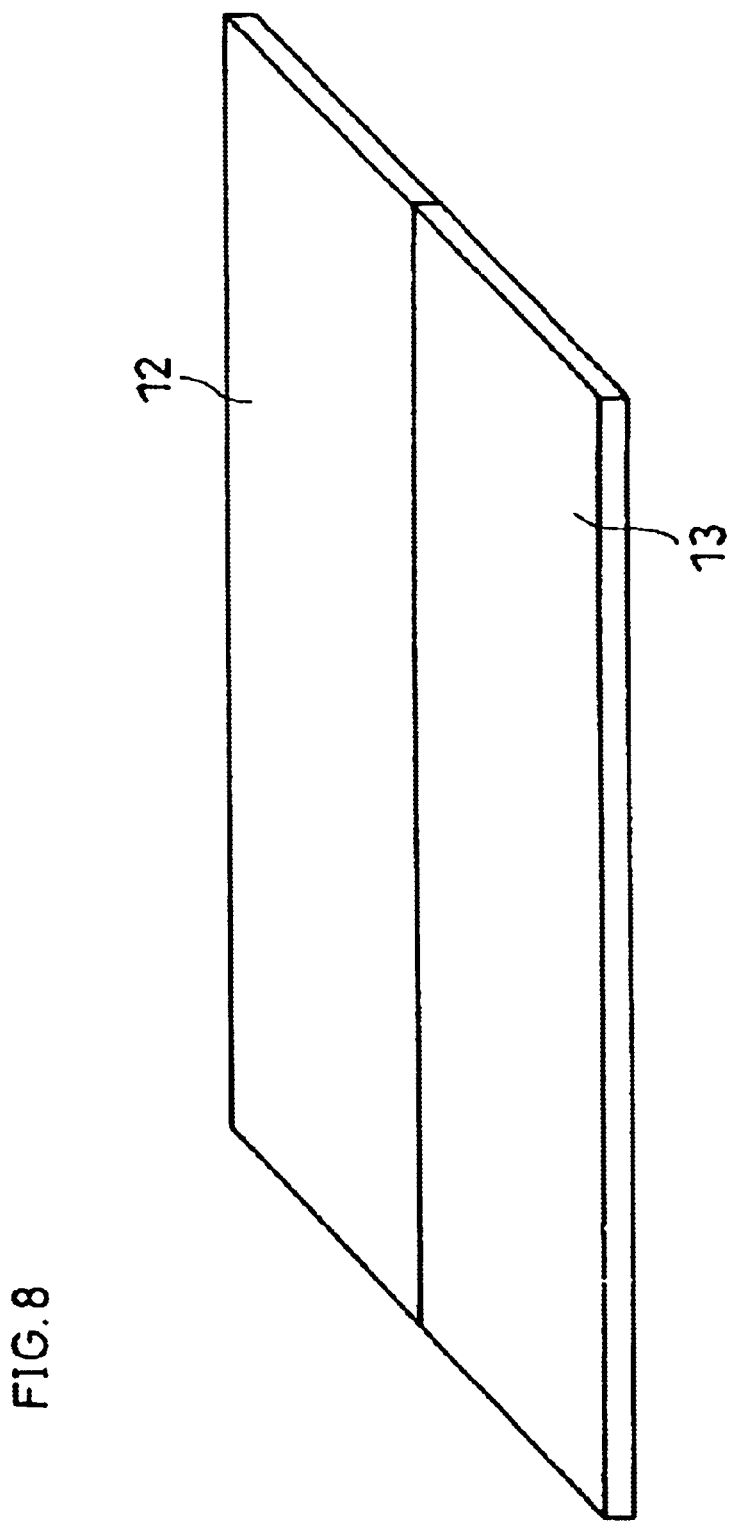
FIG. 8 is a perspective view of the disposable sheets of FIGS. 7(*a*) and 7(*b*), showing a state in which a tape is peeled off.
Figure 9:
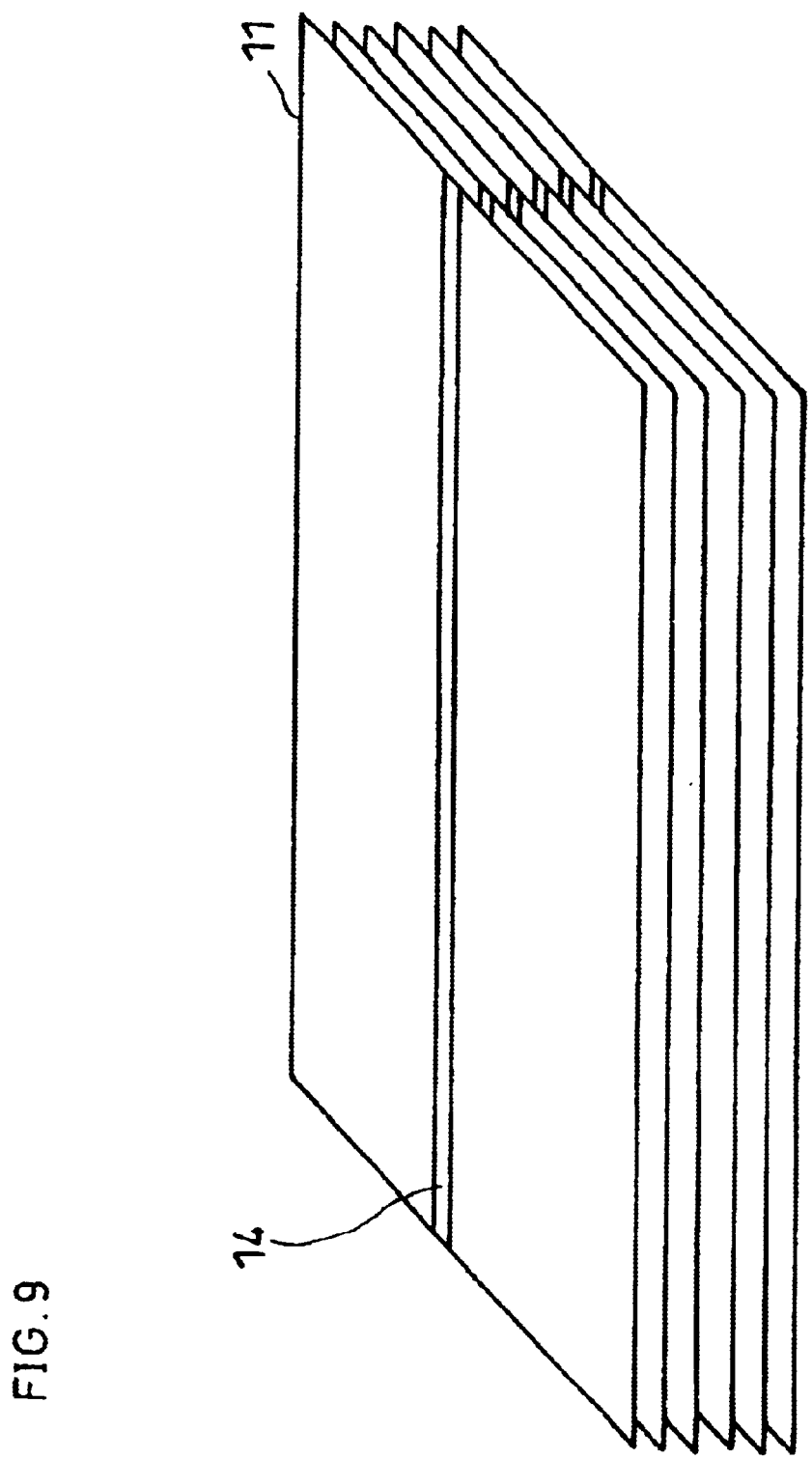
FIG. 9 is a perspective view showing another embodiment of the disposable sheet set of the present invention.

The following will describe another embodiment of the disposable sheets and disposable sheet set in accordance with the present invention with reference to FIGS. 7(*a*) and 7(*b*), and FIGS. 8 and 9.

As shown in FIGS. 7(*a*) and 7(*b*) in disposable sheets 11 of the present embodiment, two rectangular sheet elements 12 and 13 are disposed side by side with their longer sides contacting each other, and a tape 14 is attached on the sheet elements 12 and 13 by a pressure sensitive adhesive agent (not shown) so as to cover a portion of the sheet elements 12 and 13 in contact with each other.

The disposable sheets 11 can be used for beds of permanently-ill patients and removed only by moving it while the patient is laying thereon.

Specifically, in order to remove the disposable sheets 11, the body of a patient bridging over the sheet elements 12 and 13 is turned to the side on the sheet element 12 (or sheet element 13) to peel off the tape 14. As a result, as shown in FIG. 8, the sheet elements 12 and 13 become movable independently from the other. Then, by pulling the sheet element 13 (or sheet element 12) with hands, the sheet element 13 (or sheet element 12) is removed. Then, the body of the patient is turned to the side from which the sheet elements 13 (or sheet element 12) was removed, and the sheet element 12 (or sheet element 13) is pulled with hands to remove it.

Since the disposable sheets 11 can be removed while the patient is laying thereon, by placing another sheets under the disposable sheets 11, the sheets can be replaced while the patient is lying thereon. Accordingly, it is not required to move the patient from the bed, thus making it possible to replace sheets by a single care giver.

Further, in the disposable sheets 11, since the portion of the sheet elements 12 and 13 in contact with each other is covered with the tape 14, urine or sweat of the patient is prevented from seeping out into underlying sheets in use, for example, such as another disposable sheets 11, through a gap between the sheet elements 12 and 13.

The size of the disposable sheets 11 is suitably adjusted according to the size of the bed to which the disposable sheets 11 are applied, and it is set to have a size of about 150 cm×220 cm (width×length), for example.

In order to prevent the sheets to become sultry by sweat, etc., the sheet elements 12 and 13 are preferably made from sheets having gas permeability such as paper or unwoven fabric, or gas permeable sheets including additives. As such gas permeable sheets, paper and unwoven fabric are particularly preferable since they are inexpensive and have some absorbency to partially absorb urine or sweat, etc.

The sheet elements 12 and 13 preferably further include the antimicrobial and deodorizing agent such as the silver-chloro complex salts as additives. As a result, the sheet elements 12 and 13 can have the antimicrobial and deodorizing effects, thus maintaining further cleaner environment.

The sheet elements 12 and 13 preferably further include a polymer water absorbent as additives. This ensures to absorb urine or sweat, etc., and prevents urine or sweat, etc., to seep out into the underlying sheets through the sheet elements 12 and 13. As such a polymer water absorbent, polymer absorbent resin in the form of fine particles, as represented by "Aquakeep 10SH-NF" (product name, provided by Sumitomo Seika Chemicals Co., Ltd.) can suitably be used.

The method of adding the additives in the gas permeable sheet is not particularly limited, and it can be performed by kneading the additives with the raw material of the gas permeable sheet in manufacture thereof ("kneading method" hereinafter), or by sandwiching the additives between the gas permeable sheet and another sheet, which are then pasted together ("sandwiching method" hereinafter), or by dissolving the additives with a binding agent to have a solution and then soaking the gas permeable sheet in the solution ("soaking method" hereinafter). Note that, the sheet elements 12 and 13 of the gas permeable sheet having added the antimicrobial and deodorizing agent and the polymer water absorbent may be of the form of the sheet 2 as described in the First Embodiment, and, for example, the sheet 2 as shown in FIG. 4 or the sheet 2' as shown in FIG. 5 may be adopted.

The sheet elements 12 and 13 are preferably in the same size. As described, in order to replace the disposable sheets 11 while the patient is lying thereon, it is required to turn the patient to the sheet element 12 and then to the side from which the sheet element 13 was removed (e.g., on the sheet element 13 of underlying disposable sheets 11). By making the sheet elements 12 and 13 equal in size, it becomes relatively easier to turn the patient to the sheet element 12, and to the portion from which the sheet element 13 was removed.

The tape 14 may be a sheet having the same composition and structure as that of the sheet elements 12 and 13, or, for example, paper or unwoven fabric which has been cut to have a width narrower than that of the sheet elements 12 and 13. The width of the tape 14 is to have a width which can cover the portion of the sheet elements 12 and 13 in contact with each other, and which permits bonding by a pressure sensitive adhesive agent, and it is, for example, about 2 cm.

The pressure sensitive adhesive agent is provided between the sheet elements 12 and 13 and the tape 14 and preferably applied only on the tape 14. This prevents the pressure sensitive adhesive agent from sticking to the patient when the patient is turned from the sheet element 12 to the portion from which the sheet elements 13 was removed when replacing the disposable sheets 11. Note that, the type of the pressure sensitive adhesive agent is not particularly limited.

As shown in FIG. 9, the disposable sheets 11 are preferably used as a set of disposable sheets by stacking a plurality of disposable sheets 11 on one another. With this arrangement, once the patient is laid on the bed, the disposable sheets 11 can be replaced only by moving the sheets while the patient is lying thereon. This allows the disposable sheets 1 to be replaced only by a single care giver.

The number of disposable sheets 11 stacked is determined by the number of disposable sheets 11 which can be replaced while the patient is lying thereon. Also, the number of disposable sheets 11 is selected according to the period of replacing the disposable sheet set since the disposable sheet set needs to be replaced by moving the patient once all the disposable sheets 11 of the disposable sheet set are used up. For example, when the number of disposable sheets 11 is seven, the disposable sheet set is replaced every week, which may be convenient.

Note that, as shown in FIG. 9, the disposable sheets 11 are preferably stacked with the tape 14 facing upward. This allows the tape 14 to be easily peeled off when replacing the disposable sheets 11.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

INDUSTRIAL APPLICATIONS OF THE PRESENT INVENTION

As described, a first antimicrobial agent in accordance with the present invention includes silver-chloro complex salts and oxidizing agents.

With this constitution, it is possible to provide an antimicrobial agent having both immediate and sustained properties with respect to disinfection as well as deodorizing, having a wide disinfecting spectrum, capable of preventing resistant bacteria and having good safety, capable of sustaining sufficient stability even in a medium or environment where sulfides coexist, having a reasonable price, and having superior deodorizing action as well as antimicrobial and mildew proofing action.

As described, a producing method of the first antimicrobial agent in accordance with the present invention is adapted to mix a chloride aqueous solution, silver and/or silver compound, and oxidizing agents.

With this method, it is possible to provide an antimicrobial agent having both immediate and sustained properties with respect to disinfection as well as deodorizing, having a wide disinfecting spectrum, capable of preventing resistant bacteria and having good safety, capable of sustaining sufficient stability even in a medium or environment where sulfides coexist, having a reasonable price, and having superior deodorizing action as well as antimicrobial and mildew proofing action.

As described, a first antimicrobial treatment method in accordance with the present invention is adapted to treat a target object using an aqueous solution which contains the silver-chloro complex salts in the presence of the oxidizing agents.

With this method, it is possible to provide an antimicrobial agent having both immediate and sustained properties with respect to disinfection as well as deodorizing, having a wide disinfecting spectrum, capable of preventing resistant bacteria and having good safety, capable of sustaining sufficient stability even in a medium or environment where sulfides coexist, having a reasonable price, and having superior deodorizing action as well as antimicrobial and mildew proofing action.

As described, a second antimicrobial agent in accordance with the present invention includes the silver-chloro complex salts and chloride for supplying chloride ion, and the second antimicrobial agent further includes compounds having compatibility with a solvent dissolving the chloride, and more preferably a solvent (preferably water) which dissolves the chloride.

Thus, as the compounds having compatibility with the solvent which dissolves the chloride capture water or other solvent, it is possible to reduce the free water or solvent which is not chemically and physically captured in the vicinity of the silver-chloro complex salts in the antimicrobial agent solution. As a result, the apparent concentration of the silver-chloro complex salts, which contributes to stability of the silver-chloro complex salts, can be increased. Accordingly, it is possible to reduce the concentration of the chloride ion actually contained in the antimicrobial agent solution while maintaining a chloride ion concentration which is directly required for stabilizing the silver-chloro complex salts. Thus, with the foregoing constitution, it is possible to provide an antimicrobial agent which can easily effect the antimicrobial treatment without diluting the antimicrobial agent solution when using it.

As described, a second antimicrobial treatment method in accordance with the present invention is adapted to treat the target object with the second antimicrobial agent.

Thus, With this method, since it is not required to change the stored concentration of the chloride ion, the antimicrobial treatment can be effected conveniently.

As described, a third antimicrobial agent in accordance with the present invention includes a chloride which has at least one of (I) a property capable of existing as a super-saturated aqueous solution for 24 hours or longer in the presence of a crystal nucleus at least at room temperature, and (II) a property capable of being decomposed when dissolved in water, and the silver-chloro complex salts.

Thus, with this constitution, by the chloride having the foregoing properties, the chloride does not grow into white crystals, etc., on the surface of the target object even when the chloride is concentrated by the antimicrobial agent which has dried after the antimicrobial treatment, thus preventing appearance or feel of the target object from being spoiled.

As described, a fourth antimicrobial agent in accordance with the present invention includes the silver-chloro complex salts and the chloride, and is a solid.

Thus, since the antimicrobial agent is a solid, it is possible to provide an antimicrobial agent having wide use, for example, such as mixing with a powder such as a powder detergent, or kneading with resin or fiber in the form of fine particles. Further, by the silver-chloro complex salts having the sustained antimicrobial property and by the chloride which stabilizes the silver-chloro complex salts, it is possible to provide an antimicrobial agent having stable antimicrobial properties.

As described, a producing method of the fourth antimicrobial agent in accordance with the present invention includes the steps of preparing a mixture by mixing the silver and/or silver compound, chloride for supplying chloride ion, and water, and removing water from the mixture.

Thus, since the mixture contains the chloride, the silver-chloro complex salts exist stably even when water is removed from the mixture, thus producing a solid antimicrobial agent having stable antimicrobial properties. As a result, it is possible to provide a producing method of an antimicrobial agent having wide use, for example, such as mixing with a powder such as a powder detergent, or kneading with resin or fiber in the form of fine particles. Further, by the silver-chloro complex salts having the sustained antimicrobial property and by the chloride which stabilizes the silver-chloro complex salts, it is possible to provide a producing method of the antimicrobial agent having stable antimicrobial properties.

As described, a detergent in accordance with the present invention includes the silver-chloro complex salts.

Thus, the antimicrobial treatment can be effected on the washing target object without resulting in change in color of the washing target object (target object). Further, the sustained antimicrobial property can easily be effected in washing. Also, since there is no reaction with the ingredients contained in the detergent, for example, such as the anionic surfactant and thus the antimicrobial ability can be stably maintained, it is possible to demonstrate washing and antimicrobial effects at the same time, among other effects. Further, antiseptic effect can be obtained for the detergent.

As described, a laundry supplement in accordance with the present invention includes the silver-chloro complex salts.

Thus, for example, when used with a softening agent, the antimicrobial treatment can be effected on the washing target object without resulting in change in color of the washing target object (target object) while effecting the softening property. Further, the sustained antimicrobial property can be conveniently effected when the softening property, etc., is effected. Also, since there is no reaction with ingredients contained in the laundry supplement, for example, in the anionic surfactant, and thus the antimicrobial ability can be maintained stably, it is possible to effect the antimicrobial effect, among other effects, at the same time when the softening property, etc., is effected. Further, antiseptic effect can be obtained for the laundry supplement.

As described, a third antimicrobial treatment method in accordance with the present invention is adapted to treat the target object in a solution containing the silver-chloro complex salts.

Thus, the antimicrobial treatment can easily be effected without resulting in change in color of the target object. Further, the antimicrobial effect can easily be sustained on the target object.

As described, disposable sheets in accordance with the present invention include notches with respect to and in the longitudinal direction of a rectangular sheet so that the sheet can be separated into two, and a tape for sealing the notches is stuck on the sheet by a pressure sensitive adhesive agent covering the notches.

Thus, with this constitution, it is possible to provide disposable sheets which can be removed while a person is lying thereon.

As described, disposable sheets in accordance with the present invention include two rectangular sheet elements which are disposed side by side with their longer sides contacting each other, and a tape is attached on the sheet elements by a pressure sensitive adhesive agent so as to cover a portion of the sheet elements in contact with each other.

Thus, with this constitution, it is possible to provide disposable sheets which can be removed while a person is lying thereon.

As described, a disposable sheet set in accordance with the present invention has the disposable sheets, any of which are stacked one over another.

Thus, with this constitution, it is possible to provide a disposable sheet set which allows a single care giver to replace the sheets when used for beds of permanently-ill patients.

What is claimed is:

1. A antimicrobial agent which includes silver-chloro complex salts of the formula:

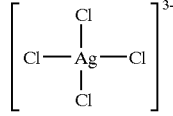

and a chloride for supplying chloride ion, and is a solid.

2. The antimicrobial agent of claim 1, wherein a weight ratio of the silver-chloro complex salts and the chloride is in a range of $1:10^5$ to 1:10.

3. The antimicrobial agent of claim 1, wherein a weight ratio of the silver-chloro complex salts and the chloride is in a range of 1:1000 to 1:50.

4. The antimicrobial agent of claim 1, wherein a weight ratio of the silver-chloro complex salts and the chloride is in a range of 1:200 to 3:200.

5. A powder detergent including the antimicrobial agent of claim 1.

6. A method of producing an antimicrobial agent which includes silver-chloro complex salts of the formula:

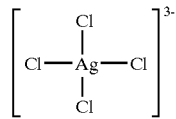

comprising the steps of:

(a) preparing a mixture by mixing a sufficient amount of a silver and/or silver compound, and a sufficient amount of a chloride for supplying chloride ion to form said complex salts, and adding water in an amount to make a paste of the silver or silver compound and the chloride, and preparing a paste by uniformly mixing to form said complex salts in the paste state, and (b) removing water by evaporating it from the paste prepared in step (a).

7. The method of claim 6, wherein step (a) of preparing the mixture is so that a weight ratio of the chloride, based on the weight of the silver or silver compound, is not less than 1.3 in a weight ratio when a weight ratio of the silver or the silver compound is 1.

8. The method of claim 6, wherein step (b) of removing the water from the mixture is by drying the mixture to desiccate it.

9. The method of claim 6, wherein:

a temperature of the mixture is in a range of 20° C. to 200° C. in step (b) of removing the water from the mixture.

* * * * *